(12) United States Patent
Guichard et al.

(10) Patent No.: US 7,060,845 B2
(45) Date of Patent: Jun. 13, 2006

(54) STABILIZED ACTIVATED DERIVATIVES OF CARBAMIC ACID, THEIR PROCESS OF PREPARATION AND THEIR USE FOR THE PREPARATION OF UREAS

(75) Inventors: Gilles Guichard, Wolfisheim (FR); Marc Rodriguez, deceased, late of Strasbourg (FR); by Marie-Christine Galas-Rodriguez, legal representative, Strasbourg (FR); by Pierre Rodriguez, legal representative, Strasbourg (FR); by Elisa Rodriguez, legal representative, Strasbourg (FR); by Romain Rodriguez, legal representative, Strasbourg (FR); Vincent Semetey, Strasbourg (FR); Jean-Paul Briand, Strasbourg (FR)

(73) Assignees: Neomps, Strasbourg (FR); Centre National de la Recherche Scientifique, Paris Cedex (FR)

( * ) Notice: Subject to any disclaimer, the term of this patent is extended or adjusted under 35 U.S.C. 154(b) by 457 days.

(21) Appl. No.: 09/904,459

(22) Filed: Jul. 16, 2001

(65) Prior Publication Data

US 2002/0143191 A1 Oct. 3, 2002

Related U.S. Application Data

(63) Continuation of application No. PCT/FR00/00080, filed on Jan. 14, 2000.

(30) Foreign Application Priority Data

Jan. 14, 1999 (FR) .................................. 99 00330

(51) Int. Cl.
C07D 207/00 (2006.01)
C07D 207/46 (2006.01)
(52) U.S. Cl. ...................................... 548/528; 548/542
(58) Field of Classification Search ................ 548/542, 548/528
See application file for complete search history.

(56) References Cited

U.S. PATENT DOCUMENTS

| 3,637,811 A | 1/1972 | Zenner et al. |
| 4,003,912 A | 1/1977 | Franz ....................... 260/326.4 |
| 4,680,338 A | 7/1987 | Sundoro .................... 525/54.1 |
| 4,929,736 A | 5/1990 | Groutas ..................... 548/341 |

FOREIGN PATENT DOCUMENTS

| EP | 0 533 200 | 3/1993 |
| JP | 62-195361 | 2/1987 |

OTHER PUBLICATIONS

Lin et al. (Bioorganic & Medicinal Chemistry Letters 9 (22) (1999), pp. 3237-3242).*
Guihard et al. (Journal of Organic Chemistry (1999), 64 (23), 8702-8705).*
Guichard et al. (J. Org. Chem. 1999, 64, 8702-8705).*
J. Kruijtzer et al., Approaches to the Synthesis of Ureapeptoid Peptidomimetics, *Tetrahedron Letters*, vol. 38, No. 30, pp. 5335-5338, 1997.
L. Richter et al., "Curtius Degradation in Solid-Phase Synthesis", *Tetrahedron Letters*, vol. 39, 1998, pp. 8747-8750.
D. Neel et al., "Synthesis of a 3-Keto Bicyclic Pyrazolidinone Using a Curtius Rearrangement", *Tetrahedron Letters*, vol. 37, No. 28, pp. 4891-4894.
J. Conroy et al., "Using the Electrostatic Field Effect to Design a New Class of Inhibitors for Cysteine Proteases", *J. Am. Chem. Soc.*, 1997, No. 119, pp. 4285-4291.
T. Shiori et al., "Diphenylphosphoryl Azide. A New Convenient Reagent for a Modified Curtius Reaction and for the Peptide Synthesis", *J. Am. Chem. Soc.*, 94:17, Aug. 23, 1972.
K. Burgess et al., "Solid Phase Syntheses of Oligoureas", *J. Am. Chem. Soc.* 1997, No. 119, pp. 1556-1564.
C. Corral et al., "Synthesis of 5-Amino-2,3-dihydro-1H-1,4-benzodiazepines (1)", *J. Heterocyclic Chem.*, No. 14, p. 985 (1977).
J. Martinez et al., "Activated N-Nitrosocarbamates for Regioselective Synthesis of N-Nitrosoureas", *J. Med. Chem.*, 1982, No. 25, pp. 178-182.
J. Kim et al., "The Solid Phase Synthesis of Oligoureas", *Tetrahedron Letters*, vol. 37, No. 30, pp. 5305-5308, 1996.

* cited by examiner

*Primary Examiner*—Bruck Kifle
(74) *Attorney, Agent, or Firm*—Young & Thompson

(57) ABSTRACT

Process for the preparation of stable activated derivatives of carbamic acid, comprising at least one protected amino group and an activated carbamic acid function, from an amino acid derivative in which the amino group is protected. The process includes: a) a step of transformation of the —COOH group of the amino acid derivative into a —CON$_3$ group to obtain an acyl azide; b) a step of transformation of the —CON$_3$ group of the acyl azide into a —NCO group to obtain an isocyanate; c) a step of treating the isocyanate to obtain a stable derivative of carbamic acid.

13 Claims, 1 Drawing Sheet

Figure 1:
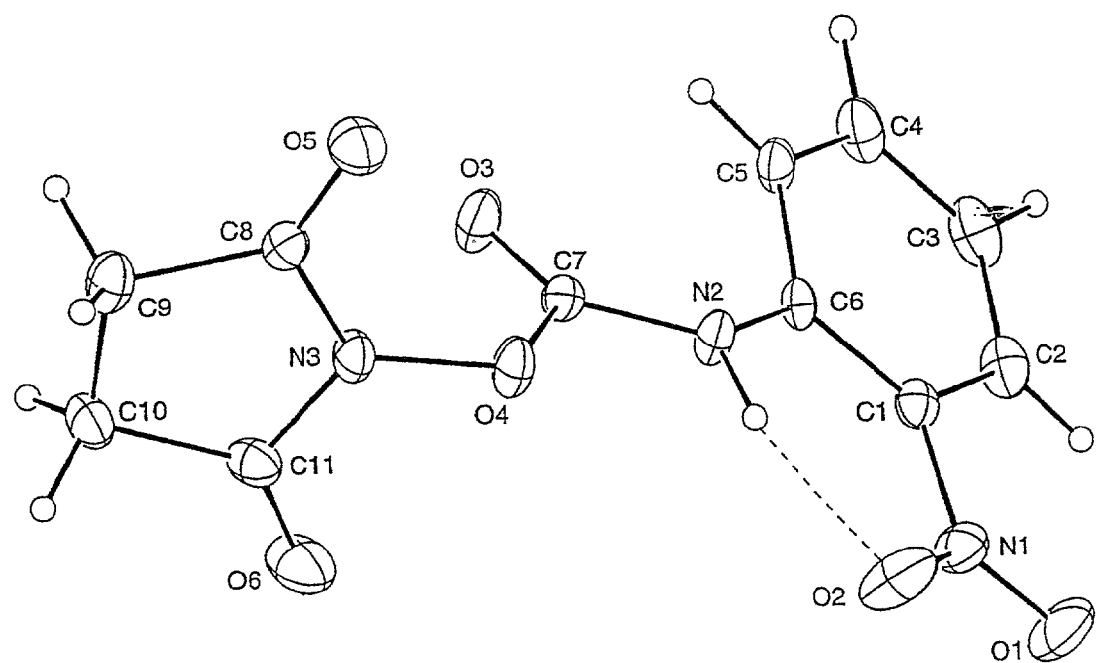

STABILIZED ACTIVATED DERIVATIVES OF CARBAMIC ACID, THEIR PROCESS OF PREPARATION AND THEIR USE FOR THE PREPARATION OF UREAS

This is a continuation of co-pending international application PCT/FR00/00080, filed on 14 Jan. 2000, which designates the United States of America.

The invention has for its object new stable activated derivatives of carbamic acid, particularly new stable activated carbamates, their process of preparation and their use for the preparation of urea.

The synthesis and applications of substituted ureas has for several years undergone great development. These compounds are present in a certain number of active principles now under development in the pharmaceutical industry as protease inhibitors of VIH, antagonists of the CCK-B receptor, or antagonists of endothelin[1]. Moreover, the oligoureas have been introduced as "scaffolds" for the creation of β-sheets[2] or as mimics of the peptide skeleton[3]. The methods of formation of substituted ureas rely on the reaction of amines with carbonylation agents[4], with isocyanates[5] or with carbamates[6].

In the field of research looking toward the development of new compounds with immunomodulatory activity, there is needed a simple method, not requiring the use of phosgene or of one of its derivatives, to produce easily peptidic analogs containing ureas or urea oligomers. In 1995, the Burgess group described for the first time the synthesis in solid phase of oligoureas. This was based on the use of isocyanate synthons derived from N-protected mono-phthalimide diamines. This strategy requires the preparation of protected mono-phthalimide diamines precursors and uses triphosgene as the carbonylation agent to obtain the corresponding isocyanate[3a,3b]. In a similar approach, the Schultz group used azido 4-nitrophenyl carbamates as pre-activated synthons[3c,3d]. More recently, 4-nitrophenyl carbamates obtained by the reaction of Boc-protected N-substituted ethylenediamines with 4-nitrophenyl chloroformate have been described as synthons for the synthesis of urea-peptoids by the Liskamp group[3e]. In short, there does not exist at present an easy synthesis route for activated monomers obtained from amino acids protected or not by an Fmoc, Boc or Z group, avoiding the use of phosgene (or its derivatives) and permitting the synthesis of urea oligomers as well as the easy incorporation of urea patterns in peptides. The activated carbamates are generally prepared by the reaction of amines with carbonates[4c] or chloroformates[3e,6b], or by reaction of isocyanates with alcohols[6a].

One of the aspects of the invention is to provide novel stable activated derivatives of carbamic acid, in particular novel stable activated carbamates.

One of the other aspects of the invention is to provide novel isocyanates.

One of the other aspects of the invention is to provide a novel process for the preparation of urea, cyclic or not.

One of the other aspects of the invention is to provide novel ureas, cyclic or not.

Generally speaking, the invention has for its object the use of isocyanates obtained from amino acid derivatives for the preparation and if desired the isolation of stable activated derivatives of carbamic acid or of stable activated carbamates.

According to a preferred embodiment, the invention relates to the use of isocyanates, of stable activated derivatives of carbamic acid, or of stable activated carbamates defined above, for the preparation of substituted ureas, cyclic or not, particularly of oligomers of ureas, cyclic or not, or for the preparation of peptides or pseudo-peptides containing urea designs, cyclic or not.

By "amino acid derivatives", is meant amino acids (alpha, beta, gamma, delta-aminated, or the like) whose primary or secondary amine function can be protected by a group selected to give a tertiary amine function, urethane, amide, urea, nitro or phthalimide.

Within the meaning of the invention, the term "amino acid derivatives" should be interpreted in its broad sense, as understood by those in the art, and designates particularly a derivative of peptide, polypeptide, protein, pseudopeptide or oligourea.

By "activated carbamate" or "activated derivative of carbamic acid", is meant a carbamate or a carbamic acid derivative capable of reacting with primary or secondary amines or with alcohols in the presence of not of a base in an organic solvent and generally at ambient temperature.

By "stable carbamate" or "stable carbamic acid derivative", is meant a stable carbamate or a stable derivative of carbamic acid because it is isolable, purifiable and can be stored (preferably at 4° C.) for a period of at least 3 months without noticeable degradation. The stability can be measured for example by the following test: HPLC or thin layer chromatography.

By "isolation" is meant the process of separation of the desired product from all of the impurities present in the reaction mixture (the latter can be for example: an excess of one of the reagents used to carry out the reaction, symmetrical urea, the amine obtained by the rearrangement of isocyanate in the presence of water) and the recovery of the thus-purified product in a form permitting it to be stored (preferably at 4° C.) for a long period (several months, at least 3 months) without noticeable decomposition.

The expression "urea oligomers" means a successive chain of motifs interconnected by urea linkages (at least two)

For example: $NH_2$—$CHR_1$—$CHR'_1$—NH—CO—NH—$CHR_2$—$CHR'_2$—NH—CO—NH—$CHR_3$—$CHR'_3$—$CONH_2$ The invention particularly has for its object a process for the production of stable activated derivatives of carbamic acid, from an amino acid derivative in which the amino group is protected, comprising:

a) a step of transforming the —COOH group of the amino acid derivative into the —$CON_3$ group to obtain an acyl azide, b) a step of transforming the —$CON_3$ group of the acyl azide into the —NCO group to obtain an isocyanate, c) a step of treating the isocyanate to obtain said stable derivative of carbamic acid.

According to a preferred embodiment of the process of the invention, step a) for the transformation of the —COOH group into the —$CON_3$ group, is carried out by a treatment, with the nitride anion, of an activated derivative of the amino acid in which the amino group is protected.

By way of example, the nitride anion could be used in the form of sodium azide.

Thus, step a) of transformation of the —COOH group into the —$CON_3$ group could be carried by treatment of the mixed anhydride (formed from the amino acid derivative) with sodium azide.

Generally speaking, any method known to those skilled in the art permitting obtaining an azide from an acid can be used, and particularly those described in the encyclopedia of Houben-Weyl, "Methoden der organischen Chemie".

According to another preferred embodiment of the process of the invention, step a) for transformation of the —COOH group into the —CON₃ group is carried out by the treatment, with hydrazine, of an activated amino acid derivative in which the amino group is protected, to obtain a hydrazide, which is then subjected to a nitrosation.

By "activated derivative of amino acid" is meant for example an acid ester or an acid halide, such as an acid chloride.

By way of example, carboxylic acid is first converted to an active derivative (ester, chloride etc . . . ) that the action of hydrazine transforms into a hydrazide, which is then transformed into the desired acyl azide, by the action of nitrous acid.

According to another preferred embodiment of the invention, the transformation of the —COOH group into the —NCO group can be carried out by the method using unsymmetrical disubstituted dimethylhydrazine ("UDMH"), according to the synthesis reaction indicated below by way of example:

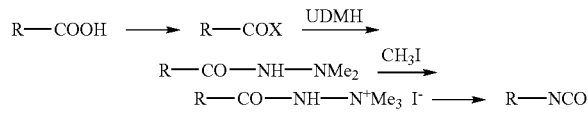

The invention also has for its object compounds according to the formula (I):

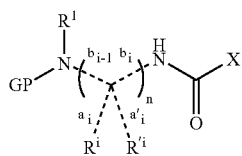

in which

"n" is a whole number greater than or equal to 1, preferably 1 to 50, preferably 1 to 10, "i" is a whole number varying from 2 to n+1, "$a_i$ and $a'_i$", shown by a dotted line, are covalent bonds which can be single (s) or double (d), "$b_i$ and $b_{i-1}$", represented by broken lines, are covalent bonds which can be single (s), double (d) or triple (t), provided that:

$b_1$ and $b_{n+1}$ are always single bonds (s), if $b_i$=d, then $a_i$ and $a_{i+1}$=s; $a'_i$ and $a'_{i+1}$=Ø; $b_{1-i}$ and $b_{i+1}$=s if $b_i$=t, then $a_i$ and $a_{i+1}$=Ø; $a'_1$ and $a'_{i+1}$=Ø; $b_{i-1}$ and $b_{i+1}$=s if $a_i$=d, then $b_{i-1}$ and $b_i$=s, certain of these linkages $a_i$, $a'_1$, $b_{i-1}$ can also form parts of aromatic rings, GP is a protective group selected from:

oxycarbonyl (GP=ROCO), preferably Boc (R=C(CH₃)₃), Fmoc (fluorenylmethoxycarbonyl), benzyloxycarbonyl (R=CH₂Ph), allyloxycarbonyl (R=—CH₂CH=CH₂), acyl (GP=RCO), preferably R=CH₃, CH₂CH₃, CH(CH₃)₂, C(CH₃)₃, phenyl, benzyl, allyl, aryl, alkyl (GP=R), preferably R=trityl, CH₃, CH₂CH₃, CH(CH₃)₂, C(CH₃)₃, benzyl, allyl, aryl, particularly phenyl, urea (GP=RNHCO), preferably R=H, CH₃, CH₂CH₃, CH(CH₃)₂, C(CH₃)₃, phenyl, benzyl, allyl, phthalimide (R¹=Ø)

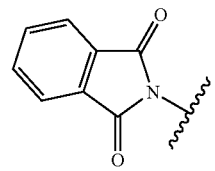

O₂ (corresponds to a nitro group masked with amine), R¹=Ø the groups R¹, $R^i$, $R'^i$ and R can each represent independently one of the other:

hydrogen, halogen, the side chain of amino acid selected from natural or synthetic amino acids, an alkyl (C1–C20) group, substituted or not with one or several of the following substituents:

1/ —COOR$_a$
2/ —CONHR$_a$
3/ —COOH
4/ —OH
5/ —OR$_a$
6/ —NHR
7/ —NH₂
8/ —NH(CO)R$_a$
9/ aryl, whose cyclic structure contains 5 to 20 carbon atoms
10/ halogen
11/ carbonyl of 1 to 10 carbon atoms
12/ nitrile
13/ guanidine
14/ nitro an aryl group whose cyclic structure contains 5 to 20 carbon atoms an alkoxy group OR$_a$ an NH₂ group an OH group —COOR$_a$
—CONHR$_a$
—CONH₂
—CH₂COOR$_a$
—CH₂CONHR$_a$
—CH₂CONH₂

R$_a$ representing an alkyl group of 1 to 20 carbon atoms, or an aryl group whose cyclic structure contains 5 to 20 carbon atoms, the group X represents a group conferring on the compound of formula I an activated carbamate structure, which X group comes from a compound selected particularly from phenol, if desired substituted with at least one nitro or at least one halogen, or hydroxylamine derivatives, and more particularly selected from the following compounds:

N-hydroxysuccinimide phenol pentafluorophenol pentachlorophenol p-nitrophenol 2,4-dinitrophenol
2,4,5-trichlorophenol
2,4-dichloro-6-nitrophenol
hydroxy-1,2,3-benzotriazole
1-oxo-2-hydroxydihydrobenzotriazine (HODfhbt)
7-aza-1-hydroxybenzotriazole (HOAt)
4-aza-1-hydroxybenzotriazole (4-HOAt)
tetrazole
imidazole the compound of formula (I) having the following property:
if one or several asymmetric carbons are present in the formula (I), then their configuration can be independently either D (dextro) or L (levo),
the groups $R^1$, $R^i$, $R^{\prime i}$ can also be defined on the basis of intramolecular cyclizations which are as follows:
1/ cyclization between $R^i$ and $R^{\prime i}$
2/ cyclization between $R^i$ or $R^{\prime i}$ and $R^{i+kc}$ (where kc is a positive whole number, preferably from 1 to 3)
3/ cyclization between $R^1$ and $R^i$ or $R^{\prime i}$ wherein preferably i=2, 3 or 4,
provided that the compound of formula (I) is different from the following compounds, in which:
n=2, GP=Boc, $R^1$=isobutyl, $R^2$=$R^{\prime 2}$=$R^3$=$R^{\prime 3}$=H, X=4-nitrophenol,
n=2, GP=Boc, $R^1$=benzyl, $R^2$=$R^{\prime 2}$=$R^3$=$R^{\prime 3}$=H, X=4-nitrophenol,
n=2, GP=Boc, $R^1$=$CH_2$-p-$C_6H_4$Ot-Bu, $R^2$=$R^{\prime 2}$=$R^3$=$R^{\prime 3}$=H, X=4-nitrophenol,
n=2, GP=Boc, $R^1$=H, $R^2R^{\prime 2}$=$R^3$=$R^{\prime 3}$=H, X=4-nitrophenol.

The first bond $b_1$ and the last $b_{n+1}$ each connected to a nitrogen atom, are always single bonds: *$b_1$ and $b_{n+1}$ are always single bonds (s).

If a $b_i$ bond is double, this implies that the adjacent bonds $b_{i-1}$, $b_{i+1}$, $a_i$ and $a_{i+1}$ are single bonds and that the bonds $a^\prime_i$ and $a^\prime_{i+1}$ do not exist:
if $b_i$=d, then $a_i$ and $a_{i+1}$=s; $a^\prime_i$ and $a^\prime_{i+1}$=Ø; $b_{i-1}$ and $b_{i+1}$=s If a $b_i$ bond is triple, this implies that the adjacent bonds $b_{i-1}$, $b_{i+1}$ are single bonds and that the bonds $a_i$, $a^\prime_i$, $a_{i+1}$ and $a^\prime_{i+1}$ do not exist:
if $b_i$=t, then $a_i$ and $a_{i+1}$=Ø; $a^\prime_i$ and $a^\prime_{i+1}$=Ø; $b_{i-1}$ and $b_{i+1}$=s If an $a_i$ bond is double, this means that the adjacent bonds $b_{i-1}$ and $b_i$ are single bonds and that the bond $a^\prime_i$ does not exist.
if $a_i$=d, then $b_{i-1}$ and $b_i$=s.

The symbol Ø corresponds to the absence of the bond to which it relates.

The expression "certain of the bonds could also be part of aromatic rings, substituted or not" can be explained in the following manner. These cases can occur:
n≧2: the bonds $a_i$, $a_{i+1}$, and $b_i$ belong to the aromatic cycle; the bond $b_{i+1}$ is in the ortho position relative to the $b_{i-1}$ bond.
n≧3: the bonds $a_i$, $a_{i+2}$, $b_i$ and $b_{i+1}$ belong to the aromatic cycle; the $b_{i+2}$ bond is in the meta position relative to the $b_{i-1}$ bond.
n≧4: the bonds $a_i$, $a_{i+3}$, $b_i$, $b_{i+1}$ and $b_{i-2}$ belong to the aromatic cycle; the bond $b_{i+3}$ is in the ortho position relative to the $b_{i-1}$ bond.

If there is cyclization between $R^1$, $R^i$ and $R^{\prime i}$, they can be illustrated in the following manner:

1/ Cyclization between $R^i$ and $R^{\prime i}$:
by way of illustration, the three following molecules, in which n=2, contain cyclization between $R^2$ and $R^{\prime 2}$

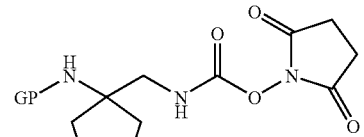

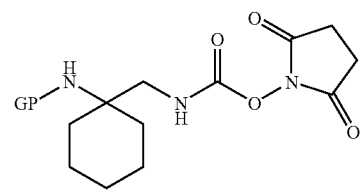

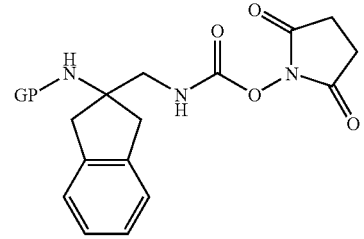

2/ Cyclization between $R^i$ (or $R^{\prime i}$) and $R^{i+k}$ (where k can be a whole positive number comprised between 1 and 3):
by way of illustration, the three following molecules in which n=2, contain cyclization between $R^2$ and $R^3$ (in this case k is equal to 1)

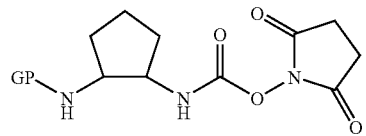

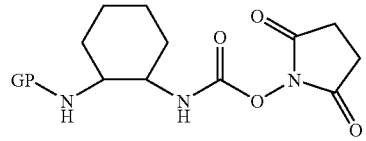

3/ Cyclization between $R^1$ and $R^i$ (or $R^{\prime i}$) wherein preferably i=2, 3 or 4:
by way of illustration, the three following molecules in which n=2, contain a cyclization between $R^1$ and $R^2$ (or $R^1$ and $R^3$)

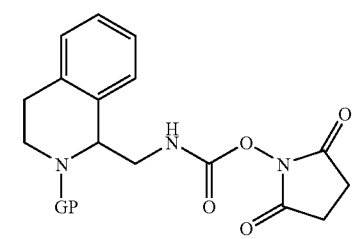

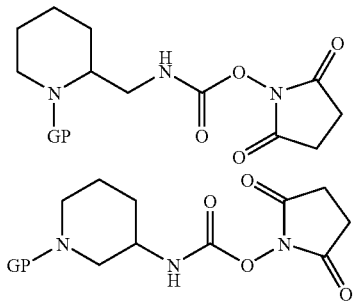

In all the formulas indicated above and hereafter, when GP=RCO or ROCO, R preferably represents a hydrocarbon chain.

In all the formulas indicated above and hereinbelow, when GP=ROCO, GP forms with the nitrogen atom to which it is contiguous a urethane group.

In all the formulas indicated hereafter, when A=ROCO, A forms with the nitrogen atom to which it is contiguous a urethane group.

The invention also relates to compounds of the formula (III)

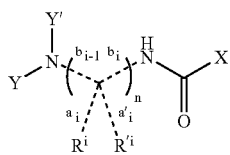

in which
"n" is a whole number greater than or equal to 1, preferably 1 to 50, preferably 1 to 10,
"i" is a whole number varying from 2 to n+1,
$a_i$ and $a'_i$, represented in broken lines, are covalent bonds which can be single (s) or double (d),
$b_i$ and $b_{i-1}$, represented by broken lines, are covalent bonds which can be single (s), double (d) or triple (t) provided that:
$b_1$ and $b_{n+1}$ are always single bonds (s),
if $b_i$=d, then $a_i$ and $a_{i+1}$=s; $a'_i$ and $a'_{i+1}$=Ø; $b_{i-1}$ and $b_{i+1}$=s
if $b_i$=t, then $a_i$ and $a_{i+1}$=Ø; $a'_i$ and $a'_{+1}$=Ø; $b_{i-1}$ and $b_{i+}$=s,
if $a_i$=d, then $b_{i-1}$ and $b_i$=s,
certain of these bonds $a_i$, $a'_i$, $b_{i-1}$ can also form part of aromatic rings,
the groups $R^1$, $R^i$ and $R^{'i}$ can each represent independently one of the other:
hydrogen,
the side chain of an amino acid selected from natural or synthetic amino acids
a (C1–C20) alkyl group, unsubstituted or substituted with one or several of the following substituents:
1/ —COOR$_a$
2/ —CONHR$_a$
3/ —COOH
4/ —OH
5/ —OR$_a$
6/ —NHR$_a$
7/ —NH$_2$
8/ —NH(CO)R$_a$
9/aryl, whose cyclic structure contains 5 to 20 carbon atoms
10/ halogen
11/ carbonyl
12/ nitrile
13/ guanidine
14/ nitro
an aryl group whose cyclic structure contains 5 to 20 carbon atoms
an OR$_a$ group
an NH$_2$ group
an OH group
—COOR$_a$
—CONHR$_a$
—CONH$_2$
—CH$_2$COOR$_a$
—CH$_2$CONHR$_a$
—CH$_2$CONH$_2$ R$_a$ representing an alkyl group of 1 to 20 carbon atoms, or an aryl group whose cyclic structure contains 5 to 20 carbon atoms,
the groups Y and Y' can be or contain:
1/ a pseudopeptide (peptide containing one or several pseudopeptide bonds)

$$A\text{-}N(Z_1)\text{—}C(Z'_1)(Z''_1)\text{-}\Psi_1[*]\text{-} \ldots \text{-}\Psi_{k-1}[*]\text{-}C(Z'_k)(Z''_k)\text{-}\Psi_k[*]\text{-} \ldots \Psi_{p-1}[*]C(Z'_p)(Z''_p)\text{-}\Psi_p[*]\text{-}$$

p is a whole number greater than or equal to 1, preferably 1 to 50, and particularly 1 to 10,
k is a whole number varying from 1 to p,
A is a group selected from:
hydrogen
oxycarbonyl (ROCO), preferably Boc (R=C(CH$_3$)$_3$), Fmoc (fluorenylmetoxycarbonyl), benzyloxycarbonyl (R=CH$_2$Ph), allyloxycarbonyl (R=—CH$_2$CH═CH$_2$),
acyl (RCO), preferably R=CH$_3$, CH$_2$CH$_3$, CH(CH$_3$)$_2$, C(CH$_3$)$_3$, phenyl, benzyl, allyl, aryl,
alkyl (R), preferably R=trityl, CH$_3$, CH$_2$CH$_3$, CH(CH$_3$)$_2$, C(CH$_3$)$_3$, benzyl, allyl,
phenyl, particularly aryl,
urea (RNHCO), preferably R=CH$_3$, CH$_2$CH$_3$, CH(CH$_3$)$_2$, C(CH$_3$)$_3$, phenyl, benzyl, allyl,
phthalimide (R1=Ø)

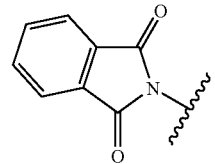

biotin
$Z_k$, $Z'_k$ and $Z''_k$ can each represent independently one of the other:
hydrogen,
the side chain of an amino acid selected from proteinogenic and non-proteinogenic amino acids
a (C1–C20) alkyl group unsubstituted or substituted by one or several constituents from the following:
1/ —COOR$_b$
2/ —CONHR$_b$
3/ —COOH
4/ —OH, OR$_b$
5/ —NHR$_b$
6/ —NH$_2$ 7/ —NH(CO)$R_b$ 8/ aryl whose cyclic structure contains 5 to 20 carbon atoms 9/ halogen 10/ carbonyl of 1 to 10 carbon atoms 11/ nitrile 12/ guanidine an aryl group whose cyclic structure contains 5 to 20 carbon atoms a halogen —$OR_b$ —$COOR_b$ —$CONHR_b$

—$CONH_2$

—$CH_2COOR_b$

—$CH_2CONHR_b$

—$CH_2CONH_2$ $R_b$ representing an alkyl group of 1 to 20 carbon atoms, or an aryl group whose cyclic structure contains 5 to 20 carbon atoms.

-$\Psi_k$[*]- are independently either peptidic linkages CO—NH or bonds of different chemical nature selected particularly from the following list, which is not limiting:

$\Psi_k$[*]-=—$CH_2CH_2$; —$CH(F_k)$=$CH(F_k')$—; —$CH_2NH$—; —NHCO—; —NHCONH—; —$COCH_2$—; —$CH(OH)CH_2$—; —CH(OH)$CH_2NH$—; —$CH_2$—; —$CH(F_k)$—; —$CH_2O$—; —$CH_2$—NHCONH—; $CH(F_k)NHCONF_k'$—; $CH_2$—CONH—; $CH(F_k)CONH$—; —$CH(F_k)CH(F_k')$CONH—

Fk and Fk' representing, independently from each other, hydrogen, halogen, an alkyl group of 1 to 20 carbon atoms, or an aryl group whose cyclic structure contains 5 to 20 carbon atoms.

2/ an amino acid residue or an amino acid chain:

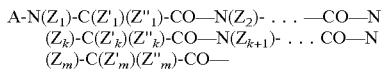

m is a whole number greater than or equal to 1, preferably 1 to 50, preferably 1 to 10, k is a whole number varying from 1 to m, A defined as above 3/ an oligomer of urea having the following formula:

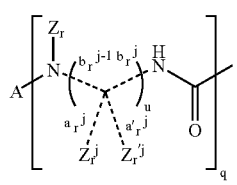

"u" is a whole number greater than or equal to 1, preferably 1 to 50, and particularly 1 to 10, "q" is a whole number greater than or equal to 1, preferably 1 to 50, and particularly 1 to 10, "j" is a whole parameter greater than or equal to 2 defined in the following manner: j always has whole values comprised from 2 to u+1, or "r" is a whole parameter greater than or equal to 1, always taking values comprised from 1 to q, "$a_r^j$ and $a'_r^j$", represented by a broken line, are covalent bonds which can be single (s) or double (d), "$b_r^j$ and $b_r^{j-1}$", represented by a broken line, are covalent bonds which can be single (s), double (d) or triple (t) provided that:

$b_q^1$ and $b_q^{u+1}$ are always single bonds (s)

if $b_r^j$=d, then $a_r^j$ and $a_r^{j+1}$=s; $a'_r^j$ and $a'_r^{j+1}$=Ø; $b_r^{j-1}$ and $b_r^{j+1}$=s if $b_r^j$=t, then $a_r^j$ and $a_r^{j+1}$=Ø; $a'_r^j$ and $a'_r^{j+1}$=Ø; $b_r^{j-1}$ and $b_r^{j+1}$=s if $a_r^j$=d, then $b_r^{j-1}$ and $b_r^j$=s certain of these bonds can also form a part of aromatic rings, A defined as above $Z_r$, $Z_r^j$, $Z'^j_r$ are defined independently as above for $R^1$, $R^i$, $R^{ti}$, the X group represents a group giving to the compound of formula I an activated carbamate structure, which X group comes from a compound selected particularly from phenols, if desired substituted by at least one nitro or at least one halogen, or hydroxylamine derivatives, and more particularly selected from the following compounds:

N-hydroxysuccinimide phenol pentafluorophenol pentachlorophenol p-nitrophenol 2,4-dinitrophenol 2,4,5-trichlorophenol 2,4-dichloro-6-nitrophenol hydroxy-1,2,3-benzotriazole 1-oxo-2-hydroxydihydrobenzotriazine (HODhbt)

7-aza-1-hydroxybenzotriazole (HOAt)

4-aza-1-hydroxybenzotriazole (4-HOAt)

imidazole tetrazole the compound of formula (III) having the following property:

if one or several asymmetric carbons are present in the formula (III), then their configuration can be independently either D (dextro) or L (levo), the groups $R^1$, $R^i$, $R^{ti}$ can also be defined on the basis of intramolecular cyclizations which are the following:

1/ cyclization between $R^i$ and $R^{ti}$

2/ cyclization between $R^i$ (or $R^{ti}$) and $R^{i+kc}$ (wherein kc is a whole positive number, preferably comprised between 1 and 3)

3/ cyclization between $R^1$ and $R^i$ (or $R^{ti}$) wherein preferably i=2, 3 or 4.

As an example of a pseudopeptide entering into the definition of Y, can be cited:

Boc-Ala-Ala-Gly-Ile-Gly-[$CH_2NH$]-Ile- (pseudo-hexapeptide containing a bond of the reduced type between Gly and Ile)

The invention also has for its object compounds of formula (III bis)

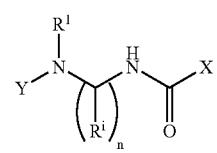
(III bis)

in which

"n" is a whole number greater than or equal to 1, preferably 1 to 10, preferably 1 to 4, "i" is a whole number varying from 2 to n+1,
the Y group can be or contain:
1/ a pseudopeptide (peptide containing one or several pseudopeptide linkages)

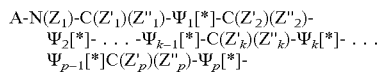

"p" is a whole number greater than or equal to 1, preferably 1 to 50, and particularly 1 to 10,
k is a whole number varying from 1 to p,
A is a group selected from:
hydrogen
oxycarbonyl (ROCO), preferably Boc (R=C(CH$_3$)$_3$), Fmoc (fluorenylmetoxycarboyl), benzyloxycarbonyl (R=CH$_2$Ph), allyloxycarbonyl (R=—CH$_2$CH=CH$_2$),
acyl (RCO), preferably R=CH$_3$, CH$_2$CH$_3$, CH(CH$_3$)$_2$, C(CH$_3$)$_3$, phenyl, benzyl, allyl, aryl,
alkyl (R), preferably R=trityl, CH$_3$, CH$_2$CH$_3$, CH(CH$_3$)$_2$, C(CH$_3$)$_3$, benzyl, allyl,
phenyl, particularly aryl,
urea (RNHCO), preferably R=CH$_3$, CH$_2$CH$_3$, CH(CH$_3$)$_2$, C(CH$_3$)$_3$, phenyl, benzyl, allyl,
phthalimide (R1=Ø)

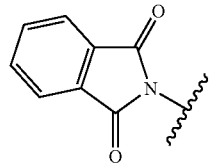

biotin
the group A can form with the nitrogen atom N with which it is contiguous, an "NH$_2^+$" entity
$Z_k$, $Z'_k$, and $Z''_k$ can each represent independently of each other
hydrogen,
the protected or unprotected side chain of an amino acid selected from proteinogenic and non-proteinogenic amino acids,
an (C1–C20) alkyl group, unsubstituted or substituted with one or several of the following substituents:
1/ —COOR$_b$
2/ —CONHR$_b$
3/ —COOH
4/ —OH, OR$_b$
5/ —NHR$_b$
6/ —NH$_2$
7/ —NH(CO)R$_b$
8/aryl, whose cyclic structure contains 5 to 20 carbon atoms
9/ halogen
10/ carbonyl of 1 to 10 carbon atoms
11/ nitrile
12/ guanidine
an aryl group whose cyclic structure contains 5 to 20 carbon atoms
a halogen
—OR$_b$
—COOR$_b$
—CONHR$_b$
—CONH$_2$
—CH$_2$COOR$_b$
—CH$_2$CONHR$_b$
—CH$_2$CONH$_2$ R$_b$ representing an allyl, benzyl, t-butyl, fluorenylmethyl, alkyl having 1 to 20 carbon atoms group, or an aryl group whose cyclic structure contains 5 to 20 carbon atoms,
-Ψ$_k$[*]—are independently either peptid links CO—NH, or linkages of different chemical nature selected particularly from the following list, which is not limiting:
Ψ$_k$[*]-=—CH(F$_k$)—; —CO—; —N(F$_k$)CO—; —CH(F$_k$)CO—; —CH(F$_k$)NHCO—; —N(F$_k$)—; —CON(F$_k$)—; —CH$_2$CH$_2$; —CH(F$_k$)=CH(F$_k$')—; —CH$_2$NH—; —NHCO—; —NHCONH—; —N(F$_k$)CON(F$_k$')—; —COCH$_2$—; —CH(OH)CH$_2$—; —CH(OH)CH$_2$NH—; —CH$_2$O—; —CH$_2$—NHCONH—; CH(F$_k$)NHCON(F$_k$')—; —CH$_2$—CONH—; CH(F$_k$)CONH—; —CH(F$_k$)CH(F$_k$')CONH—

Fk and Fk' representing, independently of each other hydrogen, the side chain protected or not of an amino acid selected from proteinogenic amino acids and non-proteinogenic amino acids, halogen, an alkyl group of 1 to 20 carbon atoms, or an aryl group whose cyclic structure contains 5 to 20 carbon atoms, 2/ an amino acid residue or an amino acid chain:

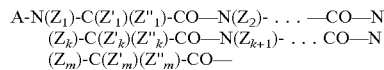

"m" is a whole number greater than or equal to 1, preferably 1 to 50, preferably 1 to 10,
"k" is a whole number varying from 1 to m,
A defined as above
3/ a GP group which can be:
a protective group selected from:
hydrogen
oxycarbonyl (GP=ROCO), preferably Boc (R=C(CH$_3$)$_3$), Fmoc (fluorenylmetoxycarbonyl), benzyloxycarbonyl (R=CH$_2$Ph), allyloxycarbonyl (R=—CH$_2$CH=CH$_2$),
acyl (GP=RCO), preferably R=CH$_3$, CH$_2$CH$_3$, CH(CH$_3$)$_2$, C(CH$_3$)$_3$, phenyl, benzyl, allyl, aryl,
alkyl (R), preferably R=trityl, CH$_3$, CH$_2$CH$_3$, CH(CH$_3$)$_2$, C(CH$_3$)$_3$, benzyl, allyl,
phenyl, particularly aryl,
urea (RNHCO), preferably R=CH$_3$, CH$_2$CH$_3$, CH(CH$_3$)$_2$, C(CH$_3$)$_3$, phenyl, benzyl, allyl,
phthalimide (R1=Ø)

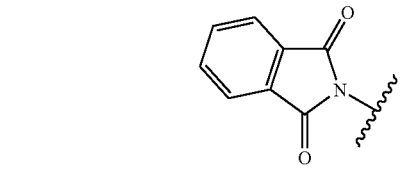

biotin
O$_2$ (corresponding to a nitro group as a masked amino form), R1=Ø,
the GP group which can also be such that the "GP-N" entity forms an "NH$_2^+$" entity,
the $R^1$, $R^i$ and R groups can each represent independently of each other:
hydrogen,
halogen,
the protected or unprotected side chain of an amino acid selected from natural or synthetic amino acids a (C1–C20) alkyl group unsubstituted or substituted with one or several of the following substituents:
1/ —COOR$_a$
2/ —CONHR$_a$
3/ —COOH
4/ —OH
5/ —OR$_a$
6/ —NHR$_a$
7/ —NH$_2$
8/ —NH(CO)R$_a$
9/ aryl, whose cyclic structure contains 5 to 20 carbon atoms
10/ halogen
11/ carbonyl
12/ nitrile
13/ guanidine
14/ nitro an aryl group whose cyclic structure contains 5 to 20 carbon atoms
an OR$_a$ group
an NH$_2$ group
an OH group
—COOR$_a$
—CONHR$_a$
—CONH$_2$
—CH$_2$COOR$_a$
—CH$_2$CONHR$_a$
—CH$_2$CONH$_2$ R$_a$ representing an allyl, benzyl, t-butyl, fluorenylmethyl, alkyl having 1 to 20 carbon atoms group, or an aryl group whose cyclic structure contains 5 to 20 carbon atoms,
  the X group represents a group giving to the compound of formula (III bis) the structure of an activated derivative of carbamic acid, which X group comes from a compound selected particularly from phenols, if desired substituted with at least one nitro or at least one halogen, or hydroxylamine derivatives, and more particularly selected from the following compounds:
N-hydroxysuccinimide
phenol
pentafluorophenol
pentachlorophenol
p-nitrophenol
2,4-dinitrophenol
2,4,5-trichlorophenol
2,4-dichloro-6-nitrophenol
hydroxy-1,2,3-benzotriazole
1-oxo-2-hydroxydihydrobenzotriazine (HODhbt)
7-aza-1-hydroxybenzotriazole (HOAt)
4-aza-1-hydroxybenzotriazole (4-HOAt)
imidazole
tetrazole
the compound of formula (III bis) having the following property:
  if one or several asymmetric carbons are present in the formula (III bis), then their configuration can be independently either D (dextor) or L (levo),
  the R$^1$ and R$^i$ groups can also be defined on the basis of intramolecular cyclizations which are as follows:
  1/ cyclization between R$^i$ and R$^{i+kc}$ (where kc is a whole positive number, preferably comprised between 1 to 3)
  2/ cyclization between R$^1$ and R$^i$ with preferably i=2, 3 or 4,
  provided that the compound of formula (III bis) is different from the following compounds in which:
  n=2, GP=Boc, R$^1$=isobutyl, R$^2$=R$^{i2}$=R$^3$=R$^{i3}$=H, X=4-nitrophenol, n=2, GP=Boc, R$^1$=benzyl, R$^2$=R$^{i2}$=R$^3$=R$^{i3}$=H, X=4-nitrophenol,
n=2, GP=Boc, R$^1$=CH$_2$-p-C$_6$H$_4$Ot-Bu, R$^2$=R$^{i2}$=R$^3$=R$^{i3}$=H, X=4-nitrophenol,
n=2, GP=Boc, R$^1$=H, R$^2$=R$^{i2}$=R$^3$=R$^{i3}$=H, X=4-nitrophenol.

The invention also has for its object compounds of the formula (I bis)

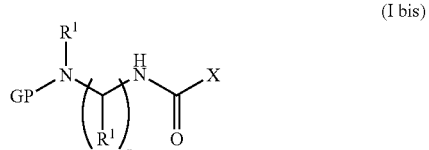

(I bis)

in which n, i, GP, X, R$^1$ and R$^i$ have the meanings mentioned above, in connection with formula (III bis).

A preferred group of compounds of formula (III bis) is constituted by those in which 1 n≦4, X is as defined above in connection with formula (III bis) and is particularly derived from p-nitrophenol, N-hydroxysuccinimide, pentafluorophenol, hydroxy-1,2,3benzotriazole or imidazole, A is an oxycarbonyl or acyl group as defined above in connection with formula (III bis), and particularly the compounds in which q and m are comprised from 1 to 10, and preferably equal from 1 or 2, and more particularly those in which A-Boc and Fmoc, and in particular the compounds having the following formulas:

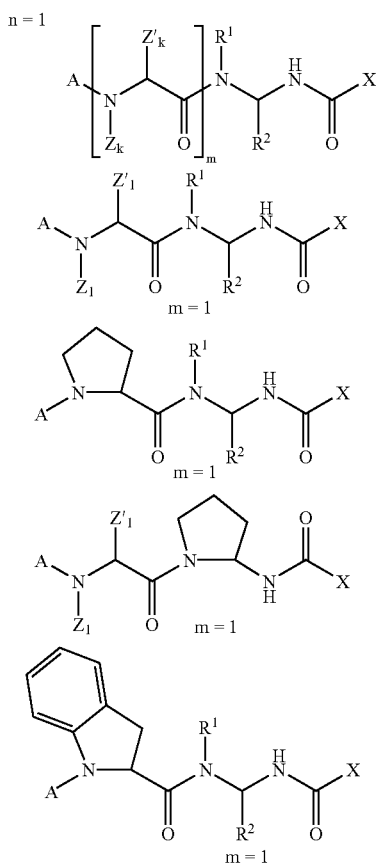

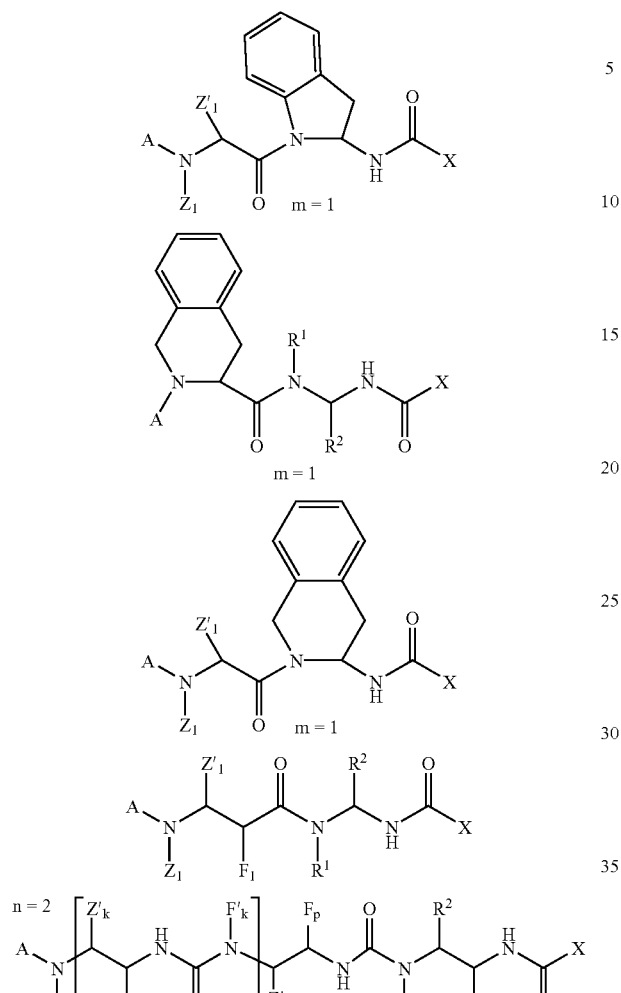
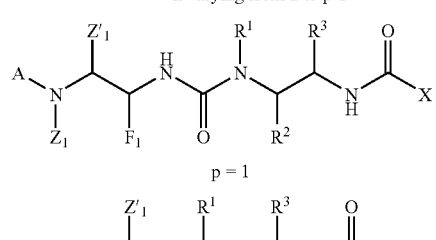
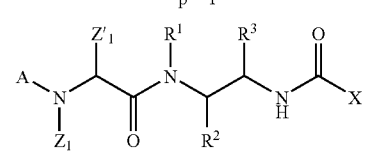
and more particularly the compounds of the following formulas:
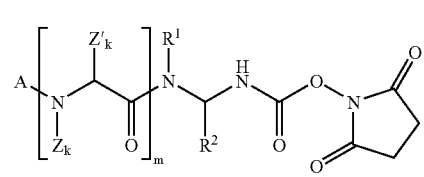
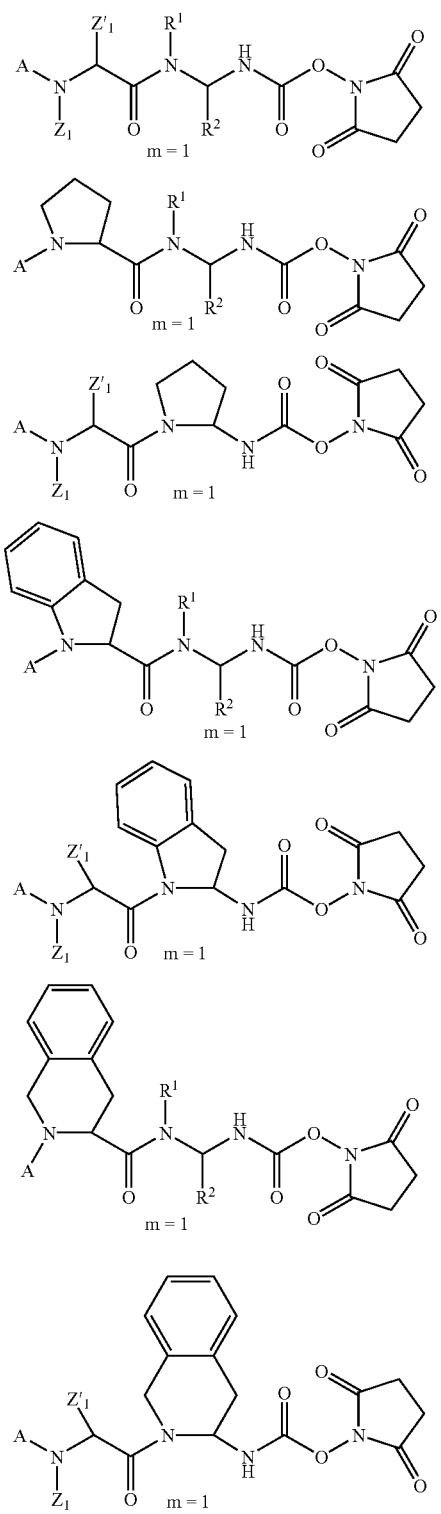
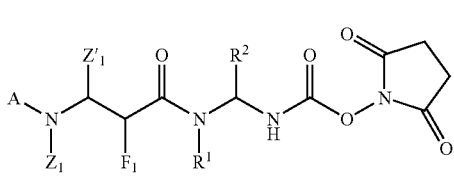

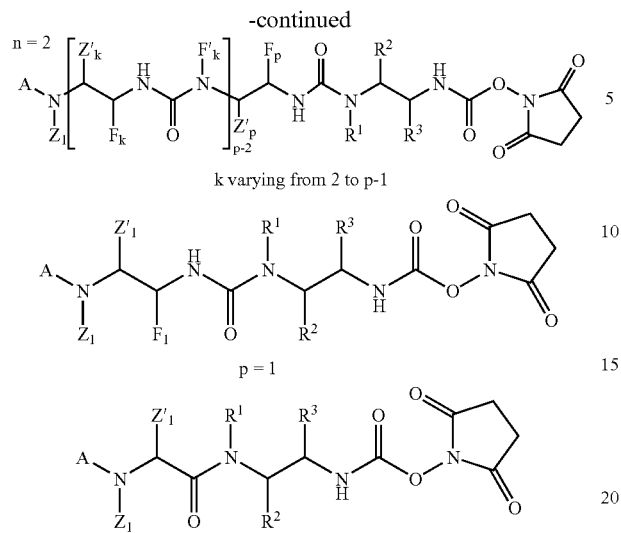

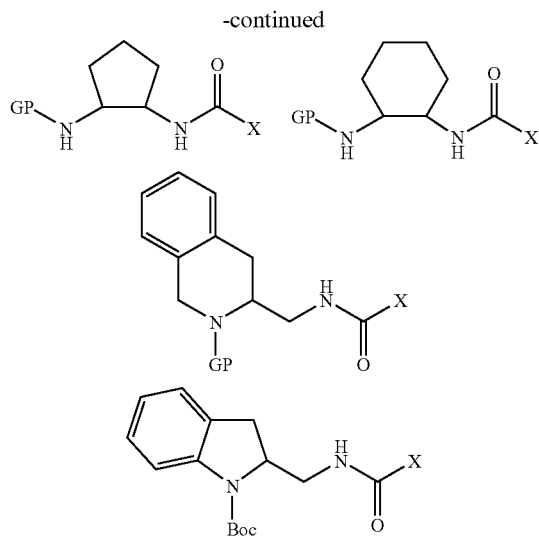

A preferred group of compounds of furmula (I bis) is constituted by those in which $1 \leq n \leq 4$, X is as defined above with respect to formula (III bis) and is particularly derived from p-nitrophenol, N-hydroxysuccinimide, pentafluorophenol, hydroxy-1,2,3-benzotriazole or imidazole, GP is an oxycarbonyl or acyl group as defined above in connection with formula (III bis), and particular those in which GP is preferably Boc, Fmoc, and in particular the compounds having the following formulas:

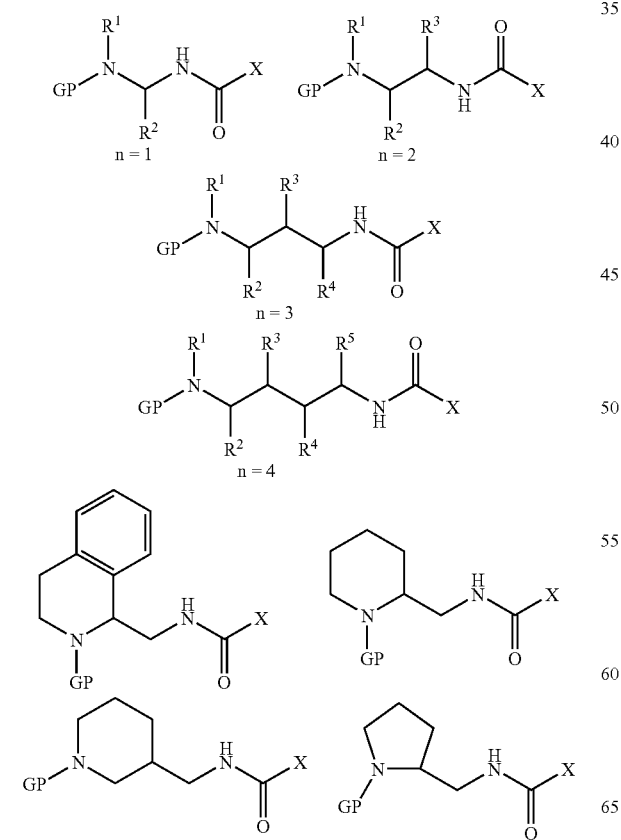

and more particularly the compounds having the following formulas:

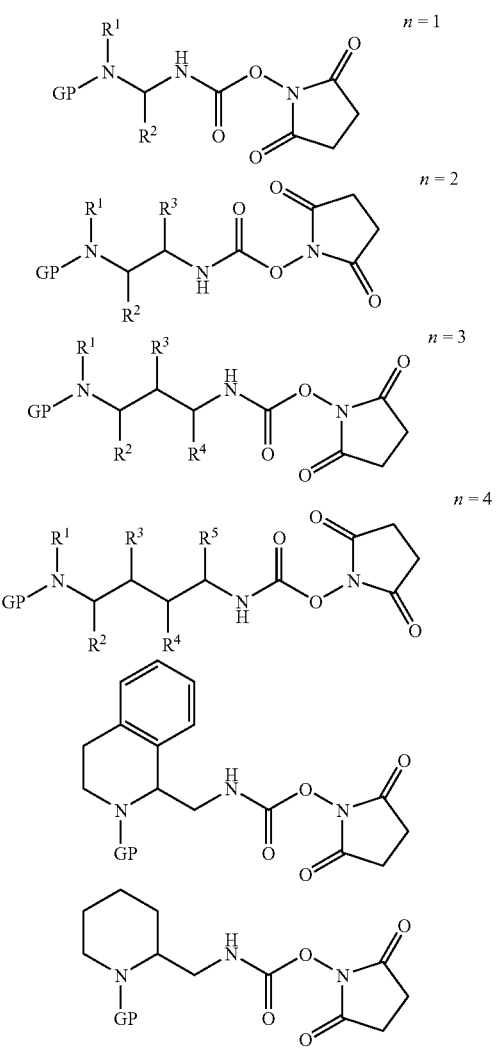

-continued

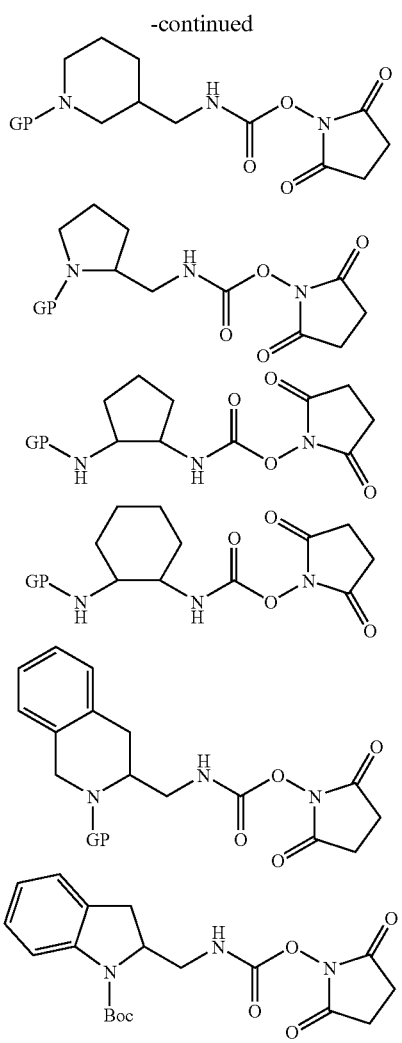

The compounds of formulas (III) and (III bis) are activated carbamates analogous to the compounds of formulas (I) and (I bis) in which the protective group is replaced for example by an amino acid chain, a pseudopeptide, or an oligomer of urea. They can be obtained from corresponding isocyanates of formula (IV) defined hereafter.

The compounds of formulas (I) and (I bis) are activated carbamates derived from N-protected amino acids of formula IX defined hereafter and which can be obtained from isocyanates of formula (II) defined hereafter.

The invention also relates to compounds of formula (IV)

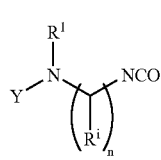
(IV)

in which

"n" is a whole number greater than or equal to 1, preferably 1 to 10, preferably 1 to 4, "i" is a whole number varying from 2 to n+1, the Y group can be or contain:

1/ a pseudopeptide (peptide containing one or several pseudopeptide linkages)

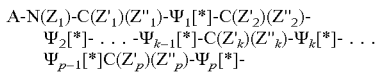

"p" is a whole number greater than or equal to 1 preferably 1 to 50, preferably 1 to 10, "k" is a whole number varying from 1 to p, or A is a group selected from:

hydrogen oxycarbonyl (ROCO), preferably Boc (R=C(CH$_3$)$_3$), Fmoc (fluorenylmetoxycarbonyl), benzyloxycarbonyl (R=CH$_2$Ph), allyloxycarbonyl (R=—CH$_2$CH=CH$_2$), acyl (RCO), preferably R=CH$_3$, CH$_2$CH$_3$, CH(CH$_3$)$_2$, C(CH$_3$)$_3$, phenyl, benzyl, allyl, aryl, alkyl (R), preferably R=trityl, CH$_3$, CH$_2$CH$_3$, CH(CH$_3$)$_2$, C(CH$_3$)$_3$, benzyl, allyl, phenyl, particularly aryl, urea (RNHCO), preferably R=CH$_3$, CH$_2$CH$_3$, CH(CH$_3$)$_2$, C(CH$_3$)$_3$, phenyl, benzyl, allyl, phthalimide (R1=Ø)

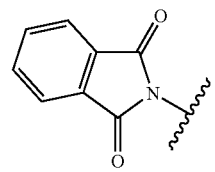

biotin the group A can form with the nitrogen atom N to which it is contiguous an "NH$_2^+$" entity $Z_k$, $Z'_k$ and $Z''_k$ can each represent or independently:

hydrogen, the protected or unprotected side chain of an amino acid selected from proteinogenic and non-proteinogenic amino acids, a (C1–C20) alkyl group, substituted or unsubstituted with one or several substituents from the following:

1/ —COOR$_b$

2/ —CONHR$_b$

3/ —COOH

4/ —OH, OR$_b$

5/ —NHR$_b$

6/ —NH$_2$

7/ —NH(CO)R$_b$

8/ aryl whose cyclic structure contains 5 to 20 carbon atoms

9/ halogen

10/ carbonyl of 1 to 10 carbon atoms

11/ nitrile

12/ guanidine an aryl group whose cyclic structure contains 5 to 20 halogen atoms —OR$_b$ —COOR$_b$ —CONHR$_b$

—CONH$_2$

—CH$_2$COOR$_b$

—CH$_2$CONHR$_b$

—CH$_2$CONH$_2$ $R_b$ representing an allyl, benzyl, t-butyl, fluorenylmethyl, alkyl having 1 to 20 carbon atoms group, or an aryl group whose cyclic structure contains 5 to 20 carbon atoms, -$\Psi_k$[*]- are independently either peptide linkages CO—NH, or linkages of different chemical nature selected particularly from the following list:

$\Psi_k$[*]-=—CH($F_k$)—; —CO—; —N($F_k$)CO—; —CH($F_k$)CO—; —CH($F_k$)NHCO—; —N($F_k$)—; —CON($F_k$)—; —CH$_2$CH$_2$; —CH($F_k$)=CH($F_k'$)—; —CH$_2$NH—; —NHCO—; —NHCONH—; —N($F_k$)CON($F_k'$)—; —COCH$_2$—; —CH(OH)CH$_2$—; —CH(OH)CH$_2$NH—; —CH$_2$O—; —CH$_2$—NHCONH—; CH($F_k$)NHCON($F_k'$)—; —CH$_2$—CONH—; CH($F_k$)CONH—; —CH($F_k$)CH($F_k'$)CONH—

$F_k$ and $F_k'$ representing, independently from each other, hydrogen, the protected or unprotected side chain of an amino acid selected from proteinogenic and, non-proteinogenic amino acids, halogen, an alkyl group of 1 to 20 carbon atoms, or an aryl group whose cyclic structure contains 5 to 20 carbon atoms, 2/ an amino acid residue or an amino acid chain:

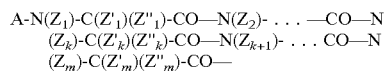

A-N($Z_1$)-C($Z'_1$)($Z''_1$)-CO—N($Z_2$)- . . . —CO—N($Z_k$)-C($Z'_k$)($Z''_k$)-CO—N($Z_{k+1}$)- . . . CO—N($Z_m$)-C($Z'_m$)($Z''_m$)-CO—

"m" is a whole number greater than or equal to 1, preferably 1 to 50, preferably 1 to 10, "k" is a whole number varying from 1 to m, A defined as above, 3/ A GP group which can be:

a protective group selected from:

hydrogen oxycarbonyl (GP=ROCO), preferably Boc (R=C(CH$_3$)$_3$), Fmoc (fluorenylmethoxycarbonyl), benzyloxycarbonyl (R=CH$_2$Ph), allyloxycarbonyl (R=—CH$_2$CH=CH$_2$), acyl (GP=RCO), preferably R=CH$_3$, CH$_2$CH$_3$, CH(CH$_3$)$_2$, C(CH$_3$)$_3$, phenyl, benzyl, allyl, aryl, alkyl (R), preferably R=trityl, CH$_3$, CH$_2$CH$_3$, CH(CH$_3$)$_2$, C(CH$_3$)$_3$, benzyl, allyl, phenyl, particularly aryl, urea (GP=RNHCO), preferably R=CH$_3$, CH$_2$CH$_3$, CH(CH$_3$)$_2$, C(CH$_3$)$_3$, phenyl, benzyl, allyl, phthalimide ($R^1$=Ø)

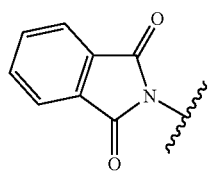

biotin $O_2$ (corresponds to a nitro group as the masked form of the amine), $R^1$=Ø the GP group which can also be such that the GP-N entity forms an "NH$_2^+$" entity the $R^1$, $R^i$ and R groups can each represent independently of each other:

hydrogen halogen the protected or unprotected side chain of an amino acid selected from natural or synthetic amino acids a (C1–C20) alkyl group unsubstituted or substituted with one or several substituents selected from:

1/ —COOR$_a$
2/ —CONHR$_a$
3/ —COOH
4/ —OH
5/ —OR$_a$
6/ —NHR$_a$
7/ —NH$_2$
8/ —NH(CO)R$_a$
9/ aryl, whose cyclic structure contains 5 to 20 carbon atoms
10/ halogen
11/ carbonyl of 1 to 10 carbon atoms
12/ nitrile
13/ guanidine
14/ nitro an aryl group, whose cyclic structure contains 5 to 20 carbon atoms an OR$_a$ group an NH$_2$ group an OH group —COOR$_a$ —CONHR$_a$

—CONH$_2$

—CH$_2$COOR$_a$

—CH$_2$CONHR$_a$

—CH$_2$CONH$_2$ $R_a$ representing an allyl, benzyl, t-butyl, fluorenylmethyl, alkyl having 1 to 20 carbon atoms group, or an aryl group whose cyclic structure contains 5 to 20 carbon atoms, the compound of formula (IV) having the following property:

if one or several asymmetric carbons are present in the formula (IV), then their configuration can be independently either D (dextro) or L (levo), the groups $R^1$ and $R^1$ can also be defined on the basis of intramolecular cyclizations which are the following:

1/ cyclization between $R^i$ and $R^{i+kc}$ (where kc is a positive integer, preferably comprised between 1 to 3)

2/ cyclization between $R^1$ and $R^i$ wherein preferably i=2, 3 or 4.

provided that the compound of formula (IV) be different from the compounds in which:

n=1, GP=Boc or benzyloxycarbonyl, R1=Ø n=2, GP=phtalimide, $R_1$=Ø, $R_3$=benzyle, $R'_2$=$R_2$=$R'_3$=H n=2, GP=phtalimide, $R_1$=Ø, $R_3$=methyle, $R'_2$=$R_2$=$R'_3$=H n=2, GP=phtalimide, $R_1$=Ø, $R_3$=H, $R'_2$=$R_2$=$R'_3$=H n=2, GP=phtalimide, $R_1$=Ø, $R_3$=CH$_2$i-Pr, $R'_2$=$R_2$=$R'_3$=H n=2, GP=phtalimide, $R_1$=Ø, $R_3$=CH$_2$COOt-Bu, $R'_2$=$R_2$=$R'_3$=H n=2, GP=phtalimide, $R_1$=Ø, $R_3$=CH$_2$CH$_2$CH$_2$CH$_2$NHBoc, $R'_2$=$R_2$=$R'_3$=H n=2, GP=phtalimide, $R_1$=Ø, $R_3$=CH$_2$ CH$_2$ CH$_2$NHCNH(N-Mtr), $R'_2$=$R_2$=$R'_3$=H, (Mtr=4-methoxy-2,3,6-trimethyl-benzene-sulphonyl)

n=2, GP=Boc, $R_1$=benzyl, $R_2$=$R'_2$=$R_3$=$R'_3$=H n=2, GP=Boc, $R_1$=i-Bu, $R_2$=$R'_2$=$R_3$=$R'_3$=H n=2, GP=Boc, $R_1$=H, $R_2$=$R'_2$=$R_3$=$R'_3$=H The invention also has for its object compounds of the formula (II)

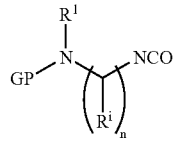
(II)

in which n, i, GP, $R^1$ and $R^i$ have the meanings mentioned above in connection with formula (IV).

A group of preferred compounds of formula (IV) are those in which $1 \leq n \leq 4$, A is an oxycarbonyl or acyl group as defined above in connection with formula (IV), and particularly the following compounds for which p and m are comprised from 1 to 10 and preferably equal to 1 or 2, and particularly those for which A=Boc and Fmoc,

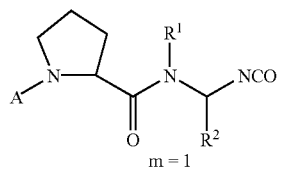
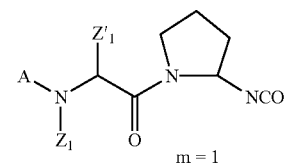

m = 1
A different from Boc (tertbutoxycarbonyle) and benzyloxycarbonyle m = 1

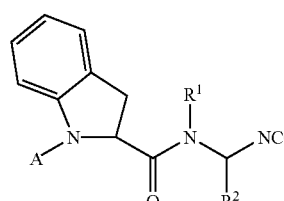

m = 1   m = 1

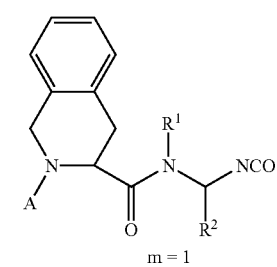
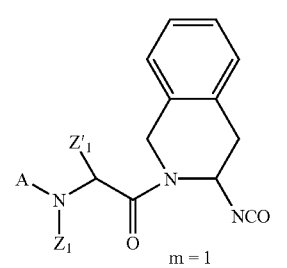

m = 1   m = 1

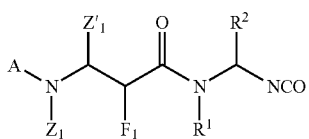

n = 2
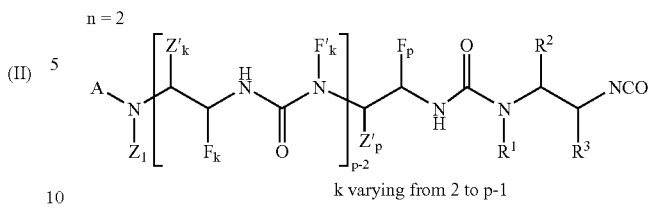
k varying from 2 to p-1

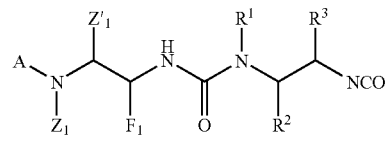
p = 1

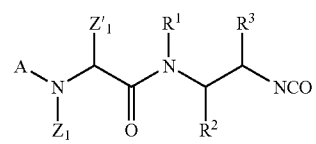

A preferred group of compounds of formula (II) are those in which $1 \leq n \leq 4$, GP is an oxycarbonyl or acyl group as defined above with respect to formula (IV), and particularly the following compounds, in particular those in which GP=Boc and Fmoc,

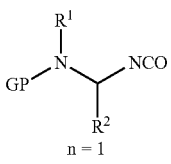
n = 1

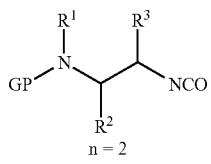
n = 2

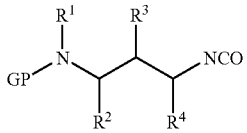
n = 3

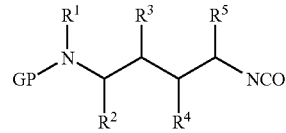
n = 4

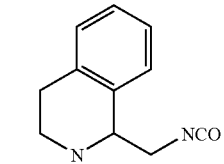

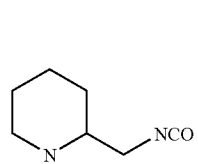

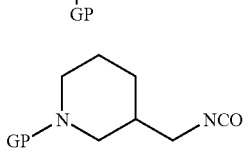

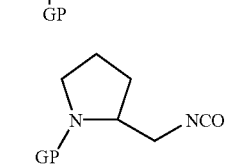

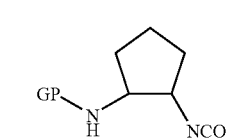

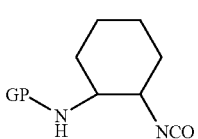

-continued

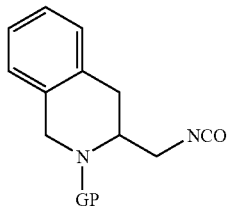
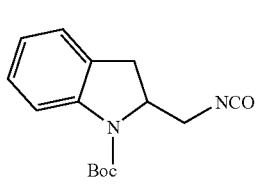

The isocyanates of formula (IV) can be used as precursors for the synthesis of the compounds of formula (III) and (III bis) and can be obtained from compounds of the formula (X) defined hereinafter.

The isocyanates of formula (II) are the precursors used in the synthesis of compounds of formulas (I) and (I bis) and can be obtained from N-protected amino acid derivatives of formula (IX) defined hereafter.

The invention also relates to compounds of the formula (V)

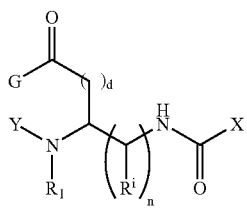

(V)

in which
"n" is a whole number greater than or equal to 1, particularly from 1 to 4 and preferably from 1 to 2,
"d" is a whole number comprised between 0 and 4, preferably equaling 0 or 1,
"i" is a number varying from 2 to n+1,
the Y group can be or contain:
1/ a pseudopeptide (peptide containing one or several pseudopeptide linkages)

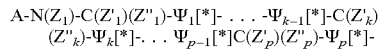

"p" is a whole number greater than or equal to 1, preferably from 1 to 50, preferably from 1 to 10,
"k" is a whole number varying from 1 to m,
A is a group selected from:
hydrogen
oxycarbonyl (ROCO), preferably Boc (R=C(CH$_3$)$_3$), Fmoc (fluorenylmetoxycarboyl), benzyloxycarbonyl (R=CH$_2$Ph), allyloxycarbonyl (R=—CH$_2$CH=CH$_2$),
acyl (RCO), preferably R=CH$_3$, CH$_2$CH$_3$, CH(CH$_3$)$_2$, C(CH$_3$)$_3$, phenyl, benzyl, allyl, aryl,
alkyl (R), preferably R=trityl, CH$_3$, CH$_2$CH$_3$, CH(CH$_3$)$_2$, C(CH$_3$)$_3$, benzyl, allyl,
phenyl, particularly aryl,
urea (RNHCO), preferably R=CH$_3$, CH$_2$CH$_3$, CH(CH$_3$)$_2$, C(CH$_3$)$_3$, phenyl, benzyl, allyl,
phthalimide (R$^1$=Ø)

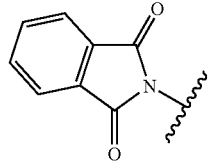

biotin
the group A can form with the nitrogen atom N with which it is contiguous an "NH$_2$$^+$" entity $Z_k$, $Z'_k$, and $Z''_k$ can each represent and independently of one another:
hydrogen,
the protected or unprotected side chain of an amino acid selected from proteinogenic and non-proteinogenic amino acids,
a (C1–C20) alkyl group, unsubstituted or substituted with one or several substituents from the following:
1/ —COOR$_b$
2/ —CONHR$_b$
3/ —COOH
4/ —OH, OR$_b$
5/ —NHR$_b$
6/ —NH$_2$
7/ —NH(CO)R$_b$
8/ aryl, whose cyclic structure contains 5 to 20 carbon atoms
9/ halogen
10/ carbonyl of 1 to 10 carbon atoms
11/ nitrile
12/ guanidine
an aryl group, whose cyclic structure contains 5 to 20 carbon atoms
a halogen
—OR$_b$
—COOR$_b$
—CONHR$_b$
—CONH$_2$
—CH$_2$COOR$_b$
—CH$_2$CONHR$_b$
—CH$_2$CONH$_2$
R$_b$ representing an allyl, benzyl, t-butyl, fluorenylmethyl, alkyl having 1 to 20 carbon atoms group, or an aryl group whose cyclic structure contains 5 to 20 carbon atoms,
-Ψ$_k$[*]- are independently either CO—NH peptide linkages or linkages of different chemical nature selected particularly from the following list:
Ψ$_k$[*]-=—CH(F$_k$)—; —CO—; —N(F$_k$)CO—; —CH(F$_k$)CO—; —CH(F$_k$)NHCO—; —N(F$_k$)—; —CON(F$_k$)—; —CH$_2$CH$_2$; —CH(F$_k$)=CH(F$_k$')—; —CH$_2$NH—; —NHCO—; —NHCONH—; —N(F$_k$)CON(F$_k$')—; —COCH$_2$—; —CH(OH)CH$_2$—; —CH(OH)CH$_2$NH—; —CH$_2$O—; —CH$_2$—NHCONH—; CH(F$_k$)NHCON (F$_k$')—; —CH$_2$—CONH—; CH(F$_k$)CONH—; —CH(F$_k$)CH(F$_k$')CONH—
Fk and Fk' representing, independently of each other, hydrogen, the protected or unprotected side chain of an amino acid selected from proteinogenic and non-proteinogenic amino acids, halogen, an alkyl of 1 to 20 carbon atoms, or an aryl group whose cyclic structure contains 5 to 20 carbon atoms,
2/ an amino acid residue or an amino acid chain:

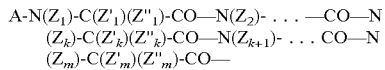

"m" is a whole number greater than or equal to 1, preferably 1 to 50, preferably 1 to 10,
"k" is a whole number varying from 1 to m,
A defined as above,
the R$^1$, R$^i$, and R groups can each represent independently of each other:
hydrogen,
halogen,
the protected or unprotected side chain of an amino acid selected from natural or synthetic amino acids, a (C1–C20) alkyl group, unsubstituted or substituted with one or several substituents from the following:
1/ —COOR$_a$
2/ —CONHR$_a$
3/ —COOH
4/ —OH
5/ —OR$_a$
6/ —NHR$_a$
7/ —NH$_2$
8/ —NH(CO)R$_a$
9/ aryl
10/ halogen
11/ carbonyl of 1 to 10 carbon atoms
12/ nitrile
13/ guanidine
14/ nitro
an aryl group, whose cyclic structure contains 5 to 20 carbon atoms
an OR$_a$ group
an NH$_2$ group
an OH group
—COOR$_a$
—CONHR$_a$
—CONH$_2$
—CH$_2$COOR$_a$
—CH$_2$CONHR$_a$
—CH$_2$CONH$_2$ R$_a$ representing an allyl, benzyl, t-butyl, fluorenylmethyl, alkyl having 1 to 20 carbon atoms group, or an aryl group whose cyclic structure contains 5 to 20 carbon atoms, the G group can be or contain:

A/ an amino acid residue or an amino acid residue chain:

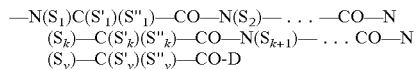

"v" is a whole number greater than or equal to 1, preferably 1 to 50, preferably 1 to 10 with preferably v>3 and v>5, D can be:
—NH$_2$
—NHCOR$_c$
—NHR$_c$
—NR$_c$R$_d$
—N(R$_c$)CON(R$_d$)
—OH
—OR$_c$ R$_c$ and R$_d$ represent independently of each other an allyl, benzyl, t-butyl, fluorenylmethyl, alkyl having 1 to 20 carbon atoms group, or an aryl group whose cyclic structure contains 5 to 20 carbon atoms, S$_k$, S'$_k$ and S"$_k$ can each represent independently:
hydrogen,
the protected or unprotected side chain of an amino acid selected from proteinogenic and non-proteinogenic amino acids,
a (C1–C20) alkyl group, unsubstituted or substituted with one or several substituents from the following:
1/ —COOR$_e$
2/ —CONHR$_e$
3/ —COOH
4/ —OH, OR$_e$
5/ —NHR$_e$
6/ —NH$_2$
7/ —NH(CO)R$_e$
8/ aryl whose cyclic structure contains 5 to 20 carbon atoms
9/ halogen
10/ carbonyl
11/ nitrile
12/ guanidine
an aryl group whose structure contains 5 to 20 carbon atoms
an OR$_e$ group
an NH$_2$ group
an OH group
a halogen R$_e$ representing an allyl, benzyl, t-butyl, fluorenylmethyl, alkyl having 1 to 20 carbon atoms group, or an aryl group whose cyclic structure contains 5 to 20 carbon atoms.

B/ a radical selected from:
NH$_2$
O-benzyl
O-allyl
O-methyl
O-ethyl
O-terbutyl the X group represents a group giving to the compound of formula (V) an activated molecular structure adapted to react with alcohols or amines to form carbamic acid derivatives or ureas, and is particularly derived from a compound selected from phenols, if desired substituted with nitro or a halogen or hydroxylamine derivatives and more particularly selected from:

N-hydroxysuccinimide
phenol
pentafluorophenol
pentachlorophenol
p-nitrophenol
2,4-dinitrophenol
2,4,5-trichlorophenol
2,4-dichloro-6-nitrophenol
hydroxy-1,2,3-benzotriazole
1-oxo-2-hydroxydihydrobenzotriazine (HODhbt)
7-aza-1-hydroxybenzotriazole (HOAt)
4-aza-1-hydroxybenzotriazole (4-HOAt)
imidazole
tetrazole the compounds of formula (V) having the following property:

if one or several asymmetric carbons are present in formula (V), then their configuration can be in independent manner either D (dextro) or L (levo), the groups R$^1$ and R$^i$ groups can also be defined on the basis of intramolecular cyclizations which are the following:

1/ cyclization between R$^1$ and R$^{i+kc}$ (in which kc is a positive whole number, preferably comprised between 1 and 3)

2/ cyclization between R$^1$ and R$^i$ wherein preferably i=2, 3 or 4, and more particularly the compounds corresponding to formula (V) in which $1 \leq n \leq 4$, d=0 or 1, X=N-hydroxysuccinimide, A is an oxycarbonyl or acyl group, and particularly the compounds in which p, m and v are comprised from 1 to 10 and preferably equal to 1 or 2, and preferably those in which A=Boc and Fmoc, and particularly the compounds of the following formulas:

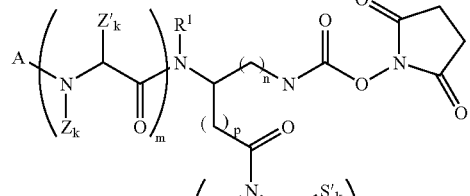

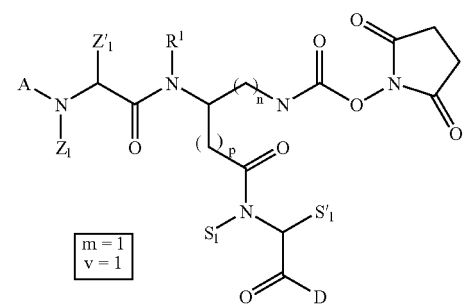

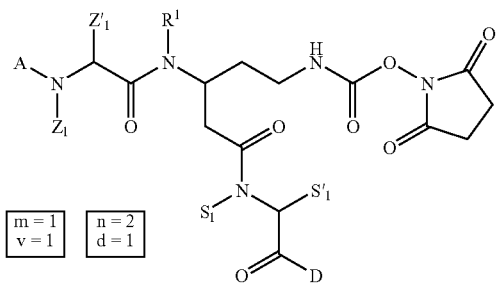

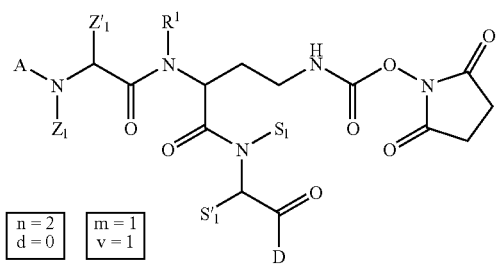

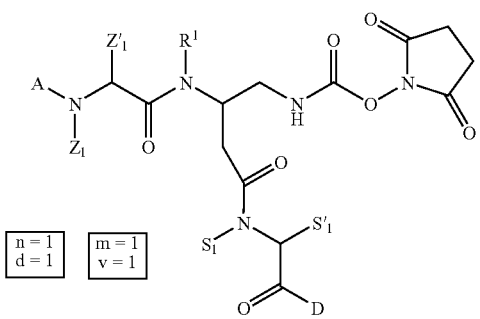

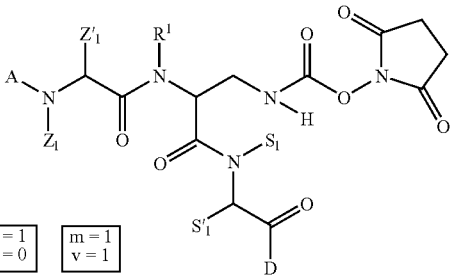

The compounds of formula (V) are activated carbamates analogous to compounds of formulas (I) and (I bis) in which the activated carbamate is introduced into the side chain of a protective amino acid or a peptide, a pseudopeptide or else an oligomer of urea.

The invention also relates to compounds of formula (Vbis)

(Vbis)

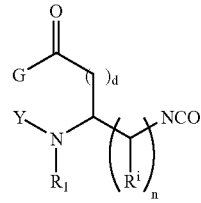

in which
"n" is a whole number greater than or equal to 1, comprised particularly by 1 to 4, and preferably 1 to 2,
"d" is a whole number comprised from 0 to 4, preferably equaling 0 or 1,
"i" is a whole parameter greater than or equal to 2 defined in the following manner: i takes all the whole values comprised from 2 to n+1,
the Y group can be or contain:
1/ a pseudopeptide (peptide containing one or several pseudopeptide linkages)

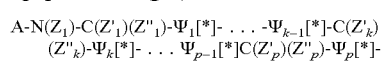

"p" is a whole number greater than or equal to 1, preferably from 1 to 50, preferably from 1 to 10,
"k" is a whole number varying from 1 to p,
A is a group selected from:
hydrogen
oxycarbonyl (ROCO), preferably Boc ($R=C(CH_3)_3$), Fmoc (fluorenylmetoxycarboyl), benzyloxycarbonyl ($R=CH_2Ph$), allyloxycarbonyl ($R=\!-\!CH_2CH\!=\!CH_2$),
acyl (RCO), preferably $R=CH_3$, $CH_2CH_3$, $CH(CH_3)_2$, $C(CH_3)_3$, phenyl, benzyl, allyl, aryl,
alkyl (R), preferably R=trityl, $CH_3$, $CH_2CH_3$, $CH(CH_3)_2$, $C(CH_3)_3$, benzyl, allyl,
phenyl, particularly aryl,
urea (RNHCO), preferably $R=CH_3$, $CH_2CH_3$, $CH(CH_3)_2$, $C(CH_3)_3$, phenyl, benzyl, allyl,
phthalimide ($R^1=\emptyset$)

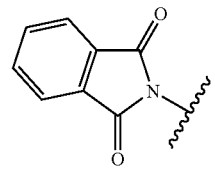

biotin the A group can form with the nitrogen atom N to which it is contiguous an "$NH_2^+$" entity, or $Z_k$, $Z'_k$, and $Z''_k$ can each represent and independently of each other:

hydrogen, the protected or unprotected side chain of an amino acid selected from proteinogenic and non-proteinogenic amino acids, a (C1–C20) alkyl group, unsubstituted or substituted with one or several substituents from the following:

1/ —$COOR_b$
2/ —$CONHR_b$
3/ —COOH
4/ —OH, $OR_b$
5/ —$NHR_b$
6/ —$NH_2$
7/ —$NH(CO)R_b$
8/ aryl, whose cyclic structure contains 5 to 20 carbon atoms
9/ halogen
10/ carbonyl
11/ nitrile
12/ guanidine
an aryl group whose cyclic structure contains 5 to 20 carbon atoms
a halogen
—$OR_b$
—$COOR_b$
—$CONHR_b$
—$CONH_2$
—$CH_2COOR_b$
—$CH_2CONHR_b$
—$CH_2CONH_2$ $R_b$ representing an allyl, benzyl, t-butyl, fluorenylmethyl, alkyl having 1 to 20 carbon atoms group, or an aryl group whose cyclic structure contains 5 to 20 carbon atoms, -$\Psi_k[*]$- are independently either CO—NH peptide linkages or linkages of different chemical natures selected particularly from the following list:

$\Psi_k[*]$-=—$CH(F_k)$—; —CO—; —$N(F_k)CO$—; —$CH(F_k)CO$—; —$CH(F_k)NHCO$—; —$N(F_k)$—; —$CON(F_k)$—; —$CH_2CH_2$; —$CH(F_k)$=$CH(F_k')$—; —$CH_2NH$—; —NHCO—; —NHCONH—; —$N(F_k)CON(F_k')$—; —$COCH_2$—; —$CH(OH)CH_2$—; —$CH(OH)CH_2NH$—; —$CH_2O$—; —$CH_2$—NHCONH—; $CH(F_k)NHCON(F_k')$—; —$CH_2$—CONH—; $CH(F_k)CONH$—; —$CH(F_k)CH(F_k')CONH$—

$F_k$ and $F_k'$ representing, independently of each other, hydrogen, the protected or unprotected side chain of an amino acid selected from proteinogenic and non proteinogenic amino acids, halogen, an alkyl group of 1 to 20 carbon atoms, or an aryl group whose cyclic structure contains 5 to 20 carbon atoms, 2/ an amino acid residue or an amino acid chain:

A-N($Z_1$)-C($Z'_1$)($Z''_1$)-CO—N($Z_2$)- . . . -CO—N($Z_k$)-C($Z'_k$)($Z''_k$)-CO—N($Z_{k+1}$)- . . . CO—N($Z_m$)-C($Z'_m$)($Z''_m$)-CO—

"m" is a whole number greater than or equal to 1, preferably 1 to 50, preferably 1 to 10, "k" is a whole number varying from 1 to m, A defined as above the $R^1$, $R^i$ and R groups can each represent independently of each other:

hydrogen, halogen, the protected or unprotected side chain of an amino acid selected from natural or synthetic amino acids, a (C1–C20) alkyl group unsubstituted or substituted with one or several substituents from the following:

1/ —$COOR_a$
2/ —$CONHR_a$
3/ —COOH
4/ —OH
5/ —$OR_a$
6/ —$NHR_a$
7/ —$NH_2$
8/ —$NH(CO)R_a$
9/ aryl, whose cyclic structure contains 5 to 20 carbon atoms
10/ halogen
11/ carbonyl of 1 to 10 carbon atoms
12/ nitrile
13/ guanidine
14/ nitro
an aryl group whose cyclic structure contains 5 to 20 carbon atoms
an $OR_a$ group
an $NH_2$ group
an OH group
—$COOR_a$
—$CONHR_a$
—$CONH_2$
—$CH_2COOR_a$
—$CH_2CONHR_a$
—$CH_2CONH_2$ $R_a$ representing an allyl, benzyl, t-butyl, fluorenylmethyl, alkyl having 1 to 20 carbon atoms group, or an aryl group whose cyclic structure contains 5 to 20 carbon atoms, the group G can be or contain A/ an amino acid residue or a chain of amino acid residues:

—N($S_1$)C($S'_1$)($S''_1$)—CO—N($S_2$)— . . . —CO—N($S_k$)—C($S'_k$)($S''_k$)—CO—N($S_{k+1}$)— . . . CO—N($S_v$)—C($S'_v$)($S''_v$)—CO-D-

"v" is a whole number greater than or equal to 1, preferably 1 to 50, preferably 1 to 10 and preferably v>3 and v>5, "k" is a whole number varying from 1 to v, preferably 1 to 50, D can be:

—$NH_2$
—NHCOR
—$NHR_c$
—$NR_cR_d$
—N ($R_c$) CON ($R_d$)
—OH
—$OR_c$ $R_c$ and $R_d$ represent independently of each other an allyl, benzyl, t-butyl, fluorenylmethyl, alkyl having 1 to 20 carbon atoms group, or an aryl group whose cyclic structure contains 5 to 20 carbon atoms, $S_k$, $S'_k$ and $S''_k$ can each represent independently of each other:

hydrogen, the protected or unprotected side chain of an amino acid selected from proteinogenic and non-proteinogenic amino acids, a (C1–C20) alkyl group unsubstituted or substituted with one or several of the following substituents:

1/ —$COOR_e$
2/ —$CONHR_e$

3/ —COOH
4/ —OH
5/ —NHR$_e$
6/ —NH$_2$
7/ —NH(CO)R$_e$
8/ aryl, whose cyclic structure contains 5 to 20 carbon atoms
9/ halogen
10/ carbonyl
11/ nitrile
12/ guanidine
an aryl group, whose cyclic structure contains 5 to 20 carbon atoms
an OR$_e$ group
an NH$_2$ group
an OH group
a halogen
R$_e$ representing an allyl, benzyl, t-butyl, fluorenylmethyl, alkyl having 1 to 20 carbon atoms group, or an aryl group whose cyclic structure contains 5 to 20 carbon atoms
B/ a radical selected from:
NH$_2$
O-benzyl
O-allyl
O-methyl
O-ethyl
O-terbutyl
the compounds of formula (Vbis) having the following property:
if one or several asymmetric carbon atoms are present in formula (V), then their configuration can be independently of each other either D (dextro) or L (levo),
the groups R$^1$ and R$^i$ can also be defined on the basis of intramolecular cyclizations as follows:
1/ cyclization between R$^1$ and R$^{i+kc}$ (wherein kc is a positive whole number, preferably comprised between 1 and 3)
2/ cyclization between R$^1$ and R$^i$ wherein preferably i=2, 3 or 4,
and more particularly the compounds responding to the formula (Vbis) in which $1 \leq n \leq 4$, d=0 or 1, X=N-hydroxysuccinimide, A is an oxycarbonyl or acyl group, and particular the compounds in which p, m and v are comprised from 1 to 10 and preferably equal to 1 or 2, and preferably those in which A=Boc and Fmoc.

The isocyanates of formula (Vbis) can be used as precursors for the synthesis of compounds of formula (V) and can be obtained from compounds (XI).

The invention also comprises compounds of the formula (VII)

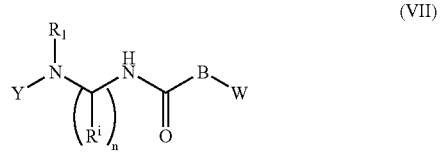

(VII)

in which
"n" is a whole number greater than or equal to 1, preferably 1 to 50, preferably 1 to 10,
"i" is a whole number varying from 2 to n+1,
the Y group can be or contain:
1/ a pseudopeptide (peptide containing one or several pseudopeptide linkages)

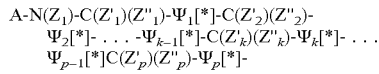

"p" is a whole number greater than or equal to 1, preferably 1 to 50, preferably 1 to 10,
"k" is a whole number varying from 1 to p,
or A is a group selected from:
hydrogen
oxycarbonyl (ROCO), preferably Boc (R=C(CH$_3$)$_3$), Fmoc (fluorenylmetoxycarbonyl), benzyloxycarbonyl (R=CH$_2$Ph), allyloxycarbonyl (R=—CH$_2$CH=CH$_2$),
acyl (RCO), preferably R=CH$_3$, CH$_2$CH$_3$, CH(CH$_3$)$_2$, C(CH$_3$)$_3$, phenyl, benzyl, allyl, aryl,
alkyl (R), preferably R=trityl, CH$_3$, CH$_2$CH$_3$, CH(CH$_3$)$_2$, C(CH$_3$)$_3$, benzyl, allyl,
phenyl, particularly aryl,
urea (RNHCO), preferably R=CH$_3$, CH$_2$CH$_3$, CH(CH$_3$)$_2$, C(CH$_3$)$_3$, phenyl, benzyl, allyl,
phthalimide (R$^1$=Ø)

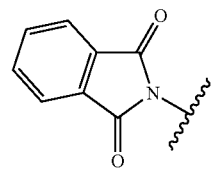

biotin
the group A can form with the nitrogen atom N with which it is contiguous an "NH$_2$$^+$" entity
$Z_k$, $Z'_k$ and $Z''_k$ can each represent independently:
hydrogen,
the protected or unprotected side chain of an amino acid selected from proteinogenic and non-proteinogenic amino acids,
a (C1–C20) alkyl group, unsubstituted or substituted by one or several of the following substituents:
1/ —COOR$_b$
2/ —CONHR$_b$
3/ —COOH
4/ —OH, OR$_b$
5/ —NHR$_b$
6/ —NH$_2$
7/ —NH(CO)R$_b$
8/ aryl whose cyclic structure contains 5 to 20 carbon atoms
9/ halogen
10/ carbonyl of 1 to 10 carbon atoms
11/ nitrile
12/ guanidine
an aryl group, whose cyclic structure contains 5 to 20 atoms
a halogen
—OR$_b$
—COOR$_b$
—CONHR$_b$
—CONH$_2$
—CH$_2$COOR$_b$
—CH$_2$CONHR$_b$
—CH$_2$CONH$_2$
R$_b$ representing an allyl, benzyl, t-butyl, fluorenylmethyl, alkyl having 1 to 20 carbon atoms group, or an aryl group whose cyclic structure contains 5 to 20 carbon atoms,
-Ψ$_k$[*]- are independently either CO—NH peptide linkages, or linkages of different chemical natures selected particularly from the following list:
Ψ$_k$[*]-=—CH(F$_k$)—; —CO—; —N(F$_k$)CO—; —CH(F$_k$)CO—; —CH(F$_k$)NHCO—; —N(F$_k$)—; —CON(F$_k$)—;

—CH$_2$CH$_2$; —CH(F$_k$)=CH(F$_k$')—; —CH$_2$NH—; —NHCO—; —NHCONH—; —N(F$_k$)CON(F$_k$')—; —COCH$_2$—; —CH(OH)CH$_2$—; —CH(OH)CH$_2$NH—; —CH$_2$O—; —CH$_2$—NHCONH—; CH(F$_k$)NHCON(F$_k$')—; —CH$_2$—CONH—; CH(F$_k$)CONH—; —CH(F$_k$)CH(F$_k$')CONH—

F$_k$ and F$_k$' representing, independently of each other, hydrogen, the protected or unprotected side chain of an amino acid selected from proteinagenic and non-proteinagenic amino acids, halogen, an alkyl group of 1 to 20 carbon atoms, or an aryl group whose cyclic structure contains 5 to 20 carbon atoms, 2/ an amino acid residue or an amino acid chain:

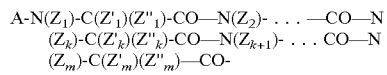

"m" is a whole number greater than or equal to 1, preferably 1 to 50, preferably 1 to 10,
"k" is a whole number varying from 1 to m,
A defined as above,
3/ a GP group which can be:
a protective group selected from:
oxycarbonyl (GP=ROCO), preferably Boc (R=C(CH$_3$)$_3$), Fmoc (fluorenylmethoxycarbonyl), benzyloxycarbonyl (R=CH$_2$Ph), allyloxycarbonyl (R=—CH$_2$CH=CH$_2$),
acyl (GP=RCO), preferably R=CH$_3$, CH$_2$CH$_3$, CH(CH$_3$)$_2$, C(CH3)3, phenyl, benzyl, allyl, aryl,
alkyl (R), preferably R=trityl, CH$_3$, CH$_2$CH$_3$, CH(CH$_3$)$_2$, C(CH$_3$)$_3$, benzyl, allyl,
phenyl, particularly aryl,
urea (RNHCO), preferably R=CH$_3$, CH$_2$CH$_3$, CH(CH$_3$)$_2$, C(CH$_3$)$_3$, phenyl, benzyl, allyl,
phthalimide (R$^1$=Ø)

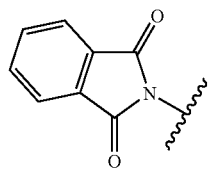

biotin
O$_2$ (corresponds to a nitro group as a masked amino form), R1=Ø
the GP group which can also be such that the "GP-N" entity forms an "NH$_2$$^+$" entity
the groups R$^1$, R$^i$ and R can each represent independently of each other:
hydrogen,
halogen,
the protected or unprotected side chain of an amino acid selected from natural and synthetic amino acids,
a (C1–C20) alkyl group, unsubstituted or substituted with one or several substituents from the following:
1/ —COOR$_a$
2/ —CONHR$_a$
3/ —COOH
4/ —OH
5/ —OR$_a$
6/ —NHR$_a$
7/ —NH$_2$
8/ —NH(CO)R$_a$
9/ aryl, whose cyclic structure contains 5 to 20 carbon atoms
10/ halogen
11/ carbonyl
12/ nitrile
13/ guanidine
14/ nitro
an aryl group, whose cyclic structure contains 5 to 20 carbon atoms
an OR$_a$ group
an NH$_2$ group
an OH group
—COOR$_a$
—CONHR$_a$
—CONH$_2$
—CH$_2$COOR$_a$
—CH$_2$CONHR
—CH$_2$CONH$_2$ R$_a$ representing an allyl, benzyl, t-butyl, fluorenylmethyl, alkyl having 1 to 20 carbon atoms group, or an aryl group whose cyclic structure contains 5 to 20 carbon atoms,
the B group can be either N—W' or O,
the W and W' groups can be or contain:
A/ hydrogen,
B/ a (C1–C20) alkyl group, unsubstituted or substituted with one or several of the following substituents:
1/ —COOR$_h$
2/ —CONHR$_h$
3/ —COOH
4/ —OH
5/ —OR$_h$
6/ —NHR
7/ —NH$_2$
8/ —NH(CO)R$_h$
9/ aryl, whose cyclic structure contains 5 to 20 carbon atoms
10/ halogen
11/ carbonyl of 1 to 10 carbon atoms
12/ nitrile
13/ guanidine R$_h$ representing an allyl, benzyl, t-butyl, fluorenylmethyl, alkyl having 1 to 20 carbon atoms group, or an aryl group whose cyclic structure contains 5 to 20 carbon atoms,
C/ an aryl group, whose cyclic structure contains 5 to 20 carbon atoms,
D/ a protected or unprotected side chain of amino acids selected from proteinagenic and non-proteinagenic acids and in the case of proline, W=W'=—CH$_2$—CH$_2$—CH$_2$—CH(COOR)—)
E/ a pseudopeptide (peptide containing one or several pseudopeptide linkages)

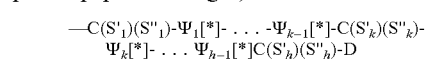

"h" is a whole number greater than or equal to 1 and preferably 1 to 50, preferably 1 to 10,
"k" is a whole number varying from 1 to h,
D can be:
hydrogen,
—COOH
—COOR$_c$
—CONH$_2$
—CH$_2$COOR$_c$
—NHCOR$_c$
—NH (R$_c$)
—CONR$_c$R$_d$
—N (R$_c$) CON (R$_d$)
—OH
—OR$_c$ —CN
—C(O)R$_c$ R$_c$ and R$_d$ representing an allyl, benzyl, t-butyl, fluorenylmethyl, alkyl having 1 to 20 carbon atoms group, or an aryl group whose cyclic structure contains 5 to 20 carbon atoms, S$_k$, S'$_k$, and S"$_k$ can each represent independently of each other:
hydrogen,
the protected or unprotected side chain of an amino acid selected from proteinogenic and non-proteinogenic amino acids,
a (C1–C20) alkyl group, unsubstituted or substituted with one or several of the following substituents:
1/ —COOR$_e$
2/ —CONHR$_e$
3/ —COOH
4/ —OH
5/ —NHR$_e$
6/ —NH$_2$
7/ —NH(CO)R$_e$
8/ aryl whose cyclic structure contains 5 to 20 carbon atoms
9/ halogen
10/ carbonyl
11/ nitrile
12/ guanidine
an aryl group, whose cyclic structure contains 5 to 20 carbon atoms
an OR$_e$ group
an NH$_2$ group
an OH group
a halogen R$_e$ representing an allyl, benzyl, t-butyl, fluorenylmethyl, alkyl having 1 to 20 carbon atoms group, or an aryl group whose cyclic structure contains 5 to 20 carbon atoms, -Ψ$_k$[*]- are independently either CO—NH peptide linkages or linkages of different chemical nature selected particularly from the following list:

Ψ$_k$[*]-=—CH(F$_k$)—; —CO—; —N(F$_k$)CO—; —CH(F$_k$)CO—; —CH(F$_k$)NHCO—; —N(F$_k$)—; —CON(F$_k$)—; —CH$_2$CH$_2$; —CH(F$_k$)=CH(F$_k$')—; —CH$_2$NH—; —NHCO—; —NHCONH—; —N(F$_k$)CON(F$_k$')—; —COCH$_2$—; —CH(OH)CH$_2$—; —CH(OH)CH$_2$NH—; —CH$_2$O—; —CH$_2$—NHCONH—; CH(F$_k$)NHCON(F$_k$')—; —CH$_2$—CONH—; CH(F$_k$)CONH—; —CH(F$_k$)CH(F$_k$')CONH—

F$_k$ and F$_k$' representing, independently of each other, hydrogen, the protected or unprotected side chain of an amino acid selected from proteinogenic and non-proteinogenic amino acids, a halogen, an alkyl group of 1 to 20 carbon atoms, or an aryl group whose cyclic structure contains 5 to 20 carbon atoms, F/ an amino acid residue or a chain of amino acid residues:

—C(S'$_1$)(S"$_1$)-CO—N(S$_2$)- . . . -CO—N(S$_k$)-C(S'$_k$)(S"$_k$)-CO—N(S$_{k+1}$)- . . . CO—N(S$_v$)-C(S'$_v$)(S"$_v$)-D

"v" is a whole number greater than or equal to 1, preferably 1 to 50, preferably 1 to 10 and preferably v>3 and v>5, "k" is a whole number varying from 1 to v, D, S$_k$, S'$_k$ and S"$_k$ are defined independently of each other as above, the compounds of formula (VII) moreover have the following property:
if one or several asymmetric carbons are present in the formula (VII), then their configuration can be independently of each other either D (dextro) or L (levo), the groups R$^1$ and R$^i$ can also be defined on the basis of intramolecular cyclizations which are the following:
1/ cyclization between R$^i$ and R$^{i+kc}$ (where kc is a positive whole number, preferably comprised from 1 to 3)
2/ cyclization between R$^1$ and R$^i$ wherein preferably i=2, 3 or 4,

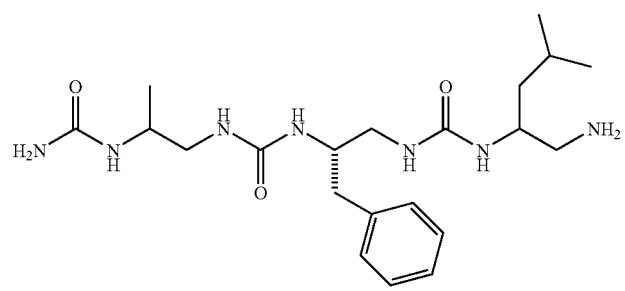

a

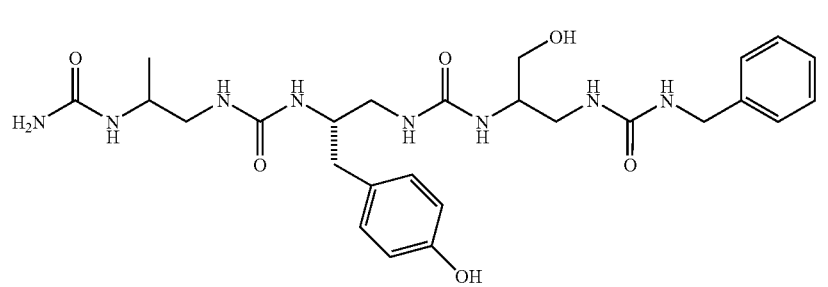

b

-continued
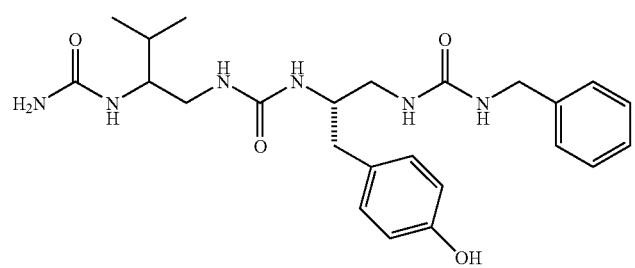
c
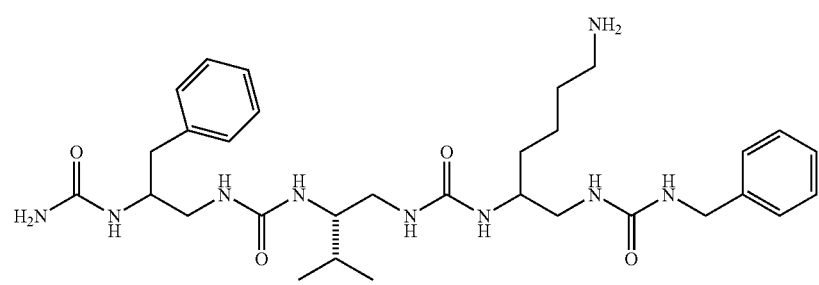
d
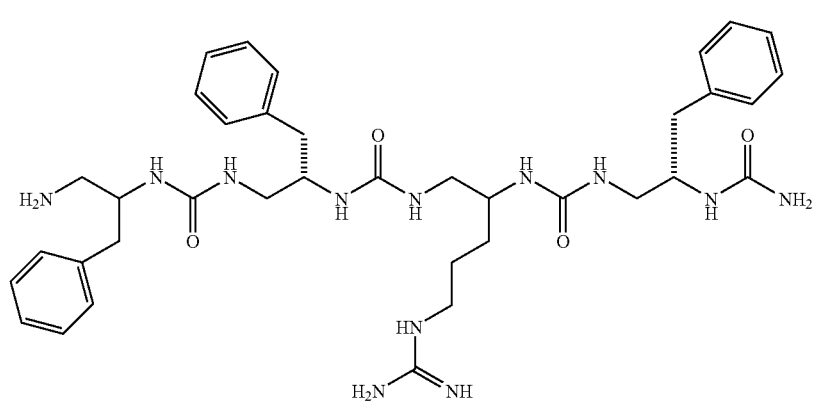
e
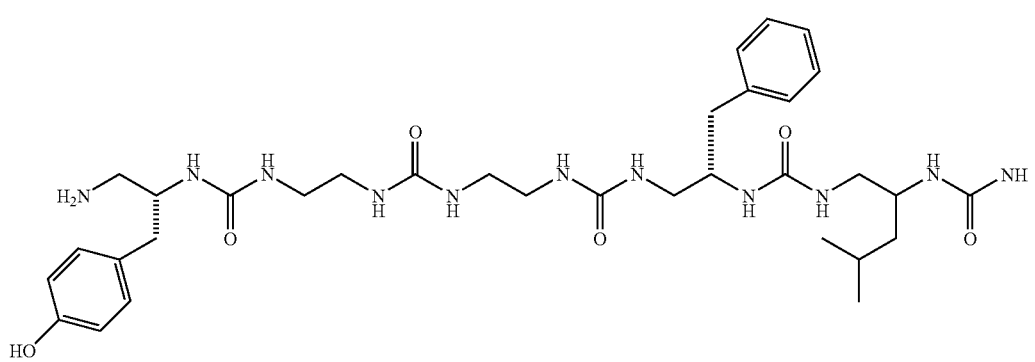
f
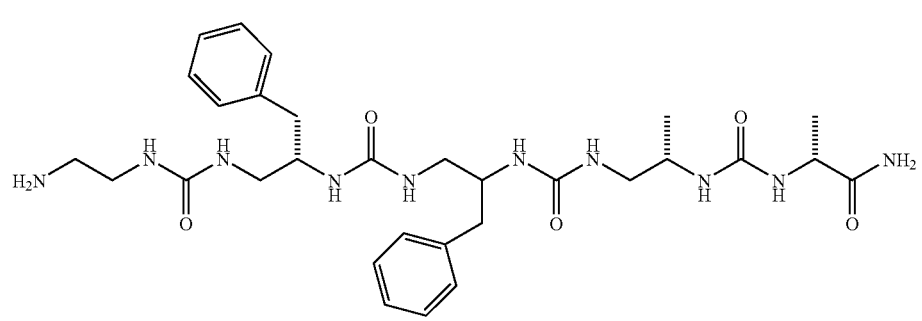
g provided that the compound of formula (VII) is different from the analogs of the peptide Tyr-Gly-Gly-Phe-Leu-OH, containing one or several derivatives as defined below mimicking the side chain of the amino acids present in the peptide and permitting the introduction of one or several urea linkages, which is to say the compound of formula (VII) is different from the following compounds:

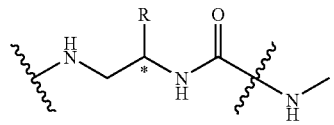

in which R represents hydroxybenzyl, a hydrogen atom, a benzyl group, or an isobutyl group, provided that the compound of formula (VII) is different from:

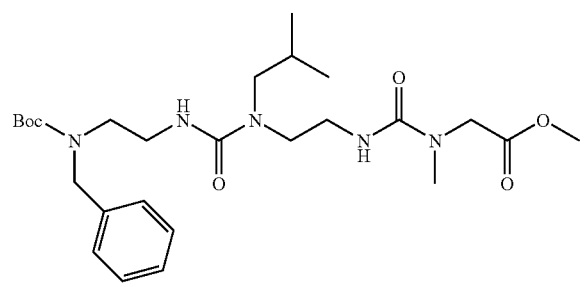

In formula (VII), when B represents N—W', N corresponds to the nitrogen atom, and when B represents O, O corresponds to the oxygen atom.

The compounds of type (VII) are reaction products of compounds of type (III) and (III bis) or possibly (IV) with derivatives containing a primary or secondary amine or an alcohol.

The invention also relates to compounds of formula (VI)

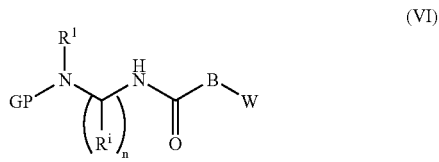

(VI)

in which n, i, GP, $R^1$, $R^i$, B and W have the meanings mentioned above with respect to formula (VII).

Compounds of type (VI) are reaction products of the compounds of type (I) and (I bis) or possibly (II) with derivatives containing a primary or secondary amine or an alcohol.

A preferred group of compounds of formula (VII) is constituted by those in which $1 \leq n \leq 4$, and particularly the following compounds in which v, h, m and p are comprised from 1 to 10 and preferably 1 to 5 and more particularly the following compounds:

n = 1
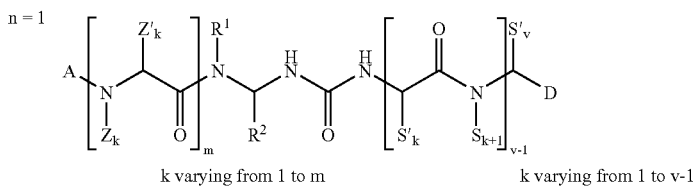
k varying from 1 to m    k varying from 1 to v-1 n = 2
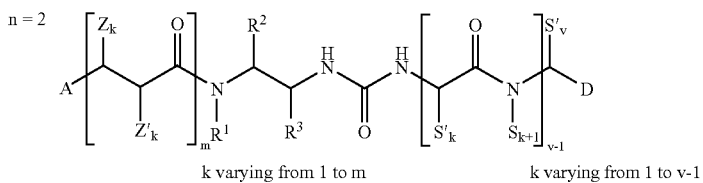
k varying from 1 to m    k varying from 1 to v-1

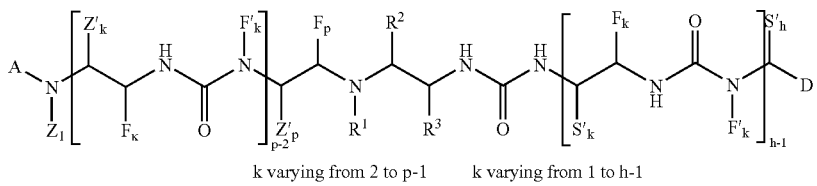
k varying from 2 to p-1    k varying from 1 to h-1 n = 3
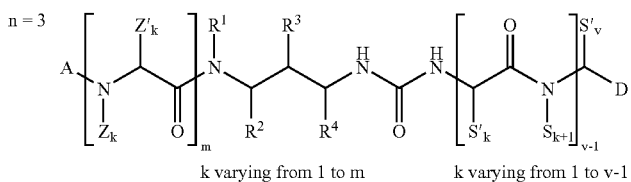
k varying from 1 to m    k varying from 1 to v-1

-continued n = 4
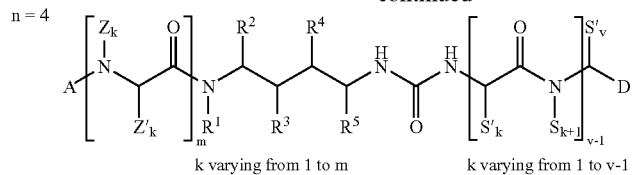
k varying from 1 to m     k varying from 1 to v-1

A preferred group of compounds is constituted by those of formula (VI) in which $1 \leq n \leq 4$, GP is an oxycarbonyl or acyl group as defined above with respect to the compounds of formula (VI), and more particularly the following compounds in which v and h are comprised between 1 and 10, and preferably equal to 1 or 2, and particularly those in which GP=Boc and Fmoc:

n = 1
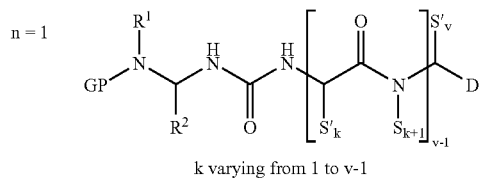
k varying from 1 to v-1 n = 2
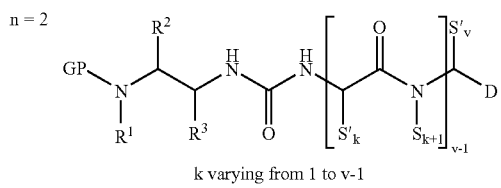
k varying from 1 to v-1

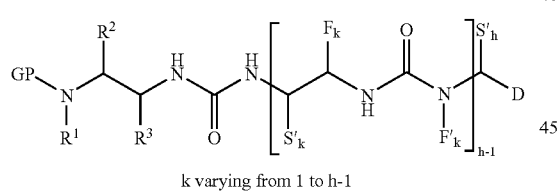
k varying from 1 to h-1 n = 3
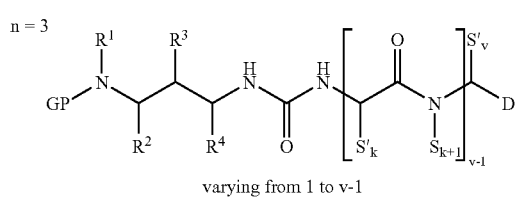
varying from 1 to v-1 n = 4
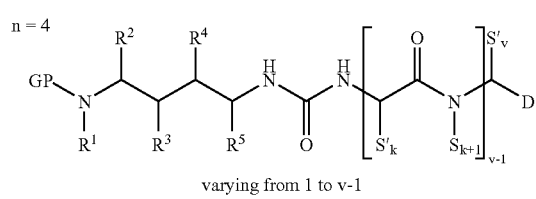
varying from 1 to v-1

The invention also relates to compounds of the formula (VIII)

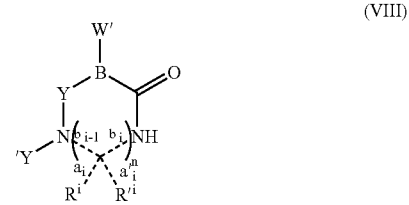
(VIII)

in which:

the total number of atoms forming the cycle is greater than seven, the groups $R^i$, $R^{'i}$, Y', W', B have the meanings already indicated above, the group Y in this new case can be or contain:

I/ a (C1–C20) alkyl group, unsubstituted or substituted with one or more substituents from the following:
1/ —COOR$_e$
2/ —CONHR$_e$
3/ —COOH
4/ —OH
5/ —OR
6/ —NHR$_e$
7/ —NH$_2$
8/ —NH(CO)R$_e$
9/ aryl, whose cyclic structure contains 5 to 20 carbon atoms,
10/ halogen
11/ carbonyl of 1 to 10 carbon atoms
12/ nitrile
13/ guanidine R$_e$ representing an alkyl group of 1 to 20 carbon atoms, or an aryl group whose cyclic structure contains 5 to 20 carbon atoms, II/ an aryl group III/ a pseudopeptide (peptide containing one or several pseudopeptidic linkages)

(on B←)-C(Z'$_1$)(Z''$_1$)-Ψ$_1$[*]- . . . -Ψ$_{k-1}$[*](Z$_k$)-C(Z'$_k$)(Z''$_k$)-Ψ$_k$[*]- . . . Ψ$_{p-1}$[*]C(Z'$_p$)(Z''$_p$)-CO-(→on NY')

"p" is a whole number greater than or equal to 1, preferably 1 to 50, preferably 1 to 10, Z$_k$, Z'$_k$ and Z''$_k$ can each represent independently of each other:

hydrogen, the side chain of an amino acid selected from proteinogenic or non-proteinogenic amino acids a (C1–C20) alkyl group, unsubstituted or substituted with one or several substituents from the following:

1/ —COOR$_b$
2/ —CONHR$_b$
3/ —COOH
4/ —OH, OR$_b$
5/ —NHR$_b$
6/ —NH$_2$
7/ —NH(CO)R$_b$
8/ aryl whose cyclic structure contains 5 to 20 carbon atoms
9/ halogen
10/ carbonyl of 1 to 10 carbon atoms
11/ nitrile
12/ guanidine an aryl group, whose cyclic structure contains 5 to 20 carbon atoms a halogen
—COOR$_b$
—CONHR$_b$
—CONH$_2$
—CH$_2$COOR$_b$
—CH$_2$CONHR$_b$
—CH$_2$CONH$_2$ R$_b$ representing an alkyl group of 1 to 20 carbon atoms, or an aryl group whose cyclic structure contains 5 to 20 carbon atoms, -Ψ$_k$[*]- are independently either CO—NH peptidic linkages or linkages of different chemical natures selected particularly from the following list:

-Ψ$_k$[*]-=—CH$_2$CH$_2$; —CH(F$_k$)=CH(F$_k$')—; —CH$_2$NH—; —NHCO—; —NHCONH—; —COCH$_2$—; —CH(OH)CH$_2$—; —CH(OH)CH$_2$NH—; —CH$_2$—; —CH (F$_k$)—; —CH$_2$O—; —CH$_2$—NHCONH—; CH(F$_k$)NH-CONF$_k$'—; CH$_2$—CONH—; CH(F$_k$)CONH—; —CH(F$_k$)CH(F'$_k$)CONH—

F$_k$ and F$_k$' representing, independently of each other, hydrogen, halogen, an alkyl group of 1 to 20 carbon atoms, or an aryl group whose cyclic structure contains 5 to 20 carbon atoms, IV/ an amino acid residue or a chain of amino acid residues:

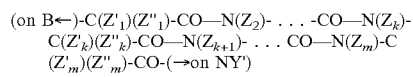

"m" is a whole number greater than or equal to 1, preferably 1 to 50, preferably 1 to 10, Z$_k$, Z'$_k$, and Z"$_k$ are defined as before.

V/ an oligomer of urea defined as follows:

"u" is a whole number greater than or equal to 1, preferably 1 to 50, and preferably 1 to 10, "q" is a whole number greater than or equal to 1, preferably 1 to 50, and preferably 1 to 10, "j" is a whole parameter comprised between 2 and u+1, "r" is a whole parameter greater than or equal to 1 taking all the values comprised from 1 to q–1.

"a$_r^j$ and a'$_r^j$", represented by a broken line, are covalent bonds which can be single (s), or double (d), "b$_r^j$ and b$_r^{j-1}$", shown by broken line, are covalent bonds which can be simple (s), double (d) or triple (t) provided that:

b$_q^1$ and b$_q^{u+1}$ are always single bonds (s), if b$_r^j$=d, then a$_r^j$ and a$_r^{j+1}$=s; a'$_r^j$ and a'$_r^{j+1}$=Ø; b$_r^{j-1}$ and b$_r^{j+1}$=s if b$_r^j$=t, then a$_r^j$ and a$_r^{j+1}$=Ø; a'$_r^j$ and a'$_r^{j+1}$=Ø; b$_r^{j-1}$ and b^{j+1} =s if a$_r^j$=d, then b$_r^{j-1}$ and b$_r^j$=s, certain of these bonds can also form a part of aromatic rings, Z$_r$, Z$_r^j$, Z'$_r^j$ have meanings indicated with respect to R$^1$, R$^i$, R$^{i'}$ as defined above.

A preferred group of compounds of formula (VIII) is constituted by those in which 1≦n≦4, and particularly the following compounds in which h, v, t, p, m, and q are comprised from 1 to 10 and preferably 1 to 5, and more particularly the following compounds:

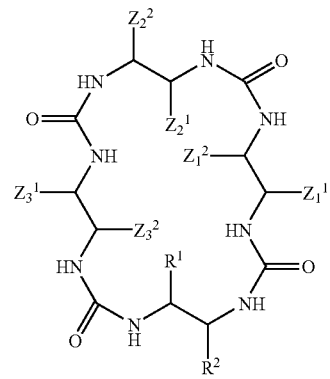

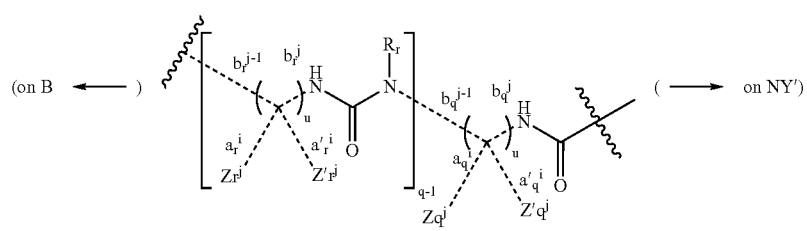

-continued

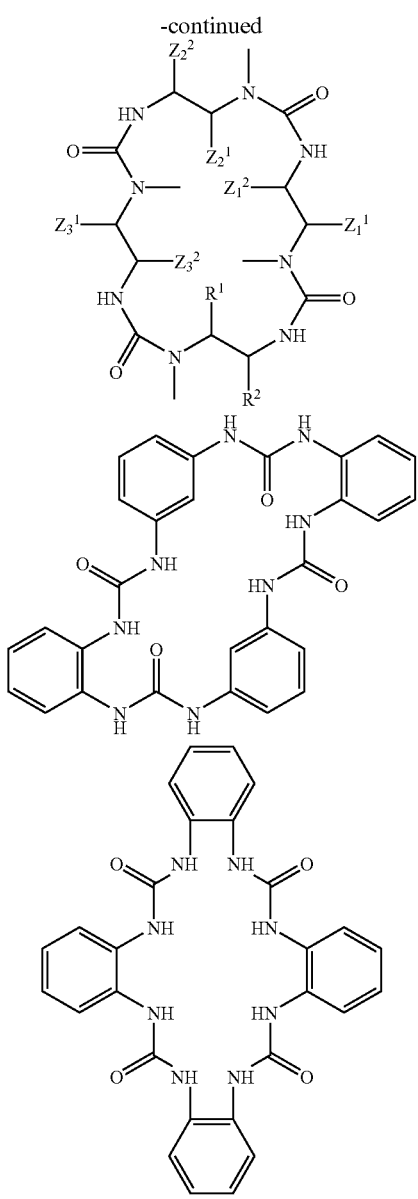

in which $R^1$ and $R^2$ have the meanings indicated above and in which $Z_1^1$, $Z_1^2$, $Z_2^1$, $Z_2^2$, $Z_3^1$ and $Z_3^2$ have the meanings indicated with respect to $Z_r^j$.

The invention also has for its object cyclic compounds of formula (VIII bis)

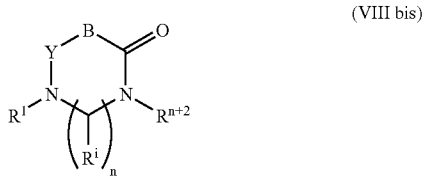

(VIII bis)

in which:

the total number of atoms forming the cycle is greater than six, preferably greater than or equal to 7, "n" is a whole number greater than or equal to 1, preferably from 1 to 10, preferably from 1 to 4, "i" is a whole number varying from 2 to n+1, the groups $R^1$, $R^i$ and $R^{n+2}$ each can represent independently of each other:

hydrogen halogen the protected or unprotected side chain of an amino acid selected from natural or synthetic amino acids a (C1–C2) alkyl group unsubstituted or substituted with one or several substituents of the following:
1/ —$COOR_a$
2/ —$CONHR_a$
3/ —COOH
4/ —OH
5/ —$OR_a$
6/ —$NHR_a$
7/ —$NH_2$
8/ —$NH(CO)R_a$
9/ aryl, whose cyclic structure contains 5 to 20 carbon atoms
10/ halogen
11/ carbonyl of 1 to 10 carbon atoms
12/ nitrile
13/ guanidine
14/ nitro an aryl group, whose cyclic structure contains 5 to 20 carbon atoms an $OR_a$ group
an $NH_2$ group
an OH group
—$COOR_a$
—$CONHR_a$
—$CONH_2$
—$CH_2COOR_a$
—$CH_2CONHR_a$
—$CH_2CONH_2$ $R_a$ representing an allyl, benzyl, t-butyl, fluorenylmethyl, alkyl having 1 to 20 carbon atoms group, or an aryl group whose cyclic structure contains 5 to 20 carbon atoms, the groups $R^1$ and $R^i$ can also be defined on the basis of intramolecular cyclizations which are the following:

1/ cyclization between $R^i$ and $R^{i+kc}$ (where kc is a positive integer, preferably between 1 and 3)

2/ cyclization between $R^1$ and $R^i$ wherein preferably i=2, 3 or 4, the Y group can be or contain:

I/ a (C1–C20) alkyl group, unsubstituted or substituted with one or several substituents from the following:
1/ —$COOR_e$
2/ —$CONHR_e$
3/ —COOH
4/ —OH
5/ —OR
6/ —$NHR_e$
7/ —$NH_2$
8/ —$NH(CO)R_e$
9/ aryl, whose cyclic structure contains 5 to 20 carbon atoms,
10/ halogen
11/ carbonyl of 1 to 10 carbon atoms
12/ nitrile
13/ guanidine $R_e$ representing an allyl, benzyl, t-butyl, fluorenylmethyl, alkyl having 1 to 20 carbon atoms group, or an aryl group whose cyclic structure contains 5 to 20 carbon atoms, II/ an aryl group III/ a pseudopeptide (peptide containing one or several pseudopeptidic bonds)

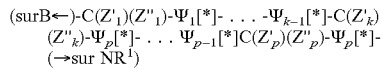

"p" is a whole number greater than or equal to 1, preferably 1 to 50, preferably 1 to 10, $Z_k$, $Z'_k$ and $Z''_k$ can each represent independently of each other:

hydrogen, the protected or unprotected side chain of an amino acid selected from proteinogenic or non-proteinogenic amino acids, a (C1–C20) alkyl group, unsubstituted or substituted with one or several of the following substituents:

1/ —$COOR_b$
2/ —$CONHR_b$
3/ —COOH
4/ —OH, $OR_b$
5/ —$NHR_b$
6/ —$NH_2$
7/ —$NH(CO)R_b$
8/ aryl whose cyclic structure contains 5 to 20 carbon atoms
9/ halogen
10/ carbonyl of 1 to 10 carbon atoms
11/ nitrile
12/ guanidine an aryl group, whose cyclic structure contains 5 to 20 carbon atoms a halogen
—$COOR_b$
—$CONHR_b$
—$CONH_2$
—$CH_2COOR_b$
—$CH_2CONHR_b$
—$CH_2CONH_2$ Rb representing an allyl, benzyl, t-butyl, fluorenylmethyl, alkyl having 1 to 20 carbon atoms group, or an aryl group whose cyclic structure contains 5 to 20 carbon atoms, -$\Psi_k[*]$- are independently either CO—NH peptidic linkages or linkages of different chemical natures selected particularly from the following list:

$\Psi_k[*]$-=—CH($F_k$)—; —CO—; —N($F_k$)CO—; —CH($F_k$)CO—; —CH($F_k$)NHCO—; —N($F_k$)—; —CON($F_k$)—; —$CH_2CH_2$; —CH($F_k$)=CH($F_{k'}$)—; —$CH_2$NH—; —NHCO—; —NHCONH—; —N($F_k$)CON($F_k'$)—; —$COCH_2$—; —CH(OH)$CH_2$—; —CH(OH)$CH_2$NH—; —$CH_2$O—; —$CH_2$—NHCONH—; CH($F_k$)NHCON($F_k'$)—; —$CH_2$—CONH—; CH($F_k$)CONH—; —CH($F_k$)CH($F_k'$)CONH—

$F_k$ and $F_k'$ representing, independently of each other, hydrogen, a protected or unprotected side chain of an amino acid selected from proteinogenic and proteinogenic amino acids, halogen, an alkyl group of 1 to 20 carbon atoms, or an aryl group whose cyclic structure contains 5 to 20 carbon atoms, IV/ an amino acid residue or a chain of amino acid residues:

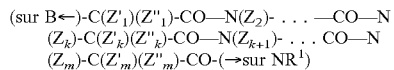

"m" is a whole number greater than or equal to 1, preferably 1 to 50, preferably 1 to 10, $Z_k$, $Z'_k$, and $Z''_k$ are defined as above, the B group can be either N—W' or O, the W' group can be or contain:

A/ hydrogen,

B/ a (C1–C20) alkyl group, unsubstituted or substituted with one or several substituents from the following:

1/ —$COOR_h$
2/ —$CONHR_h$
3/ —COOH
4/ —OH
5/ —$OR_h$
6/ —NHR
7/ —$NH_2$
8/ —$NH(CO)R_h$
9/ aryl, whose cyclic structure contains 5 to 20 carbon atoms,
10/ halogen
11/ carbonyl of 1 to 10 carbon atoms
12/ nitrile
13/ guanidine $R_h$ representing an allyl, benzyl, t-butyl, fluorenylmethyl, alkyl having 1 to 20 carbon atoms group, or an aryl group whose cyclic structure contains 5 to 20 carbon atoms, C/ an aryl group, whose cyclic structure contains 5 to 20 carbon atoms, D/ a protected or unprotected amino acid side chain selected from proteinogenic and non proteinogenic amino acids and in the case of prolin, W=W'=—$CH_2$—$CH_2$—$CH_2$—CH (COOR)—)

E/ a pseudopeptide (peptide containing one or several pseudopeptidic linkages)

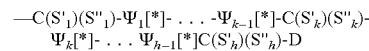

"h" is a whole number greater than or equal to 1, preferably 1 to 50, preferably 1 to 10, "k" is a whole number varying from 1 to h, D can be:

hydrogen,
—COOH
—$COOR_c$
—$CONH_2$
—$CH_2COOR_c$
—$NHCOR_c$
—$CONR_cR_d$
—N ($R_c$) CON ($R_d$)
—OH
—$OR_c$
—CN
—C(O) $R_c$ $R_c$ and $R_d$ representing an allyl, benzyl, t-butyl, fluorenylmethyl, alkyl having 1 to 20 carbon atoms group, or an aryl group whose cyclic structure contains 5 to 20 carbon atoms, $S_k$, $S'_k$ and $S''_k$ can each represent independently of each other:

hydrogen, the protected or unprotected side chain of an amino acid selected from proteinogenic and non-proteinogenic amino acids, a (C1–C20) alkyl group, unsubstituted or substituted with one or several substituents from the following:

1/ —$COOR_e$
2/ —$CONHR_e$
3/ —COOH

4/ —OH
5/ —NHR$_e$
6/ —NH$_2$
7/ —NH(CO)R$_e$
8/ aryl, whose cyclic structure contains 5 to 20 carbon atoms
9/ halogen
10/ carbonyl
11/ nitrile
12/ guanidine
an aryl group, whose cyclic structure contains 5 to 20 carbon atoms
an OR$_e$ group
an NH$_2$ group
an OH group
halogen
R$_e$ representing an allyl, benzyl, t-butyl, fluorenylmethyl, alkyl having 1 to 20 carbon atoms group, or an aryl group whose cyclic structure contains 5 to 20 carbon atoms, -Ψ$_k$[*]- are independently either CO—NH peptidic linkages or linkages of different chemical nature selected particularly from the following list:

Ψ$_k$[*]-=—CH(F$_k$)—; —CO—; —N(F$_k$)CO—; —CH(F$_k$)CO—; —CH(F$_k$)NHCO—; —N(F$_k$)—; —CON(F$_k$)—; —CH$_2$CH$_2$—; —CH(F$_k$)=CH(F$_k$′)—; —CH$_2$NH—; —NHCO—; —NHCONH—; —N(F$_k$)CON(F$_k$′)—; —COCH$_2$—; —CH(OH)CH$_2$—; —CH(OH)CH$_2$NH—; —CH$_2$O—; —CH$_2$—NHCONH—; CH(F$_k$)NHCON(F$_k$′)—; —CH$_2$—CONH—; CH(F$_k$)CONH—; —CH(F$_k$)CH(F$_k$′)CONH—

F$_k$ and F$_k$′ representing, independently of each other, hydrogen, a protected or unprotected side chain of an amino acid selected from proteinogenic and non-proteinogenic amino acids, halogen, an alkyl group of 1 to 20 carbon atoms, or an aryl group whose cyclic structure contains 5 to 20 carbon atoms, F/ an amino acid residue or chain of amino acid residues:

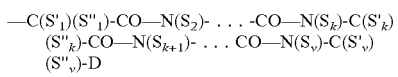

"v" is a whole number greater than or equal to 1, preferably 1 to 50, preferably 1 to 10 with preferably v>3 and v>5,
"k" is a whole number varying from 1 to v,
D, S$_k$, S′$_k$ and S″$_k$ are defined independently as above,
and more particularly the compounds responding to the formula (VIII bis) in which 1≦n≦4, h, v, p and m are comprised from 1 to 10 and preferably 1 to 5.

The compounds of the (VIII) and (VIII bis) type are cyclic compounds obtained from compounds of the (III) and (III bis) or (IV) type and by intramolecular reaction with an amine liberated after elimination of temporary protection.

The compounds of type (VIII) and (VIII bis) are cyclic compounds obtained from compounds of type (III) and (III bis) or (IV) and by intramolecular reaction with an amine freed after elimination of temporary protection.

In the compounds of formula (I), (I bis), (III), (IIIbis), (IV), (V), (Vbis), (VI) and (VII), the aryl group is preferably selected from:
1/ phenyl
2/ naphthyl
3/ indenyl
4/ thiophenyl
5/ benzothiophenyl
6/ furanyl
7/ benzofuranyl
8/ pyridyl
9/ indolyl
10/ pyrollyl
or the aryl group can be substituted with 1 to 6 substituents selected particularly from:
1/ alkyl of 1 to 10 carbon atoms
2/ halogen
3/ alkoxy of 1 to 10 carbon atoms
4/ hydroxyl
5/ amine of 1 to 10 carbon atoms
6/ ester of 1 to 10 carbon atoms
7/ nitrile
8/ aryl, whose cycle structure contains 5 to 20 carbon atoms
9/ nitro
10/ urea of 1 to 10 carbon atoms
11/ amide of 1 to 10 carbon atoms
12/ guanidine
13/ carboxylic acid of 1 to 10 carbon atoms.

According to a preferred embodiment of the process of the invention, the preparation of the compounds of formula (I bis), (II), (III bis), (IV), (V) or (Vbis) can be carried out from respectively:

compounds of formula (IX) (for compounds of formula (I bis) and (II))

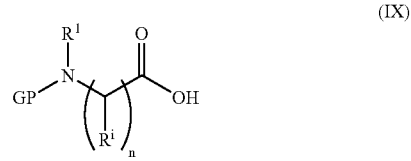

compounds of formula (X) (for compounds of formula (III bis) and (IV))

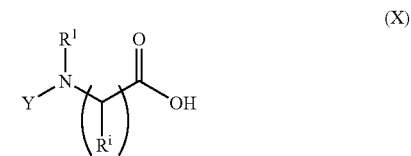

compounds of formula (XI) (for compounds of formula (V) and (Vbis))

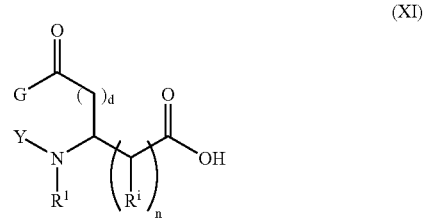

and comprises
(a) a step of transformation of the acid (IX) or (X) or (XI) into a corresponding acyl azide (XII) or (XIII) or (XIV) respectively,

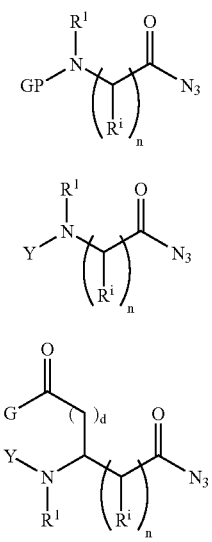

by a suitable treatment, (b) a step of transformation of the acyl azide (XII) or (XIII) or (XIV) by Curtius rearrangement into the corresponding isocyanate (II) or (IV) or (Vbis), respectively, (c) a step of treatment of the isocyanate (II), (IV) or (V bis), preferably not isolated, under conditions permitting obtaining a derivative of the carbamic acid of formula (I bis), (III bis) or (V).

According to a preferred embodiment of the process of preparation of the invention:

step a) of transformation of the acid (IX) or (X) or (XI) into the corresponding acyl azide (XII) or (XIII) or (XIV) respectively, is carried out for example by treatment of the mixed anhydride (formed by reaction of acid (IX), (X) or (XI) with ethyl or isobutyl chloroformate in the presence of a tertiary amine such as NMM (N-methylmorpholine), DIEA (di-isopropylethylamine) or Et$_3$N in THF (tetrahydrofurane)) with a sodium azide solution, step b) of transformation of the acyl azide (XII) or (XIII) or (XIV) into the corresponding isocyanate (II) or (IV) or (Vbis), respectively, is carried out for example by heating a solution of the acyl azide in a suitable solvent, particularly toluene or xylene, the formation of the isocyanate being followed by observation of the release of gas into the balloon, the end of the gaseous emission signifying completion of the Curtius rearrangement, step c) of treatment of the corresponding isocyanate (II) or (IV) or (Vbis) is carried out, when the isocyanate is in solution, for example in hot toluene, with one of the derivatives from the following list:

N-hydroxysuccinimide
phenol
pentafluorophenol
pentachlorophenol
p-nitrophenol
2,4-dinitrophenol
2,4,5-trichlorophenol
2,4-dichloro-6-nitrophenol
hydroxy-1,2,3-benzotriazole
1-oxo-2-hydroxydihydrobenzotriazine (HODhbt)
7-aza-1-hydroxybenzotriazole (HOAt)
4-aza-1-hydroxybenzotriazole (4-HOAt)
imidazole
tetrazole (permitting obtaining a pre-activated synthon) and if desired a base such as pyridine, to obtain a carbamic acid derivative of formula (I bis), (III bis) or (V), which is then preferably isolated, preferably by crystallization or by purification, particularly on a silica column, or by HPLC or by aqueous, acid or basic washing after dissolution in an organic solvent.

By way of example, in step a) described above, the mixed anhydride is formed by reaction of the acid (IX), (X) or (XI) with ethyl or isobutyl chloroformate in the presence of a tertiary amine such as NMM (N-methylmorpholine), DIEA (di-isopropylethylamine) or Et$_3$N in THF (tetrahydrofurane) at a temperature of −15° C.

By way of example, in step b) described above, the solution of acyl azide is heated in a suitable solvent (particularly toluene or xylene), to a temperature of 65° C.

By way of example, in step c) described above, the treatment of the isocyanate is carried out, when it is in solution, for example in hot toluene, at a temperature of 65° C.

According to another embodiment of the invention, the process of preparation of the compounds of formula (VI) or (VII) comprises the reaction of compounds containing primary or secondary amines or alcohols, with one of the products of formula (I bis), (II), (III bis), (IV), (V) or (Vbis) defined above, for example in a solvent such as DMF, H$_2$O/acetone, THF, dichloromethane or acetonitrile with or without the addition of a base such as a tertiary amine (for example Et$_3$N, DIEA, NMM, collidine, lutidine) or such as sodium carbonate (Na$_2$CO$_3$) or sodium bicarbonate (NaHCO$_3$).

According to another preferred embodiment of the invention, the process of preparation of the compounds of formula (VIII bis) comprises the intramolecular cyclization of products of formula (III bis) or compounds of formula (VII), for example in a solvent such as DMF, H$_2$O/acetone, THF, dichloromethane or acetonitrile with or without the addition of a base such as a tertiary amine (for example Et$_3$N, DIEA, NMM, collidine, lutidine) or such as sodium carbonate (Na$_2$CO$_3$).

FIG. 1: FIG. 1 corresponds to the X-ray structure of the carbamate (Ig) corresponding to the following formula:

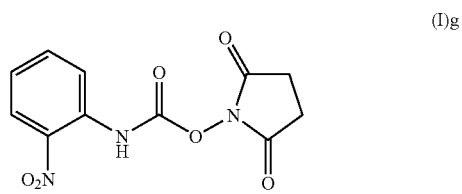

The invention is illustrated hereafter by examples I to III, which have no limiting value.

In example I, the reaction of the O-succinimidyl-2-(tert-butoxycarbonylamino)-ethylcarbamate derivatives with aliphatic or aromatic primary amines, secondary amines, or α- or β-amino acid derivatives, rapidly gives urea derivatives or urea oligomers with a high yield.

In example II, the O-succinimidyl-2-[(9H-fluoren-9-yl-methoxy)carbonylamino]-ethylcarbamate derivatives used in a repetitive manner in solid phase permit obtaining the desired urea pseudopeptides and urea oligomers, with a high yield.

EXAMPLE I

An efficacious synthesis of O-succinimidyl-2-(tert-Butoxycarbonylamino)-ethylcarbamate derivatives (I) and (Ibis) is described as well as their utilization as monomers active in the synthesis of di- and tri-substituted ureas and urea oligomers. The β-amino N-Boc-protected acids (IX) are first transformed into the corresponding acyl azide derivatives (XII). The isocyanate formed by Curtius rearrangement of compounds (XII) is immediately treated with N-hydroxysuccinimide in the presence of pyridin to give the corresponding carbamates (I) and (Ibis) (see the formula of reaction 1) (50–64%). These carbamates are stable and crystalline compounds which react spontaneously with primary and secondary amines at ambient temperature to give (VIe) ureas (79–87%). By way of example, the synthesis of the N-boc-protected tri-urea derivative (VIg) has also been carried out by step-by-step addition using carbamate (Ib).

The N-Boc-protected β-amino acids (IX) are first transformed into the corresponding acyl azides (XII) by reaction of their mixed anhydride (prepared with EtOCOCl/N-methylmorpholine) with NaN$_3$. The isocyanates (II), generated in situ by heating the acyl azide (XII) in toluene at 65° are immediately treated with N-hydroxysuccinimide (1 equivalent) in the presence of pyridine (1 equivalent) to give the carbamate (I) and (I bis). This sequence of reaction from (IX) is generally complete in less than one hour (reaction 1).

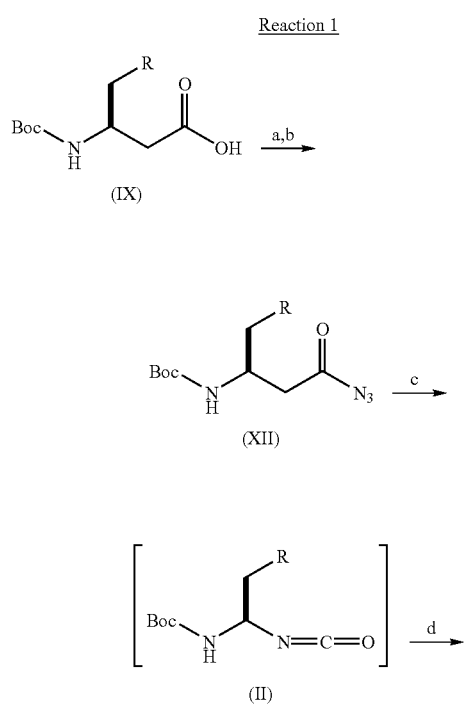

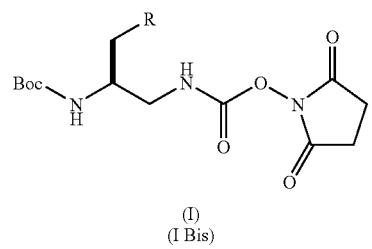

Reagents: (a) i-BuOCOCl, NMM, −20° C.; (b) NaN$_3$, H$_2$O; (c) Toluene, 65° C.; (d) N-hydroxysuccinimide, pyridine.

The O-succinimidyl carbamates (I) and (Ibis) crystallize for the most part directly from the solution of toluene at ambient temperature and are obtained simply by filtration with suitable yield. Recrystallization in toluene or another suitable solvent permits obtaining pure specimens for analysis. It is interesting to note that the mild conditions employed are compatible with the use of functionalized side chains (Table 1).

TABLE 1

Conversion of β-amino acids (IX) into O-succinimidyl carbamates (I) and (Ibis).

| R = | Products (I) and (I bis) | Yield (%)[a] | m.p. (° C.) | HPLC $t_R$(min)[b] |
|---|---|---|---|---|
| H | Ia | 55 | 132–134 | 6.95 |
| Me | Ib | 60 | 153–155 | 8.00 |
| i-Pr | Ic | 51 | 125–127 | 10.80 |
| Bn | Id | 55 | 163–164 | 12.79 |
| CH$_2$CO$_2$(Bzl) | Ie | 58 | 115–117 | 13.47 |
| CH(Me)OBzl | If | 64 | 109–110 | 14.59 |

[a]Yield of (I) and (I bis) after recrystallization.

[b]linear gradient of A (0.1% CF$_3$COOH in H$_2$O) and B (MeCN containing 0.08% CF$_3$COOH), 20–80% B, 20 min. The Compound of formula (I) and (I bis) is that indicated in reaction 1 above.

Starting with 2-nitrobenzoic acid[8], the corresponding O-succinimidyl carbamate (Ig) has been isolated with 71% yield after recrystallization in ethyl acetate. The X-ray structure of the carbamate (Ig) (FIG. 1) shows that the molecule has an extended configuration with an intra-molecular hydrogen bond between the adjacent nitro and carbamate groups (N$_2$.O$_2$, 2.62 Å). The succinimidyl cycle is turned about 77° relative to the plane of the phenyl cycle.

Carbamates (I), (I bis) and (Ig) are stable crystalline solids which can be stored for months at 4° C. without degradation. So as to study the possibilities and limits of the activated monomers of the invention for the preparation of substituted symmetric ureas, different amines and amino acids have been treated with the carbamates (I) and (I bis). The results are shown in Table 2.

TABLE 2

Formation of substituted ureas (VI) with carbamates (I) and (I bis)

| Entry | Carbamate | Amine | Time (min)[a] | Urea VI | Yield (%)[b] |
|---|---|---|---|---|---|
| 1 | Ia | H₂N-CH(iBu)-CO₂Me | 20 | VIa: Boc-NH-CH₂CH₂-NH-C(=O)-NH-CH(iBu)-CO₂Me | 78 |
| 2 | Ib | H₂N-iPr | 20 | VIb: Boc-NH-CH(Me)-CH₂-NH-C(=O)-NH-iPr | 85 |
| 3 | Id | H₂N-Ph | 20 | VIc: Boc-NH-CH(CH₂Ph)-CH₂-NH-C(=O)-NH-Ph | 87 |
| 4 | Id | HN-pyrrolidine-CONH₂ | 30 | VId: Boc-NH-CH(CH₂Ph)-CH₂-NH-C(=O)-N(pyrrolidine-CONH₂) | 89 |

[a]Reaction conditions: carbamate (3 mmol), amine (3–4 mmol), Hunig base (3 mmol), DMF (5 ml), ta.
[b]yield after purifiaction.

It is found that the carbamates (I) and (I bis) react with primary amines or amino acids in the presence of Hunig base at ambient temperature to give the corresponding urea derivatives (VI) with good yield (table 1, entry 1, 2). The reaction is very rapid and all the initial product is generally consumed in twenty minutes. The N-hydroxysuccinimide is the only secondary product formed during the reaction and is easily eliminated by aqueous washing. Under the same conditions, the aromatic amines such as aniline (entry 3) and a secondary amine (entry 4) also rapidly react with the carbamate (Id) to give the respective ureas (VIc) and (VId).

The repetitive formation of urea by using carbamates (I) and (I bis) as activated monomers permits obtaining urea oligomers as shown by the synthesis of Boc-A"CH₂-A"CH₂-i-Pr (VIe) and Boc-A"CH₂-A"CH₂-A"CH₂-i-Pr (VIf). (reaction 2).[9]

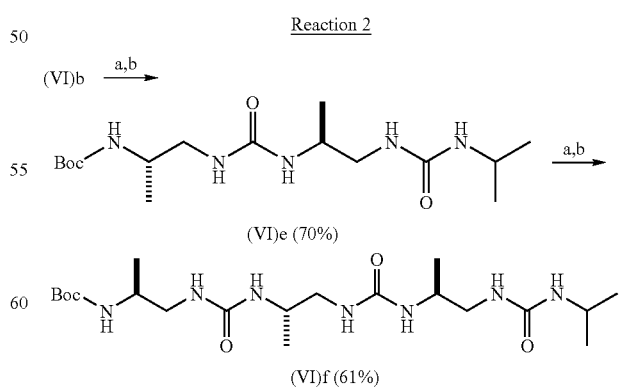

Reaction 2

Reagents (a) TFA; (b) (Ib), Hunig base, DMF.

In conclusion, the O-succinimidyl-β-(tert-butoxycarbonyl-amino)-carbamates (I) and (Ibis) are easily prepared from β-amino acids and react properly and with good yield with the primary and secondary amines to form urea derivatives. The mild conditions employed for the preparation of carbamates (I) and (Ibis) are compatible with most of the side chains of the natural amino acids and these stable intermediaries represent synthons attractive for the synthesis in solid phase of urea peptides and urea oligomers.

Experimental Section

Generalities

The amino acid derivatives have been bought from Neosystem or Novabiochem. THF is distilled with Na/benzophenone under argon before use. The toluene is distilled over $P_2O_5$ and preserved on a 4 Å molecular sieve. The aniline was passed through an alumina column before use. The Boc-$β^3$-amino acids were prepared according to procedures of the literature[10] by Arndt-Eistert homologation of the commercial protected amino acids. Reactions were conducted under argon pressure. The HPLC analysis was carried out on a Nucleosil $C_{18}$ column (5 m, 3.9×150 mm) by using a linear gradient of A (0.1% $CF_3COOH$ in $H_2O$) and B (MeCN) at a flow rate of 1.2 ml/min with UV detection at 214 nm.

General Procedure for the Preparation of O-succinimidyl carbamates (I) and (Ibis)

The N-protected β-amino acid (10 mmol) is dissolved in THF (30 ml) under argon and cooled to −20°. After addition of i-BuOCOCl (11 mmol) and NMM (11 mmol, 1.1 equivalent), the reaction mixture is agitated at −20° for 20 minutes. The resulting white suspension is reheated to −5°, and is treated with a 5 ml solution of $NaN_3$ (25 mmol). The mixture is then agitated for 5 minutes, diluted with EtOAc, washed with saturated NaCl, dried on $MgSO_4$ and concentrated under reduced pressure to give the acyl azide (XI) which is used without further purification. The toluene is then added under argon and the resulting solution is heated to 65° C. with agitation. Once the emission of gas has stopped (about 10 minutes), the N-hydroxysuccinimide (10 mmol) and the pyridine (10 mmol) are added. The mixture is agitated for 5 minutes at 65° C. and cooled to ambient temperature. In most cases, the desired product crystallizes in the toluene solution and is collected by filtration. Recrystallization in toluene permits obtaining pure O-succinimidyl carbamate. Otherwise, the solvent is evaporated under vacuum and the residue is purified by recrystallization in a suitable solvent.

O-succinimidyl-2-(tert-Butoxycarbonylamino)-ethyl-carbamate (Ia)

3-(tert-Butoxycarbonylamino) propanoic acid (3.78 g, 20 mmol) is transformed by following the general procedure. A recrystallization in toluene gives the compound (Ia) (3.3 g, 50%), constituted by colorless crystals; mp. 132–134° C.; HPLC $t_R$ 6.95 minutes (linear gradient, 20–80% B, 20 minutes); $^1$H-NMR (200 MHz, DMSO-$D_6$): 1.38 (s, 9H), 2.76 (s, 4H), 3.00–3.11 (m, 4H), 3.78–3.93 (m, 1H), 6.87 (br t, 1H); 8.27 (t, J=5.1 Hz, 1H). $^{13}$C-NMR (50 MHz, $CD_3CN$): 171.7, 157.5, 153.1, 79.7, 42.7, 40.6, 28.6, 26.3. MS (MALDI-TOF) (mass spectroscopy: matrix assisted laser desorption ionization—time of flight) m/z 340 [M+K]$^+$, 324 [M+Na]$^+$. Calculated analysis for $C_{12}H_{19}N_3O_6$: C, 47.84; H, 6.36; N, 13.95. Found: C, 48.09; H, 6.65; N, 14.00.

(S)-O-succinimidyl-2-(tert-Butoxycarbonylamino)-propylcarbamate (Ib)

Boc-$β^3$-HAla-OH (3.25 g, 16 mmol) is transformed by following the general procedure. Recrystallization in toluene gives the compound (Ib) (3.05 g, 60% which is a white solid; mp. 153–155° C.; $[α]_D^{r.t.}$−14.4 (c 1.03, MeCN); HPLC $t_R$ 8.00 min (linear gradient, 20–80% B, 20 min); $^1$H-NMR (200 MHz, $CD_3CN$): 1.07 (d, J=6.8 Hz, 3H) , 1.41 (s, 9H), 2.73 (s, 4H), 3.14–3.20 (m, 2H), 3.62–3.72 (m, 1H), 5.25 (br d, 1H), .6.54 (br t, 1H). $^{13}$C-NMR (50 MHz, $CD_3CN$): 171.7, 156.7, 153.3, 79.6, 47.7, 47.4, 28.7, 26.3, 18.4. Calculated analysis for $C_{13}H_{21}N_3O_6$: C, 49.52; H, 6.71; N, 13.33. Found: C, 49.45; H, 6.57; N, 13.18.

(S)-O-succinimidyl-2-(tert-butoxycarbonylamino)-(II)-methyl-butylcarbamate (Ic)

Boc-$β^3$-HVal-OH (1.27 g, 5.5 mmol) is transformed by following the general procedure. Recrystallization in toluene gives the compound (Ic) (956 mg, 51%) which is a white solid; mp. 125–127° C.; $[α]_D^{r.t.}$−41.2 (c=1.15,THF, $CHCl_3$); HPLC $t_R$ 10.80 min (linear gradient, 20–80% B, 20 min); $^1$H-NMR (200 MHz, $CD_3CN$): 0.89 (t, J=7.0 Hz, 6H) , 1.42 (s, 9H), 1.65–1.78 (m, 1H), 2.73 (s, 4H), 3.11–3.52 (m, 3H), 5.18 (br d, J=8.5 Hz, 1H), 6.46 (br t, 1H). $^{13}$C-NMR (50 MHz, $CD_3CN$): 171.7, 157.7, 153.5, 79.3, 56.7, 44.8, 31.0, 28.7, 26.3, 19.8, 18.3. MS (MALDI-TOF) m/z 383 [M+K]$^+$, 367 [M+Na]$^+$. Calculated analysis for $C_{15}H_{25}N_3O_6$: C, 52.47; H, 7.34; N, 12.24. Found: C, 52.26; H, 7.13; N, 11.92.

(S)-O-succinimidyl-2-(tert-butoxycarbonylamino)-4-phenyl-propylcarbamate (Id)

Boc-$β^3$-HPhe-OH (8.27 g, 29.5 mmol) is transformed by following the general procedure. Recrystallization in toluene gives the compound (Id) (6.6g, 57 which is a white solid; mp. 163–164° C.; $[α]_D^{r.t.}$−15 (c 1.17, MeCN); HPLC $t_R$ 12.79 min (linear gradient, 20–80% B, 20 min); $^1$H-NMR (200 MHz, $CD_3CN$): 1.33 (s, 9H), 2.68–2.90 (m, 6H), 3.16–3.37 (m, 2H), 3.78–3.93 (m, 1H), 5.26 (d, J=8.0 Hz, 1H), 6.54 (br t, 1H); 7.16–7.34 (m, 5H). $^{13}$C-NMR (50 MHz, $CD_3CN$): 171.7, 157.3, 153.3, 139.4, 130.3, 129.4, 127.4, 79.6, 53.2, 46.3, 39.0, 28.6, 26.3. MS (MALDI-TOF) m/z 430 [M+K]$^+$, 414 [M+Na]$^-$. Calculated analysis for $C_{19}H_{25}N_3O_6$: C, 58.30; H, 6.44; N, 10.74. Found: C, 58.17; H, 6.38; N, 10.69.

(S)-O-succinimidyl-3-(benzyloxycarbonyl)-2-(tert-butoxycarbonylamino)-propylcarbamate (Ie)

Boc-$β^3$-HAsp(Bzl)-OH (2.53 g, 7.5 mmol) is transformed by following the general procedure. Recrystallization in toluene gives the compound (Ie) (1.94 g, 58%) which is a white solid; mp. 115–117° C.; $[α]_D^{r.t.}$−16.3 (c 1.3, THF); HPLC $t_R$ 13.47 min (linear gradient, 20–80% B, 20 min); $^1$H-NMR (200 MHz, $CD_3CN$): 1.46 (s, 9H), 2.47–2.58 (m, 2H); 2.73 (s, 4H), 3.29 (t, J=6.2 Hz, 2H), 3.96–4.08 (m, 1H), 5.10 (s, 2H), 5.45 (br d, J=6.2 Hz, 1H); 6.54 (br t, 1H); 7.29–7.41 (m, 5H). $^{13}$C-NMR (50 MHz, $CD_3CN$): 26.3, 28.7, 37.6, 45.8, 48.9, 67.2, 80.0, 118.3, 129.1, 129.6, 137.3, 153.4, 156.5, 171.6, 171.7. MS (MALDI-TOF) m/z 488 [M+K]$^+$, 472 [M+Na]$^+$. Calculated analysis for $C_{21}H_{27}N_3O_8$: C, 56.12; H, 6.05; N, 9.35. Found: C, 55.89; H, 6.01; N, 9.32.

(S)-O-succinimidyl-3-(benzyloxy)-2-(tert-butoxycarbonylamino)-propylcarbamate (If)

Boc-$β^3$-HThr(Bzl)-OH (2.31 g, 7.14 mmol) is transformed by following the general procedure. Recrystallization in AcOEt/hexane gives the compound (If) (2.0 g, 64 which is a white solid; mp. 109–110° C.; $[α]_D^{r.t.}$+8.6 (c 1.07, $CH_3CN$); HPLC $t_R$ 14.59 min (linear gradient, 20–80% B, 20 min); $^1$H-NMR (200 MHz, $CD_3CN$): 1.16 (d, J=6.1 Hz, 3H), 1.43 (s, 9H), 2.73 (s, 4H), 3.21–3.44 (m, 2H), 3.61–3.76 (m, 2H), 4.51 (Abq, J=11.5 Hz, 2H), 5.21 (br d, J=9.1 Hz, 1H), 6.49 (br t, 1H), 7.25–7.39 (m, 5H). $^{13}$C-NMR (50 MHz, $CD_3CN$): 16.4, 26.3, 28.6, 44.1, 55.3, 71.5, 75.1, 128.5, 128.8, 129.3. MS (MALDI-TOF) m/z 475 [M+K]$^+$, 459 [M+Na]+. Calculated analysis for $C_{21}H_{29}N_3O_7$: C, 57.92; H, 6.71; N, 9.65. Found: C, 58.02; H, 6.67; N, 9.81.

O-succinimidyl-(2-nitrophenyl)carbamate (Ig) (see FIG. 1)

2-nitrobenzoic acid (1.17 g, 7 mmol) is transformed by following the general procedure. Recrystallization in AcOEt gives the compound (Ig) (1.39 g, 71%) which is present in the form of light yellow crystals; mp. 166–167° C.; HPLC $t_R$ 9.45 min (linear gradient, 20–80% B, 20 min); $^1$H-NMR (200 MHz, CDCl$_3$): 2.89 (s, 4H), 7.26 (dt, 1H), 7.69 (dt, 1H), 8.26 (dd, 1H), 8.40 (dd, 1H), 10.40 (br s). $^{13}$C-NMR (50 MHz, CDCl$_3$): 25.6, 120.8, 124.1, 126.2, 133.1, 136.2, 148.5, 169.2. MS (MALDI-TOF) m/z 318 [M+K]+, 302 [M+Na]+. Calculated analysis for $C_{12}H_{10}N_2O_6$: C, 47.32; H, 3.25; N, 15.05. Found: C, 47.45; H, 3.26; N, 15.07.

Formation of Ureas: General Procedure

O-succinimidyl carbamates (I) and (I bis) (1 mmol) and Hunig base (1 mmol) are added to a solution of the amine (1.3 mmol) in 5 ml DMF. After 10–30 minutes, the reaction mixture is diluted with saturated NaHCO$_3$, and extracted with AcOEt. The organic phase is washed with 1 N KHSO$_4$, saturated NaCl, NaHCO$_3$, saturated NaCl, dried (MgSO$_4$) and evaporated. Chromatography and/or recrystallization give the pure urea (VI).

Methyl (2S, 3R)-2-{[2-(tert-Butoxycarbonylamino) ethyl]-ureido}-3-methyl-pentanoate (Boc-G"CH$_2$-Leu-OMe, (VIa))

The carbamate (Ia) (602 mg, 2 mmol) is treated with HCl.H-Leu-OMe (436 mg, 2.4 mmol) following the general procedure. Recrystallization in EtOAc/diisopropylether gives (VIa) (520 mg, 78%) which is present in the form of colorless needles; mp. 86–89° C.; $[\alpha]_D^{r.t.}$–10.8 (c 1.02, MeOH); HPLC $t_R$ 11.39 min (linear gradient, 20–80% B, 20 min); $^1$H-NMR (200 MHz, CDCl$_3$): 0.90 (d, J=6.4 Hz, 3H), 0.91 (d, J=6.2 Hz, 3H), 1.41 (s, 9H), 1.45–1.75 (m, 3H), 3.16–3.32 (m, 4H), 3.69 (s, 3H), 4.36–4.47 (m, 1H), 5.34 (br t, J=5.2, 1H), 6.14 (d, J=8.2, 1H), 6.76 (br t, J=5.0, 1H). $^{13}$C-NMR (50 MHz, CDCl$_3$): 21.9, 22.9, 24.8, 28.4, 40.3, 41.3, 41.8, 51.7, 52.1, 79.4, 156.7, 158.5, 175.3. MS (MALDI-TOF) m/z 370 [M+K]+, 354 [M+Na]+, 332 [M+1]+. Calculated analysis for $C_{15}H_{29}N_3O_5$: $H_2O$: C, 52.94; H, 8.82; N, 12.35. Found: C, 52.92; H, 8.68; N, 12.27.

(2S)-1-[2-(tert-Butoxycarbonylamino)-propyl]-3-(1-methyl-ethyl)-urea (Boc-A"CH$_2$-i-Pr, (VIb))

The carbamate (Ib) (901 mg, 2.86 mmol) is treated with i-PrNH$_2$ (511 l, 6 mmol) according to the general procedure to give (VIb) (701 mg, 95%) which is a white solid; mp. 101° C.; $[\alpha]_D^{r.t.}$–7.4 (c 0.89, MeOH); HPLC $t_R$ 8.71 min (linear gradient, 20–80% B, 20 min); $^1$H-NMR (200 MHz, CD$_3$CN): 1.03 (d, J=6.6 Hz, 3H), 1.07 (d, J=6.5 Hz, 6H), 1.40 (s, 0 9H), 3.02–3.08 (m, 2H), .3.47–3.60 (m, 1H), 3.65–3.81 (m, 1H), 4.92 (br d, 1H), 5.1 (br t, 1H), 5.66 (br, 1H); $^{13}$C-NMR (50 MHz, CD$_3$CN): 158.4, 156.4, 79.4, 47.7, 46.2, 42.2, 28.5, 23.4, 23.3, 18.6. MS (MALDI-TOF) m/z 298 [M+K]+, 282 [M+Na]+. Calculated analysis for $C_{12}H_{25}N_3O_3$: C, 55.57; H, 9.72; N. 16.20. Found: C, 55.56; H, 9.82; N, 16.16.

(2S)-1-[2-(tert-Butoxycarbonylamino)-3-phenyl-propyl]-3-phenyl-urea (Boc-F"CH$_2$-Ph, (VIc))

The carbamate (Id) (500 mg, 1.28 mmol) is treated with PhNH$_2$ (119 mg, 1.28 mmol) according to the general procedure. A recrystallization in CH$_2$Cl$_2$/hexane gives (VIc) (412 mg, 87%) which is a white solid. mp. 154° C.; $[\alpha]_D^{r.t.}$+10.3 (c 1.03, MeOH); HPLC $t_R$ 15.23 min (linear gradient, 20–80% B, 20 min); $^1$H-NMR (400 MHz, CD$_3$OD): 1.35 (s, 9H), 2.70 (dd, J=8.0, 13.7 Hz, 1H), 2.80 (dd, J=7.8, 13.7 Hz, 1H), 3.16 (dd, J=8.6, 13.6 Hz, 1H), 3.33 (dd, J=4.6, 17.1 Hz, 1H) , 3.81–3.85 (m, 1H) , 7.16–7.34 (m, 10H) $^{13}$C-NMR (400 MHz, CD$_3$OD): 158.8, 158.6, 141.3, 140.1, 130.8, 130.2, 129.8, 127.7, 123.9, 120.7, 80.4, 54.6, 44.8, 40.3, 29.1, 28.8. MS (MALDI-TOF) m/z 408 [M+K]+, 392 [M+Na]+, 370 [M+1]+. Calculated analysis for $C_{21}H_{27}N_3O_3$: C, 68.27; H, 7.37; N, 11.37. Found: C, 68.19; H, 7.32; N, 11.47.

Boc-F"CH$_2$-Pro-NH$_2$, (VId)

The carbamate (Id) (1.16 g, 3 mmol) is treated with HCl.H-Pro-NH$_2$ (540 mg, 3.6 mmol) ) according to the general procedure. A chromatography (CHCl$_3$/MeOH 10:1) gives (VId) (1.16 g, 88%) which is a white solid; mp. 96–98° C.; $[\alpha]_D^{r.t.}$–20.4 (c 1.02, MeOH); HPLC $t_R$ 10.02 min (linear gradient, 20–80% B, 20 min); $^1$H-NMR (200 MHz, CD$_3$OD): 1.36 (s, 9H), 1.88–2.17 (m, 4H), 2.59–2.83 (m, 2H), 2.96 (dd, J=9.4, 13.6 Hz, 1H), 3.21–3.50 (m, 3H), 3.89–3.99 (m, 1H), 4.29 (dd, J=3.2, 8.1 Hz, 1H), 7.11–7.29 (m, 5H). $^{13}$C-NMR (200 MHz, CDCl$_3$): 24.7, 28.4, 28.8, 39.0, 45.7, 46.3, 51.6, 60.1, 79.6, 126.6, 128.6, 129.2, 137.4, 156.6, 157.8, 175.4. MS (MALDI-TOF) m/z 429 [M+K]+, 413 [M+Na]+, 391 [M+1]+. Calculated analysis for $C_{20}H_{30}N_4O_4$: C, 61.52; H, 7.74. Found: C, 61.78 H, 7.77.

Boc-A"CH$_2$-A"CH$_2$-i-Pr, (VIe)

The product (VIb) (650 mg, 2.5 mmol) is dissolved in CF3COOH (0.25M) at 0°. After agitation at ambient temperature for 30 minutes and concentration under reduced pressure, the trifluoroacetate salt is dried under vacuum under KOH and used without further purification.

The carbamate (Ib) is treated with a solution of trifluoroacetate salt according to the general procedure. Recrystallization in EtOH/hexane gives (VIe) (630 mg, 70%) which is a white solid. mp. 184–185° C., $[\alpha]_D^{r.t.}$ +9.3 (c 0.88, MeOH); HPLC $t_R$ 8.52 min (linear gradient, 20–80% B, 20 min); $^1$H-NMR (200 MHz, CD$_3$OD): 1.05–1.12 (m, 12H), 1.42 (s, 9H), 2.92–3.24 (m, 4H), .3.56–3.84 (m, 2H); $^{13}$C-NMR (100 MHz, CD$_3$OD): 160.9, 160.7, 158.2, 80.0, 48.2, 47.8, 46.8, 46.4, 42.9, 28.5, 23.6, 23.5, 19.1, 18.6. Calculated analysis for $C_{16}H_{33}N_5O_4$: C, 53.46; H, 9.25; N, 19.48. Found: C, 53.62; H, 9.29; N, 19.43.

Boc-A"CH$_2$-A"CH$_2$-A"CH$_2$-i-Pr, (VIf)

The product (VIe) (440 mg, 1.22 mmol) is dissolved in CF$_3$COOH (0.25M) at 0°. After agitation at ambient temperature and concentration under reduced pressure the trifluoroacetate salt, which precipitates by addition of Et$_2$O, is collected by filtration, dried under vacuum under KOH and is used without further purification.

To a solution of this salt in DMF are added successively (Ib) and Hunig base (637 l, 3.66 mmol). The reaction mixture is agitated for 20 minutes and saturated NaHCO$_3$ is added. The precipitate which forms is filtered, washed with saturated NaHCO$_3$, water, and Et$_2$O and is dried under vacuum on P$_2$O$_5$ to give (VIf) (350 mg, 62%) which is a white solid. mp. 210–211° C., $[\alpha]_D^{r.t.}$ 63.6 (c 1.00, MeOH); HPLC $t_R$ 8.53 min (linear gradient, 20–80% B, 20 min) $^1$H-NMR (200 MHz, CD$_3$OD): 1.03–1.12 (m, 15H) , 1.44 (s, 9H) , 2.55–2.85 (m, 3H), 3.21–3.39 (m, 3H), 3.61–3.95 (m, 4H); $^{13}$C-NMR (100 MHz, CD$_3$OD): 161.2, 161.1, 160.9, 158.7, 80.3, 48.2, 47.6, 47.5, 47.2, 47.1, 46.8, 43.0, 29.0, 23.8, 23.7, 19.5, 19.0, 18.7. MS (MALDI-TOF) m/z 499 [M+K]+, 483 [M+Na]+, 461 [M+1]+. Calculated analysis for $C_{20}H_{41}N_7O_5$: C, 52.27; H, 8.99; N, 21.33. Found: C, 52.23; H, 9.00; N, 20.93.

EXAMPLE II

Preparation of O-succinimidyl-2-[(9H-fluoren-9-yl-ethoxy)carbonylamino]-ethylcarbamate Derivatives from β-Amino Acids and Application to the Synthesis in Solid Phase of Oligoureas and of Pseudopeptide Urea 1) Preparation of O-succinimidyl carbamates (I) and (I bis)

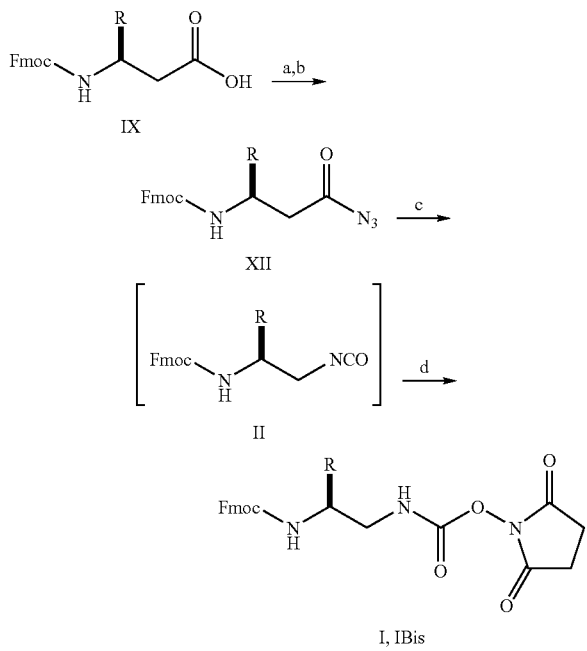

Reaction 1. Reagents and conditions: a) EtOCOCl, NMM, THF, −15° C., 15 min; (b) NaN$_3$, H$_2$O, 5 min (c) Toluene, 65° C.; (d) N-hydroxysuccinimide, pyridine, 65° C., 5 min.

In accordance with reaction 1, the N-Fmoc-protected β-amino acids (IX) comprising side chains of natural amino acids Ala, Val, Leu, Phe, Tyr, et Lys are converted into the corresponding acyl azides (XII) by reaction of their mixed anhydride (formed with EtOCOCl/N-methyl morpholine (NMM)) with an aqueous solution of NaN$_3$ (2.5 equiv). The intermediate isocyanates (II) obtained by Curtius rearrangement on (XII) (toluene, 65° C., 5 to 15 min) are immediately treated with N-hydroxysuccinimide (1 equivalent) in the presence or not of pyridine (1 equivalent) to give the carbamates (I) and (Ibis) as crystalline products (see the yield in Table 1). As in the case of the Boc derivatives (see example 1), this reaction sequence is generally complete in 1 hour. As has been shown for the Boc-protected derivatives, the carbamates (I) and (Ibis) precipitate or recrystallize directly from the toluene solution and are simply collected by filtration. In the case of these Fmoc protected derivatives, the yields obtained (51–86%) are better than with the corresponding Boc derivatives.

Similarly, these carbamates (I) and (Ibis) can be stored at ambient temperature or at 4° C. without noticeable degradation.

Table 1 shows the conversion of β-amino acids (IX) into the corresponding O-succinimidyl carbamates (I) and (I bis).

| R = | Carbamates (I) and (Ibis) | Yield (%)[a] | mp (° C.) | $[\alpha]^{25}_D$ (c, DMF) | HPLC t$_R$ (min)[b] |
|---|---|---|---|---|---|
| Me | Ih | 86 | 161–163 | −3.6 (c = 1.08) | 10.44 |
| iPr | Ii | 69 | 109–111 | +5.9 (c = 1.18) | 11.84 |
| iBu | Ij | 51 | 134–137 | −10.8 (c = 1.01) | 12.63 |
| Bn | Ik | 66 | 175–177 | −26.1 (c = 1.13) | 12.48 |
| Bn(OtBu) | Il | 78 | 138–140 | −22.9 (c = 1.12) | 13.87 |
| (CH$_2$)$_4$NH(Boc) | Im | 79 | 122–124 | −4.7 (c = 1.16) | 12.67 |

[a]Yield of (I) and (I bis) after recrystallization from toluene.
[b]linear gradient of A (0.1% TFA in H$_2$O) and B (MeCN containing 0.08% TFA), 30–100% B, 20 min.

Procedure for obtaining O-succinimidyl carbamates (I) and (I bis)

The N-protected β-amino acid (10 mmol) is dissolved in THF (30 ml) under Ar and cooled to −20°. After addition of i-BuOCOCl (11 mmol) and NMM (11 mmol, 1.1. equivalent), the reaction mixture is agitated at −20° for 20 minutes. The resulting white solution is reheated to −5°, and is treated with a solution (5 ml) of NaN$_3$ (25 mmol). The mixture is then agitated for 5 minutes, diluted with EtOAc, washed with saturated NaCl, dried on MgSO$_4$ and concentrated under reduced pressure to give the acyl azide which is used without further purification. Toluene is then added under argon and the resulting solution is heated to 65° C. with agitation. Once the emission of gas has ceased (about 10 minutes), the N-hydroxysuccinimide (10 mmol) and the pyridine (10 mmol) are added. The mixture is agitated for 5 minutes at 65° C. and cooled to ambient temperature. In most cases, the desired product crystallizes in the toluene solution and is collected by filtration. Recrystallization in toluene permits obtaining pure O-succinimidyl carbamate. Otherwise, the solvent is evaporated under vacuum and the residue is purified by recrystallization in the appropriate solution.

2) Application to synthesis on a solid support

With monomers (Ih)–(Im), the aim was the preparation of ureidopeptide (VIIa) and oligoureas (VIIb)–(VIId) containing six to nine urea linkages.

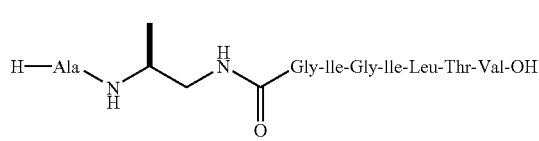

VIIa

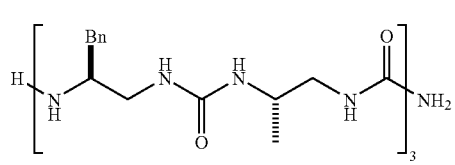

VIIb

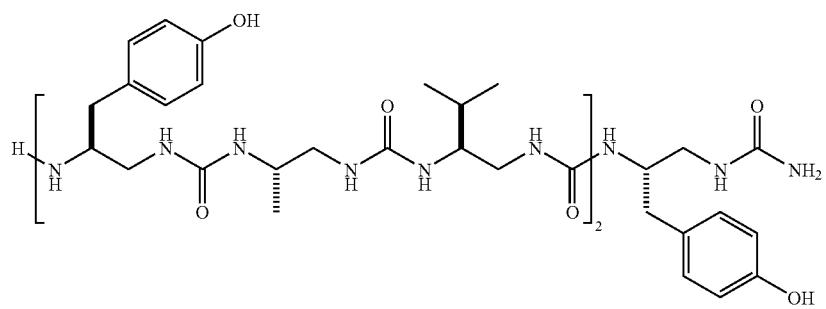

VIIc

H-β³-HTyr^u-β³-HLys^u-β³-HLeu^u-β³-HVal^u-β³-
HPhe^u-β³-HLys^u-β³-HAla^u-β³-HVal^u-β³-HTyr^u-
NH₂      VIId (The abbreviations used for the derivative (VIId) are defined in reference 9).

Incorporation of a urea structure in a peptide

The peptide sequence selected by way of example is that of the tumoral antigen MART(27–35) of the sequence:

H-Ala-Ala-Gly-Tle-Gly-Ile-Leu-Thr-Val-OH.

The use of the carbamate (Ih) has permitted the introduction of a urea structure between Ala$^{28}$ and Gly$^{29}$.

The synthesis in solid phase of the peptide up to Gly$^{29}$ is carried out by Fmoc chemistry (Fluorenyl methoxycarbonyl) on a scale of 100 moles by starting with a Wang resin (p-benzyloxybenzyl alcohol) substituted with valine according to conventional methods of synthesis of peptides in solid phase (References: Methods in Enzymology, Vol. 89, Solid Phase Peptide Synthesis, Ed: G. B. Fields, Academic Press, NY, USA). After deprotection of the Fmoc group of Gly$^{29}$ with 20% piperidine in DMF, the carbamate (Ih) (5 equivalents) dissolved in DMF followed by diisopropylethylamine (5 equivalents) are added to the resin, and the reaction is left to proceed for 45 minutes. This operation can if desired be repeated once. After washing and rinsing of the resin, the Fmoc group is deprotected as above, and Fmoc-Ala-OH is coupled to the resin by using methods described in. the literature (references: Methods in Enzymology, Vol. 89, Solid Phase Peptide Synthesis, Ed: G. B. Fields, Academic Press, NY, USA).

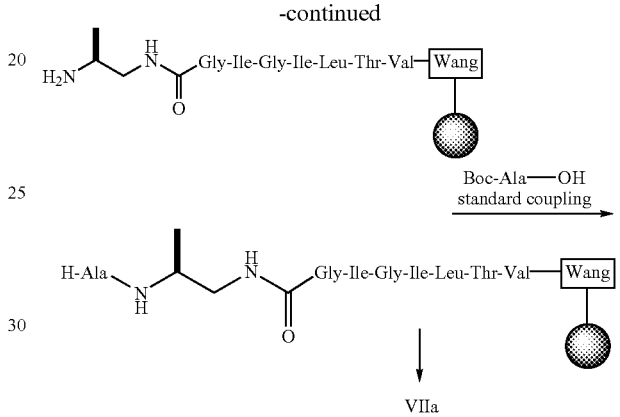

After cleaving the resin by conventional protocols used in peptide synthesis in solid phase (references: Methods in Enzymology, Vol. 89, Solid Phase Peptide Synthesis, Ed. G. B. Fields, Academic Press, NY, USA) , the desired crude product (VIIa) is obtained after lyophilization with a purity of 73% (by HPLC) (see table 2 below). After purification by HPLC and lyophilization, the product is obtained with a purity of 99.2%. The pure product is characterized by mass spectrometry (MALDI-MS) and by HPLC.

Synthesis of Urea Oligomers from O-succinimidyl Carbamates of Formula (I) and (I bis)

The general synthesis reaction of oligoureas (VIb)-(VId) is shown in reaction 2. The products (VIIB)-(VIId) have been synthesized in solid phase from a commercial Rink amide resin (4-(2',4'-dimethoxyphenyl-Fmoc-amino-methyl phenoxyacetamido-4-methylbenzhydrylamine resin) (0.60 mequiv/g) on a sale of 100 μmole.

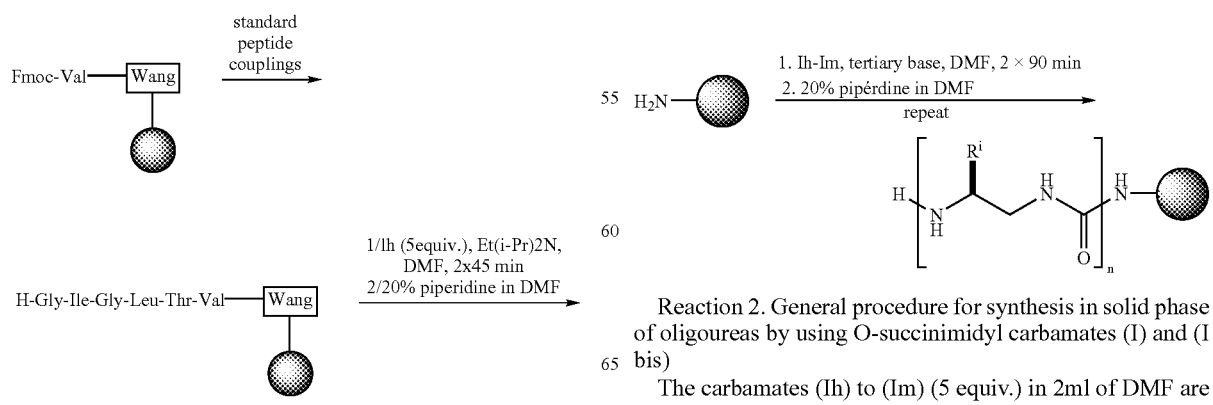

Reaction 2. General procedure for synthesis in solid phase of oligoureas by using O-succinimidyl carbamates (I) and (I bis)

The carbamates (Ih) to (Im) (5 equiv.) in 2ml of DMF are added to a suspension of the resin in DMF (2 ml) followed by diisopropylethylamine (5 equiv.). The reaction is left to run 90 minutes and repeated, after filtration of the resin. The Fmoc group is then cleaved by treated with 20% piperidine in DMF. The washing and filtration techniques of the resin as well as the deprotection of the Fmoc group are those currently used in peptide synthesis in solid phase. The whole operation (coupling and deprotection of the Fmoc) is repeated several times with carbamates (Ih) and (Im) alternating, to give, after cleavage of the resin (standard cleavage used in peptide synthesis in solid phase with the Fmoc strategy) the crude products (VIIb) to (VIId) with good yield.

The purity of the crude products is given in Table 2 below. The HPLC purification on a C18 column, followed by lyophilization, gives pure products (VIIb)–(VIId) with an overall yield comprised between 20 and 50% (Entries 1–4 of Table 2).

TABLE 2

Characterization of ureidopeptide (VIIa) and oligoureas (VIIb)–(VIId).

| Entry | Product | Base | HPLC crude purity (%) | Global yield (%)[a] | HPLC $t_R$ (min)[b] | MALDI-TOF MS |
|---|---|---|---|---|---|---|
| 1 | VIIa | DIEA | 73 | 50 | 12.57[c] | 842.9 $[M + H]^+$ |
| 2 | VIIb | DIEA | 63 | 42 | 10.86[d] | 846.8 $[M + H]^+$ |
| 3 | VIIc | DIEA | 51 | 38 | 14.58[c] | 1051.5 $[M + H]^+$ |
| 4 | VIId | DIEA | 35 | 20 | 15.14[c] | 1393.0 $[M + H]^+$ |
| 5 | VIIc | NMM | 66 | 57 | 14.70[c] | 1073.2 $[M + Na]^+$ |
| 6 | VIIc | — | 61 | 55 | 14.59[c] | 1072.8 $[M + Na]^+$ |

[a]after purification and lyophilization.
[b]linear gradient of A (0.1% TFA in $H_2O$) and B (MeCN containing 0.08% TFA).
[c]5–65% B, 20 min.
[d]20–80% B, 20 min.

The quantity of impurities present in the raw product of synthesis increases with the size of the oligomer. Analysis by MALDI-TOF-MS shows that the principal impurities isolated by HPLC on a C18 column arise either from deletions (products of lower mass that can result from incomplete couplings or else incomplete deprotection of the Fmoc group in the latter stages of synthesis), or more surprisingly by double insertion of monomers. A study of the stability of the carbamates (Ih)–(Im) in the solutions of DMF containing 5% diisopropylethylamine (DIEA) shows substantial degradation as well as partial cleavage of the Fmoc group. Based on these results, more gentle conditions for the reaction have been evaluated. On the one hand, the use of a weaker tertiary base such as N-methyl morpholine (NMM) gives better results (entry 5 of table 2). On the other hand, it has been shown that the use of a tertiary base was not necessary because good results are obtained in the absence of a base by using identical reaction times (see entry 6 of table 2).

In conclusion, there has been described an effective method for the preparation of optically active O-succinimidyl-(9H-fluoren-9-ylmethoxycarbonylamino)-ethyl carbamate derivatives (Ih)–(Im) and their use as activated monomers in the synthesis in solid phase of oligoureas.

EXAMPLE III

Preparation of O-succinimidyl Carbamate Derivatives (III) and (III bis) from N-protected Dipeptides and Application to the Synthesis of Ureido Peptide and Hybrid Peptide/Oligoureas 1) Preparation of O-succinimidyle carbamates (III) and (III bis)

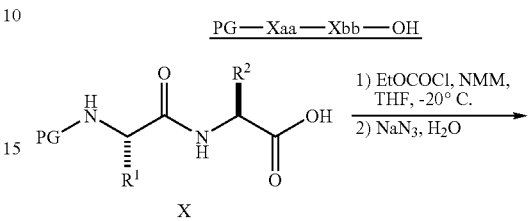

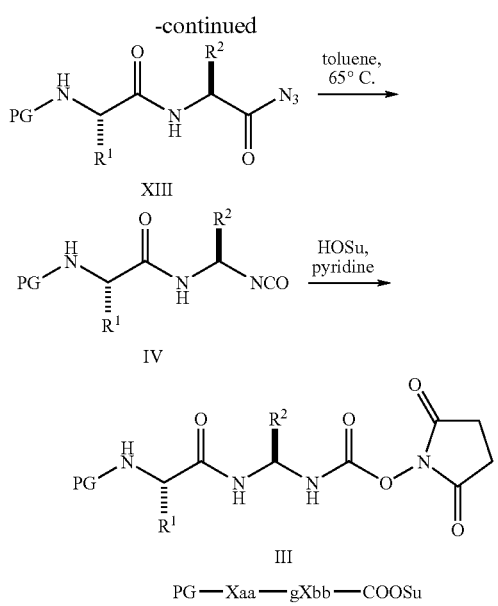

Reaction 1: Synthesis of O-succinimidyl derivatives (III) and (III bis) from N-protected dipeptides.

In accordance with reaction 1, the N-Boc or N-Fmoc protected dipeptides (X) comprising side chains of natural amino acids Ala, Val, Leu, Phe, Tyr, and Lys, are converted into corresponding acyl azides (XIII) by reaction of their mixed anhydride (formed with EtOCOCl/N-methyl morpholine (NMM) with an aqueous solution of $NaN_3$ (2.5 equivalent).

The intermediate isocyanates (IV) obtained by Curtius rearrangement on (XIII) (toluene, 65° C., 5 to 15 minutes) are immediately treated with N-hydroxysuccinimide (1 equivalent) in the presence or not of pyridine (1 equivalent) to give carbamates (III) and (III bis) as crystalline products (see the yields in Table 1). As in examples I and II, this reaction sequence is generally complete in 1 hour. As has been shown for the Boc-protected β-amino acid derivatives, the carbamates (III) and (III bis) precipitate or recrystallize directly from the toluene solution and are simply collected by filtration. In the case of dipeptide derivatives, the yields obtained (52–93%) are good to excellent.

Similarly, these carbamates (III) and (III bis) can be stored at ambient temperature or at 4° C. without notable degradation.

TABLE 1

Conversion of dipeptides (X) into the corresponding O-succinimidyl carbamates (III) and (III bis).

| Original Dipeptides | Carbamates (III) and (III bis) | Yield (%)[a] | HPLC $t_R$ (min)[b] | MALDI-TOF MS |
|---|---|---|---|---|
| Boc-Gly-Ile-OH | IIIa | 87 | 9.13[c] | — |
| Boc-Pro-Val-OH | IIIb | 72 | 11.79[c] | — |
| Boc-Phe-Leu-OH | IIIc | 82 | 14.01[c] | 513.46 [M + Na]+ |
| Boc-Ile-Val-OH | IIId | 62 | 13.46[e] | — |
| Boc-Lys-Val-OH | IIIe | 69 | 14.98[c] | — |
| Boc-Pro-Leu-OH | IIIf | 76 | 12.73[e] | — |
| Boc-Phe-Pro-OH | IIIg | 80 | | — |
| Fmoc-Ile-Leu-OH | IIIh | 93 | 12.85[d] | 601.29 [M + Na]+ |
| Fmoc-Phe-Ala-OH | IIIi | 86 | 11.45[d] | 593.32 [M + Na]+ |
| Fmoc-Ile-Gly-OH | IIIj | 52 | 10.94[d] | 545.05 [M + Na]+ |

[a]yields of (III) and (III bis) after recrystallization from toluene.
[b]linear gradient of A (0.1% TFA in $H_2O$) and B (MeCN containing 0.08% TFA),
[c]20–80% B, 20 min,
[d]30–100% B, 20 min,
[e]0–100% B, 20 min.

Procedure for Obtaining O-succinimidyl carbamates (III) and (III bis)

The N-protected dipeptide (10 mmol) is dissolved in THF (30 ml) under Ar and cooled to –20°. After addition of i-BuOCOCl (11 mmol) and NMM (11 mmol, 1.1 equivalent), the reaction mixture is agitated at –20° for 20 minutes. The resulting white solution is reheated to –5°, and is treated with a solution (5 ml) of $NaN_3$ (25 mmol). The mixture is then agitated for 5 minutes, diluted with EtOAc, washed with saturated NaCl, dried on $MgSO_4$, and concentrated under reduced pressure to give the acyl azide which is used without further purification. The toluene is then added under argon and the resulting solution is heated 65° C. with agitation. Once the generation of gas has stopped (about 10 minutes), the N-hydroxysuccinimide (10 mmol) and the pyridine (10 mmol) are added. The mixture is agitated for 5 minutes at 65° C. and cooled to ambient temperature. In most cases, the desired product crystallizes from the toluene solution and is collected by filtration. Recrystallization in toluene permits obtaining pure O-succinimidyl carbamate. Otherwise, the solvent is evaporated under vacuum and the residue is purified by recrystallization in the suitable solvent.

Experimental Section
General Remarks:
HPLC analyses have been carried out on a $C_{18}$ column (5 μm, 3.9×150 mm by using a gradient of A (0.1% TFA in $H_2O$) and B (0.08% TFA in MeCN) at a flow rate of 1.2 ml/min with UV detection at 214 nm.

Boc-Gly-gIle-COOSu (IIIa):
Yield 87% white solid; HPLC $t_r$ 9.13 (linear gradient, 20–80% B, 20 min)—$^1$H RMN ([$D_6$]DMSO, 200 MHz): δ=0.79–0.95 (m, 6H, $CH_3$—CH—$CH_2$—$CH_3$), 0.98–1.14 (m, 2H, $CH_3$—CH—$CH_2$—$CH_3$), 1.38 (s, 9H, C($CH_3$)$_3$), 1.60–1.78 (m, 1H, $CH_3$—CH—$CH_2$—$CH_3$), 2.77 (s, 4H, $CH_2$—$CH_2$), 3.50–3.68 (m, 2H, $NHCH_2CO$), 5.00–5.20 (m, 1H, NH—CH—NH), 6.90–7.00 (m, 1H, $NHCO_2C(CH_3)_3$), 7.99 (d, J=8.6 Hz, 1H, $NHCO_2SU$), 8.54 (d, J=8.0 Hz, 1H, NHCOCH). —$^{13}$C RMN ([$D_6$]DMSO, 50 MHz): δ=170.7 (CO), 168.7 (CO), 155.7 (CO), 150.8 (CO), 78.0 (C), 61.4 (CH), 43.0 ($CH_2$), 38.1 (CH), 28.0 ($CH_3$), 25.2 ($CH_2$), 24.3 ($CH_2$), 14.2 ($CH_3$), 10.7 ($CH_3$).

Boc-Phe-gLeu-COOSu (IIIc):
Yield 82% white solid; HPLC $t_r$ 14.01 (linear gradient, 20–80% B, 20 min)—$^1$H RMN ([$D_6$]DMSO, 200 MHz): δ=0.87 (d, J=5.4 Hz, 3H, $CH_3$), 0.88 (d, J=5.4 Hz, 3H, $CH_3$), 1.29 (s, 9H, C($CH_3$)$_3$), 1.50–1.73 (m, 3H, CH—$CH_2$—CH—($CH_3$)$_2$), 2.64–2.98 (m, 2H, $CH_2$—$C_6H_5$), 2.76 (s, 4H, $CH_2$—$CH_2$), 4.04–4.21 (m, 1H, CHCO), 5.32 (m, 1H, NHCHNH), 6.85 (d, J=8.6 Hz, 1H, $NHCO_2C(CH_3)_3$), 7.10–7.30 (m, 5H, $C_6H_5$), 8.25 (d, J=8.3 Hz, 1H, $NHCO_2Su$), 8.65 (d, J=7.5, 1H, NHCOCH). —$^{13}$C RMN ([$D_6$]DMSO, 50 MHz): δ=171.0 (C), 170.7 (C), 155.2 (C), 150.2 (C), 138.1 (C), 129.2 (CH), 127.9 (CH), 126.1 (CH), 77.9 (C), 56.4 (CH), 55.5 (CH), 42.9 ($CH_2$), 37.1 ($CH_2$), 28.0 ($CH_3$), 25.2 ($CH_2$), 23.8 (CH), 22.2 ($CH_3$), 21.9 ($CH_3$).

Boc-Lys(2ClZ)-gVal-COOSu (IIIe)
Yield 69% white solid; HPLC $t_r$ 14.98 (linear gradient, 20–80% B, 20 min)—$^1$H RMN ([$D_6$]DMSO): δ=0.84 (d, J=6.2 Hz, 3H, Me), 0.87 (d, J=5.4 Hz, 3H, Me), 1.15–1.57 (m, 6H, $CHCH_2CH_2CH_2$), 1.34 (s, 9H, t-Bu), 1.72–1.98 (m, 1H, $Me_2CH$), 2.72 (s, 4H, $CH_2CO$), 2.85–3.08 (m, 2H, $CH_2NH$), 3.78–3.92 (m, 1H, NHCHCO), 4.87–4.99 (m, 1H, NHCHNH), 5.06 (s, 2H, $OCH_2$), 6.82 (d, J=8.2 Hz, 1H, $NHCO_2$(t-Bu)), 7.24–7.50 (m, 5H, H arom.), 7.93 (d, J=8.7 Hz, 1H, $NHCO_2Su$), 8.54 (d, J=7.9 Hz, 1H, CHCONHCH). —$^{13}$C RMN ([$D_6$]DMSO, 50 MHz): δ=171.6, 170.6, 150.9, 150.8, 134.5, 132.0 (C), 129.6, 129.2, 127.2 (CH), 77.9 (C), 62.8 (CH), 62.4 ($CH_2$), 54.1 (CH), 40.0 ($CH_2$), 31.8 (CH), 31.2, 29.0 ($CH_2$), 28.1 ($CH_3$), 25.2, 22.7 ($CH_2$), 18.2, 18.0 ($CH_3$).

Fmoc-Phe-gAla-COOSu (IIIi)
Yield 86% white solid; HPLC $t_r$ 11.45 (linear gradient, 30–100% B, 20 min)—$^1$H RMN ([$D_8$]DMSO, 200 MHz): δ=1.31 (d, J=6.5 Hz, Me), 2.65–2.77 (m, 5H, $CH_2CO$, $NCHCH_2$), 2.75 (br dd, 1H, $NCHCH_2$), 4.04–4.25 (m, 4H, $CHCH_2O$, CHCO), 5.31 (m, 1H, NHCHNH), 7.13–7.41 (m, 9 arom. H), 7.47–7.63 (m, 3H, arom. H, $NHCOO_2Fm$), 7.84 (d, J=7.3 Hz, 2 arom. H), 8.53 (d, J=7.8 Hz, 1H, $NHCO_2Su$), 8.72 (d, J=7.0 Hz, 1H, CHCONHCH). —$^{13}$C RMN ([$D_6$] DMSO, 50 MHz): δ=170.7, 155.7, 150.3, 143.7, 140.6, 138.2 (C), 129.1, 127.9, 127.5, 127.0, 126.1, 125.2, 120.0 (CH), 65.5 ($CH_2$), 55.8, 54.5, 46.5 (CH), 37.3, 25.2 ($CH_2$), 20.5 ($CH_3$).

Fmoc-Ile-gGly-COOSu (IIIj)
Yield 52% white solid; HPLC $t_r$ 10.94 (linear gradient, 30–100% B. 20 min)—$^1$H RMN ([$D_6$]DMSO, 200 MHz): δ=0.80 (t, J=7.0 Hz, 3H, Me), 0.83 (d, J=6.6 Hz, 3H, Me), 1.01–1.23 (m, 1H, $CH_2Me$), 1.34–1.50 (m, 1H, $CH_2Me$), 1.59–1.82 (m, 1H, CHMe), 2.76 (s, 4H, $CH_2CO$), 3.91 (t, J=8.0 Hz, 1H, CHCH₂O), 4.22–4.30 (m, 3H, CHCH₂O, NHCH), 4.35–4.55 (m, 2H, NHCH₂), 7.28–7.46 (m, 4H, arom. H, NHCO₂Fm), 7.75 (d, J=6.9 Hz, 2 arom. H), 7.89 (d, J=7.0 Hz, 2 arom. H), 8.69 (br. t, J=5.6 Hz, 1H, NHCO₂Su), 9.00 (br. t, J=8.0 Hz, 1H, CHCONHCH₂). —¹³C RMN ([D₆]DMSO, 50 MHz): δ=171.7, 170.6, 155.8, 151.9, 143.7, 140.6 (C), 127.5, 126.9, 125.3, 120.0 (CH), 65.6 (CH₂), 58.8, 46.6 (CH), 45.6 (CH₂), 36.3 (CH), 25.2, 24.3 (CH₂), 15.2, 10.7 (CH₃).

Boc-Pro-gLeu-COOSu (IIIf)

Yield 76% white solid; HPLC t$_r$ 10.59 (linear gradient, 20–80% B, 20 min)—¹H RMN ([D₆]DMSO, 200 MHz): δ=0.83 (d, J=6.0 Hz, 6H, CH—(CH₃)₂), 1.28, 1.34 (s, 9H, C(CH₃)₃), 1.45–1.52 (m, 3H, CH—CH₂—CH—(CH₃) 2), 1.59–2.05 (m, 4H, CH₂—CH₂—CH₂—CH), 2.72 (s, 4H, CH₂—CH₂), 3.14–3.36 (m, 2H, N—CH₂—CH₂), 4.02–4.05 (m, 1H, NCHCO), 5.17–5.27 (m, 1H, NHCHNH), 8.19 (d, J=8.0 Hz, 1H, NHCO₂Su), 8.57 (d, J=7.3, 1H, NHCOCH). —¹³C RMN ([D₆]DMSO, 50 MHz): δ=171.73 (C), 171.69 (C), 153.18 (C), 150.45 (C), 78.26 (C), 59.14 (CH), 56.35 (CH), 46.40 (CH₂), 42.78 (CH₂), 30.88 (CH₂), 27.91 (CH₃), 25.20 (CH₂), 23.82 (CH), 22.85 (CH₂), 22.27 (CH₃), 21.87 (CH₃).

Boc-Pro-gVal-COOSu (IIIb)

Yield 72% white solid; HPLC t$_r$ 8.98 (linear gradient, 20–80% B, 20 min)—¹H RMN ([D₆]DMSO, 200 MHz): δ=0.87 (d, J=6.4 Hz, 6H, CH—(CH₃)₂), 1.31, 1.37 (s, 9H, C(CH₃)₃), 1.74–2.07 (m, 5H, CH—CH—(CH₃)₂, CH—CH₂—CH₂—CH₂), 2.74 (s, 4H, CH₂—CH₂), 3.17–3.32 (m, 2H, N—CH₂—CH₂), 4.10–4.13 (m, 1H, NCHCO), 4.88–5.04 (m, 1H, NHCHNH), 8.08 (d, J=8.5 Hz, 1H, NHCO₂Su), 8.49 (d, J=7.8 Hz, 1H, NHCOCH).—¹³C RMN ([D₆]DMSO, 50 MHz): δ=171.84 (C), 170.66 (C), 153.28 (C), 150.80 (C), 78.31 (C), 62.91 (CH), 59.19 (CH), 46.42 (CH₂), 31.61 (CH), 30.97 (CH₂), 27.98 (CH₃), 25.16 (CH₂), 22.81 (CH₂), 18.23 (CH₃).

Boc-Ile-gVal-COOSu (IIId)

Yield 62% white solid; HPLC t$_r$ 11.67 (linear gradient, 20–80% B, 20 min)—¹H RMN ([D₆]DMSO, 200 MHz): δ=0.64–0.91 (m, 12H, CH—(CH₃)₂, CH₃—CH—CH₂—CH₃), 0.97–1.05 (m, 1H, CH₃—CH—CH₂—CH₃) 1.27–1.37 (s, 10H, C(CH₃)₃, CH₃—CH—CH₂—CH₃), 1.56–1.63 (m, 1H, CH₃—CH—CH₂—CH₃), 1.80–1.94 (m, 1H, CH—CH—(CH₃)₂), 2.70 (s, 4H, CH₂—CH₂), 3.71–3.79 (m, 1H,NH—CH—CO), 4.87–4.99 (m, 1H, NHCHNH), 6.66 (d, J=8.9 Hz, 1H, NHBoc), 7.98 (d, J=8.7 Hz, 1H, NHCO₂Su), 8.53 (d, J=8.1 Hz, 1H, NHCOCH). —¹³C RMN ([D₆]DMSO, 50 MHz): δ=170.97 (C), 170.60 (C), 155.27 (C), 150.82 (C), 77.89 (C), 62.73 (CH), 58.64 (CH), 36.07 (CH), 31.67 (CH), 28.07 (CH₃), 25.18 (CH₂), 24.31 (CH₂), 18.34 (CH₃), 18.13 (CH₃), 15.24 (CH₃), 10.73 (CH₃).

Fmoc-Ile-gLeu-COOSu (IIIh)

Yield % white solid; HPLC t$_r$ 12.85 (linear gradient, 30–100% B, 20 min)—¹H RMN ([D₆]DMSO, 200 MHz): δ=(m, 12H, CH—(CH₃)₂, CH₃—CH—CH₂—CH₃), (m, 1H, CH₃—CH—CH₂—CH₃) (s, 10H, C(CH₃)₃, CH₃—CH—CH₂—CH₃), 1.56–1.63 (m, 1H, CH₃13 CH—CH₂—CH₃), 1.80–1.94 (m, 1H, CH—CH—(CH₃)₂), 2.70 (s, 4H, CH₂—CH₂), 3.71–3.79 (m, 1H,NH—CH—CO), 4.87–4.99 (m, 1H, NHCHNH), 6.66 (d, J=8.9 Hz, 1H, NHBoc), 7.98 (d, J=8.7 Hz, 1H, NHCO₂Su), 8.53 (d, J=8.1 Hz, 1H, NHCOCH). —¹³C RMN ( [D₆]DMSO, 50 MHz): δ=170.97 (C), 170.60 (C), 155.27 (C), 150.82 (C), 77.89 (C), 62.73 (CH), 58.64 (CH), 36.07 (CH), 31.67 (CH), 28.07 (CH₃), 25.18 (CH₂), 24.31 (CH₂), 18.34 (CH₃), 18.13 (CH₃) , 15.24 (CH₃) , 10.73 (CH₃).

2) Reactivity of carbamates (III) and (III bis) with amines and amino acids to give urea dipeptides or ureidopeptides It is seen that the carbamates (III) and (IIIbis) react with primary amines or amino acids in the presence of absence of a tertiary base (DIEA, NMM, Et₃N) at ambient temperature to give corresponding urea derivatives (VI) (Reaction 2) with good yields (table 2). The reaction is rapid and all the starting product is generally consumed in several hours. The N-hydroxysuccinimide is the only secondary product formed during the reaction and is easily eliminated by aqueous washing.

Reaction 2: Synthesis of ureas (VI) from carbamates (III) and (IIIbis).

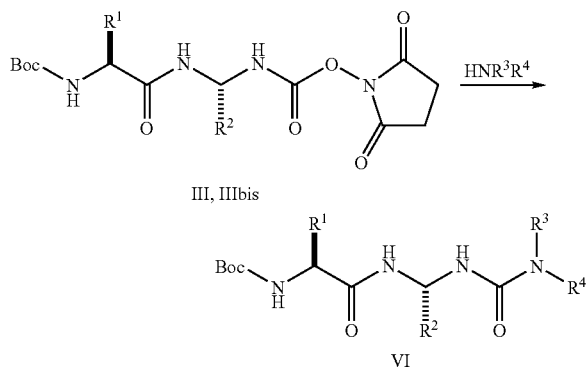

TABLE 2

Reactivity of carbamates (III) and (III bis) to give ureas (VI).

| Carbamate (III) and (III bis) | amine | Urea (VI) | Yield (%)[a] | HPLC t$_R$ (min)[b] | MALDI-MS |
|---|---|---|---|---|---|
| IIIf | HN(Me)₂ | Boc-Pro-gLeu-CON(Me)₂ | | | [c] |
| IIIf | HNMe | Boc-Pro-gLeu-CONHMe | | | [e] |
| IIIf | H-Phe-OMe | Boc-Pro-gLeu-CO-Phe-OMe | 92 | 15.1[e] | |
| IIIe | H₂N(i-Pr) | Boc-Lys(2-Cl-Z)-gVal-CONH(i-Pr) | 70 | 15.60[e] | 593.06 [M + Na]⁺ |

TABLE 2-continued

Reactivity of carbamates (III) and (III bis) to give ureas (VI).

| Carbamate (III) and (III bis) | amine | Urea (VI) | Yield (%)[a] | HPLC $t_R$ (min)[b] | MALDI-MS |
|---|---|---|---|---|---|
| IIIe | HN(Bn)$_2$ | Boc-Lys(2-Cl-Z)-gVal-CON(Bn)$_2$ | 74 | 18.25[e] | 731.68 [M + Na]$^+$ |
| IIId | H-Pro-Me | Boc-Ile-gVal-CO-Pro-OMe | 93 | 13.9[e] | |

[a] yield of (VI).
[b] linear gradient of A (0.1% TFA in H$_2$O) and b (MeCN containing 0.08% TFA),
[c] 20–80% B, 20 min,
[d] 30–100% B, 20 min,
[e] 0–100% B, 20 min.

The repetitive formation of urea by using carbamates (III) and (III bis) as activated monomers permits obtaining hybrid oligourea/peptides.

EXAMPLE IV

Examples of cyclic compounds corresponding to the formula (VIII bis)

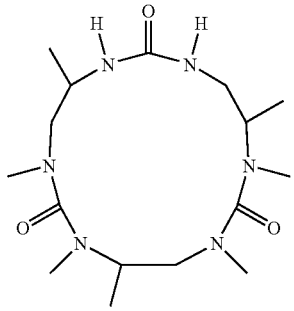

(VIII bis/1)

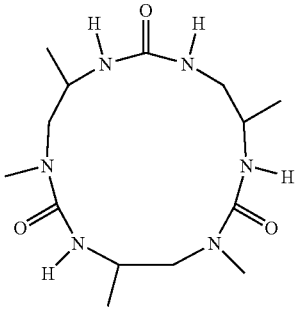

(VIII bis/2)

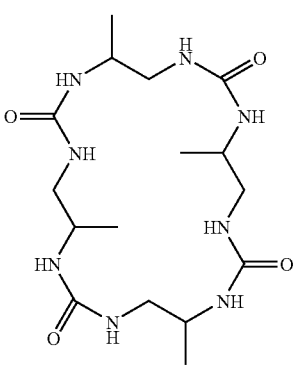

(VIII bis/3)

-continued

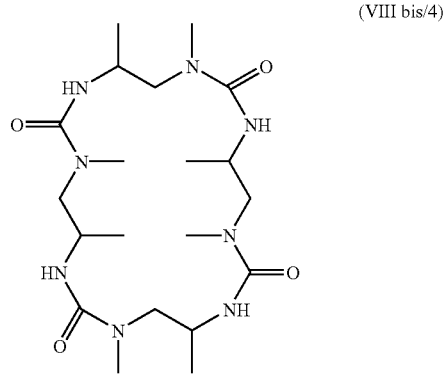

(VIII bis/4)

The compound (VIII bis/1) can for example be synthesized by intramolecular cyclization of the linear precursor hereinafter corresponding to the formula (VII/1) (1 mmol) by treatment with carbonyldiimidazole (1 mmol) in acetonitrile (200 ml) and in the presence of an excess of DIEA (2.5 mmol) for 12 hours.

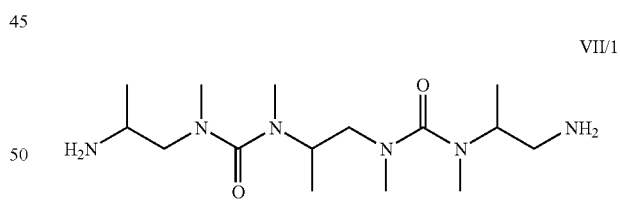

VII/1

After this time, the solvent is evaporated and the residue is purified by liquid chromatography in inverse phase (C18 column) using a linear water/acetonitrile gradient.

The linear precursor (VII/1) can be prepared according to reaction 1 below. The reaction of a first activated carbamate derived from an N-methylated beta amino acid on a monoprotected diamine, leads to the obtention of a trisubstituted monourea. The deprotection of the Boc group and the repeated reaction of the O-succinimidyle carbamate previously used, leads to the obtention of a di-urea. The successive deprotection of the protective groups Boc and Z gives the derivative (VII/1).

Reaction 1: Synthesis of the linear precursor (VII-1) used in the synthesis of the compound (VIII bis/1) (DMF=dimethylformamide, DIEA=diisopropylethylamine, TFA=trifluoroacetic acid)

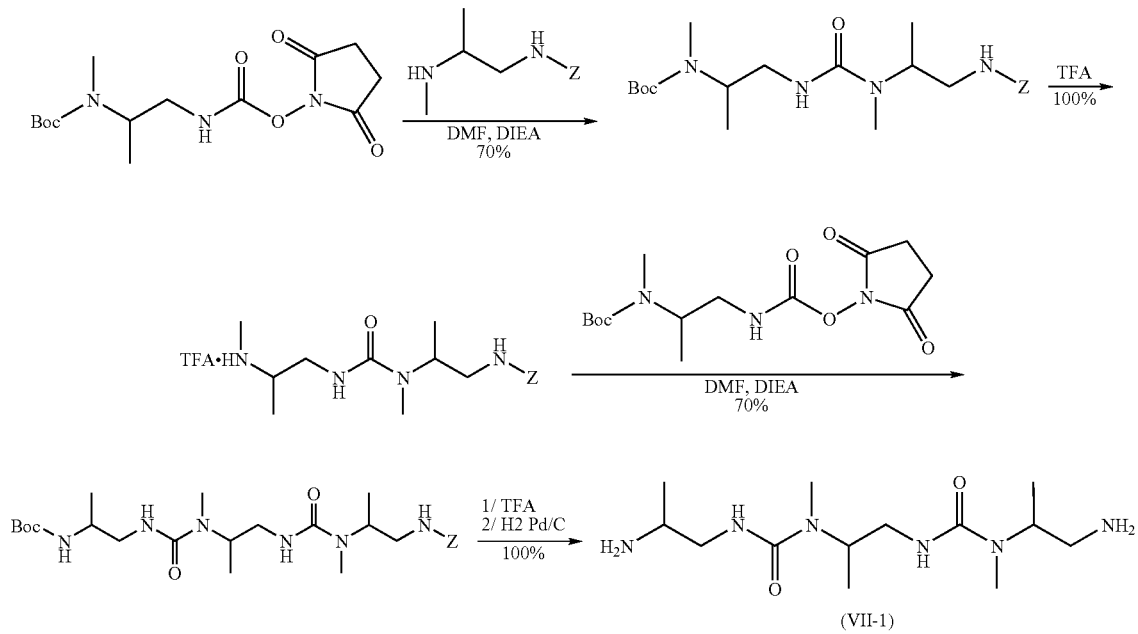

(VII-1)

REFERENCES (1) (a) Lam P. Y.; Jadhav P. K.; Eyermann C. J.; Hodge C. N.; Ru Y., Bacheler L. T.; Meek J. L.; Otto M. J.; Rayner M. M.; Wong Y. N.; Chang, C.-H.; Weber, P. C.; Jackson, D. A.; Sharpe, T. R.; Erickson-Viitanen, S. Science 1994 263, 380. (b) Castro J. L.; Ball R. G.; Broughton H. B.; Russell M. G., Rathbone D, Watt A. P., Baker R, Chapman K. L., Fletcher A. E., Patel S, Smith A. J., Marshall G. R., Ryecroft W, Matassa V. G. J. Med. Chem. 1996, 39(4):842 (c) von Geldern T. W., Kester J. A., Bal R, Wu-Wong J. R., Chiou W, Dixon D. B., Opgenorth T. J. J. Med. Chem. 1996 39, 968.

(2) (a) Nowick, J. S.; Smith, E. M.; Noronha, G. W. J. Org. Chem. 1995 60, 7386. (b) Nowick, J. S.; Mahrus, S.; Smith, E. M.; Ziller, J. W. J. Am. Chem. Soc. 1996 118, 1066. (c) Nowick, J. S.; Holmes, D. L.; Mackin, G.; Noronha, G; Shaka, A. J.; Smith, E. M. J. Am. Chem. Soc. 1996 118, 2764. (d) Holmes, D. H.; Smith, E. M.; Nowick, J. S. J. Am. Chem. Soc. 1997 119, 7665.

(3) (a) Burgess, K.; Linthicum, Shin, H. Angew. Chem. Int. Ed. Engl. 1995 34, 907. (b) Burgess, K.; Ibarzo, J.; Linthicum, D. S.; Russell, D. H.; Shin, H.; Shitangkoon, A.; Totani, R.; Zhang, A. J. J. Am. Chem. Soc. 1997 119, 1556. (c) Kim, J.-M.; Bi, Y.; Paikoff, S. J.; Schultz, P. G. Tetrahedron Lett. 1996 37, 5305. (d) Kim, J.-M.; Wilson, T. E.; Norman, T. C.; Schultz, P. G. Tetrahedron Lett. 1996, 37, 5309. (e) Kruijtzer J. A. W.; Lefeber, D. J.; Liskamp, R. M. J. Tetrahedron Lett. 1997 38, 5335. (f) Wilson, M. E.; Nowick, J. S. Tetrahedron Lett. 1998 39, 6613.

(4) Use of the phosgene and its derivatives, see: (a), Majer, P.; Randad, R. S.; J. Org. Chem. 1994 59, 1937 (b) Scialdone, M. A.; Shuey, S. W.; Soper, P.; Hamuro, Y.; Burns, D. M. J. Org. Chem. 1998 63, 4802–4807. Carbonates, see: (c) Takeda, K.; Akagi, Y.; Saiki, A.; tsukahara, T.; Ogura, H. Tetrahedron Lett. 1983 24, 4569. Izdebski, J.; Pawlak, D. Synthesis 1989, 423. N, N' carbodiimidazole, see: (d) Zhang, X.; Rodrigues, J.; Evans, L.; Hinckle, B.; Ballantyne, L.; Pena. J. Org. Chem. 1997 62, 6420. 1,1'-carbonylbisbenzotriazole, see: (e) Katritzky, A. R.; Pleynet, D. P. M.; Yang, B. J. Org. Chem. 1997 62, 4155.

(5) (a) Nowick, J. S.; Powell, N. A.; Nguyen, T. M.; Noronha, G. J. Org. Chem. 1992 57, 7364. (b) Reference 3b.

(6) (a) Martinez, J.; Oiry, J.; Imbach, J.-L, winternitz, F. J. Med. Chem. 1982 25, 178. (b) Hutchins, S. M.; Chapman, K. T. Tetrahedron Lett. 1994 35, 4055. (c) Thavonekham, B. Synthesis 1997, 1189.

(8) It is interesting to note that in the synthesis of oligoanthranilamides, the Hamilton group uses 2-nitrobenzoic acid in place of N-benzoylanthranillic acid. In this case, the nitro group as the masking group of the amine it is necessary to avoid the formation of azlactone: Hamuro, Y.; Geib, S. J.; Hamilton, A. D. J. Am. Chem. Soc. 1996 118, 7529.

(9) We have used the code with a letter proposed by Burgess for the urea oligomers[3b]. As an alternative, we propose the following abbreviation which permits the use of the code with a letter for the amino acids: Boc(-β³-HAla$^u$)$_2$-i-Pr (VIe) and Boc (-β³-HAla$^u$)$_3$-i-Pr (VIf). According to the nomenclature of Spatola[11] for the pseudopeptides, we can also write: Boc(-β³-HAla-[NHCONH])$_2$-i-Pr (VIe) et Boc(-β³-HAla-[NHCONH])$_3$-i-Pr (VIf).

(10) (a) Podlech, J.; Seebach, D. Liebigs Ann. 1995, 1217. (b) Seebach, D.; Overhand, M.; Kühnle, F. N. M.; Martinoni, B.; Oberer, L.; Hommel, U.; Widmer, H. Helv. Chim. Acta 1996 79, 913.

(11) Spatola, A. F. In Chemistry and Biochemistry of Amino acids, peptides and Proteins; Weinstein, B. Ed.; Marcel Dekker Inc.: New York, 1983; Vol. 7, pp267–357.

What is claimed is:
1. A compound having the formula (I bis)

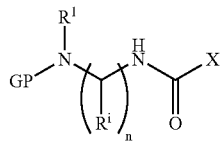
(I bis)

wherein
"n" is 1 or 2,
"i" is a whole number varying from 2 to n+1,
GP is selected from the group consisting of:
an oxycarbonyl group ROCO, R representing an alkyl group of 1 to 20 carbon atoms, unsubstituted or substituted with an aryl group whose cyclic structure contains 5 to 20 carbon atoms, said alkyl group being saturated or not,
an acyl group RCO, R being chosen from: an alkyl group of 1 to 20 carbon atoms or an aryl group whose cyclic structure contains 5 to 20 carbon atoms, said alkyl group being possibly substituted with an aryl group whose cyclic structure contains 5 to 20 carbon atoms, said alkyl group being saturated or not,
GP along with $R^1$ and the N then are bonded to form a phthalimido group of formula:

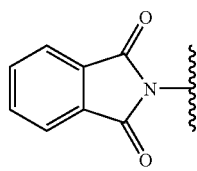

a biotinyle group having the following formula

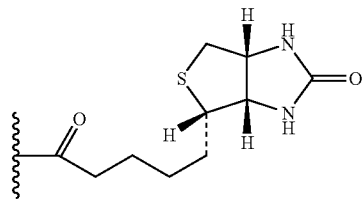

groups $R^1$ and $R^i$ can each represent independently from each other: a hydrogen, a halogen, the protected or unprotected side chain of an amino acid selected from natural and synthetic amino acids, a $(C_1-C_{20})$ alkyl group, unsubstituted or substituted, an aryl group whose cyclic structure contains 5 to 20 carbon atoms, a group $OR_a$, —$NH_2$, —OH, —$COOR_a$, —$CONHR_a$, —$CONH_2$, —$CH_2COOR_a$, —$CH_2CONHR_a$, —$CH_2CONH_2$,
$R_a$ representing an alkyl group, saturated or not, having 1 to 20 carbon atoms, an aralkyl group having 1 to 20 carbon atoms, or an aryl group whose cyclic structure contains 5 to 20 carbon atoms,
$R^1$ and $R^i$ groups can also form a cycle with N, said cycle being selected from the group consisting of

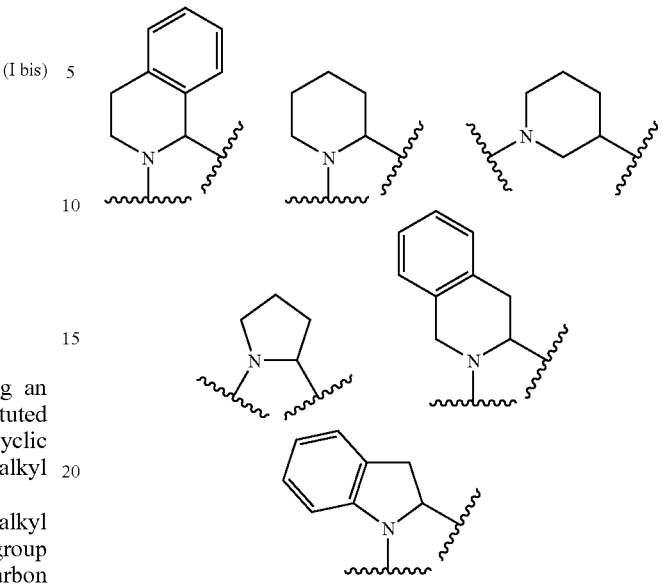

X group represents a group having one of the following formula:

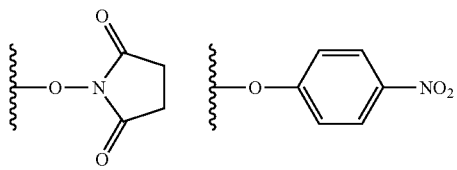

wherein said compound is not one of the following compounds selected from the group consisting of:
n=2, GP=Boc, $R^1$=isobutyl, $R^2=R^3$=H, X=4-nitrophenol;
n=2, GP=Boc, $R^1$=benzyl, $R^2=R^3$=H, X=4-nitrophenol;
n=2, GP=Boc, $R^1$=$CH_2$-p-$C_6H_4$Ot-Bu, $R^2=R^3$=H, X=4-nitrophenol;
n=2, GP=Boc, $R^1$=H, $R^2=R^3$=H, X=4-nitrophenol.

2. The compound according to claim 1, wherein GP represents an oxycarbonyl group chosen from Boc, Fmoc, benzyloxycarbonyl or allyloxycarbonyl.

3. The compound according to claim 1, in which X is a N-hydroxysuccinimide group and has the following formula:

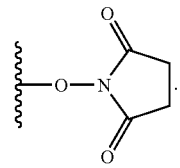

4. The compound according to claim 1, wherein the alkyl group corresponding to $R^1$ or $R^i$ is substituted with one or several substituents selected from the group consisting of —$COOR_h$, —$CONHR_h$, —COOH, —OH, —$OR_h$, —NHR$_h$, —NH$_2$, —NH(CO)R$_h$, an aryl group whose cyclic structure contains 5 to 20 carbon atoms, halogen, carbonyl, nitrile, and guanidino, R$_h$ representing an alkyl group, saturated or not, having 1 to 20 carbon atoms, an aralkyl group having 1 to 20 carbon atoms, or an aryl group whose cyclic structure contains 5 to 20 carbon atoms.

5. The compound according to claim 1, having the following formula

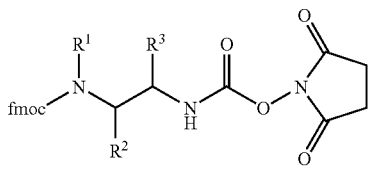

wherein R$^2$ represents a (C$_1$–C$_{20}$) alkyl group, optionally substituted with a phenyl group, and wherein said phenyl group is optionally substituted with an alkoxy group.

6. The compound according to claim 1, having the following formula:

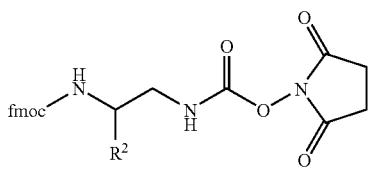

wherein R$^2$ represents a (C$_1$–C$_{20}$) alkyl group, optionally substituted with a pvhenyl group, and wherein said phenyl group is optionally substituted with an alkoxy group.

7. A compound having the following formula:

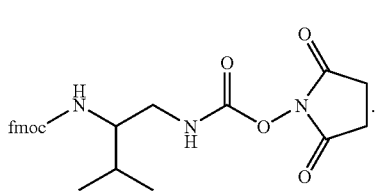
(Ii)

8. A process for preparing a compound according to claim 1, comprising:
providing a compound of formula (IX)

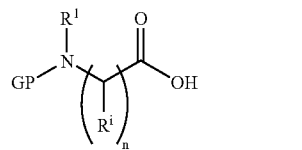
(IX)

transforming said compound (IX) into a corresponding acyl azide (XII)

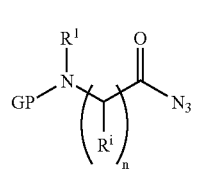
(XII)

transforming said acyl azide (XII) by Curtius rearrangement into a corresponding isocyanate (II), treating said isocyanate (II) under conditions that provide a carbamic acid compound of formula (I bis).

9. The process according to claim 8, wherein transforming said compound (IX) into a corresponding acyl azide (XII) is carried out by treatment of a mixed anhydride, formed by the reaction of acid compound (IX) with ethyl or isobutyl chloroformiate in the presence of a tertiary amine, wherein said tertiary amine is NMM (N-methylmorpholine), DIEA (di-isopropylethylamine), or Et$_3$N in THF (tetrahydrofurane) with a sodium azide solution, wherein said step of transforming acyl azide (XII) into a corresponding isocyanate (II), is carried out by heating a solution of acyl azide in a solvent, and wherein a compound selected from the group consisting of N-hydroxysuccinimide is the compound treating isocyanate (II) to obtain a carbamic acid derivative of formula (I bis).

10. A compound having the formula (I bis)

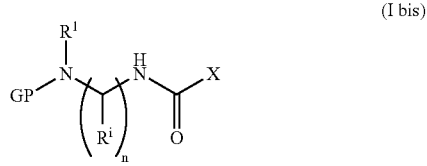
(I bis)

wherein
"n" is 1 or 2,
"i" is a whole number varying from 2 to n+1,
GP is selected from the group consisting of:
an oxycarbonyl group ROCO, R representing an alkyl group of 1 to 20 carbon atoms, unsubstituted or substituted with an aryl group whose cyclic structure contains 5 to 20 carbon atoms, said alkyl group being saturated or not, an acyl group RCO, R being chosen from: an alkyl group of 1 to 20 carbon atoms or an aryl group whose cyclic structure contains 5 to 20 carbon atoms, said alkyl group being possibly substituted with an aryl group whose cyclic structure contains 5 to 20 carbon atoms, said alkyl group being saturated or not, GP along with R$^1$ and the N then are bonded to form a phthalimido group of formula:

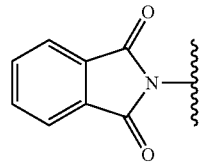

a biotinyle group having the following formula

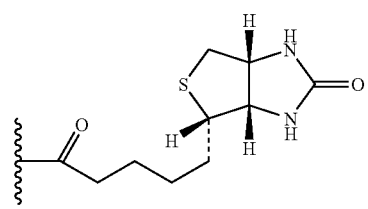

groups $R^1$ and $R^i$ can each represent independently from each other: a hydrogen, a halogen, the protected or unprotected side chain of an amino acid selected from natural and synthetic amino acids, a $(C_1-C_{20})$ alkyl group, unsubstituted or substituted, an aryl group whose cyclic structure contains 5 to 20 carbon atoms, a group $OR_a$, —$NH_2$, —OH, —$COOR_a$, —$CONHR_a$, —$CONH_2$, —$CH_2COOR_a$, —$CH_2CONHR_a$, —$CH_2CONH_2$, $R^a$ representing an alkyl group, saturated or not, having 1 to 20 carbon atoms, an aralkyl group having 1 to 20 carbon atoms, or an aryl group whose cyclic structure contains 5 to 20 carbon atoms, wherein $R^1 R^i$ groups can also form a cycle with N, said cycle being selected from the group consisting of

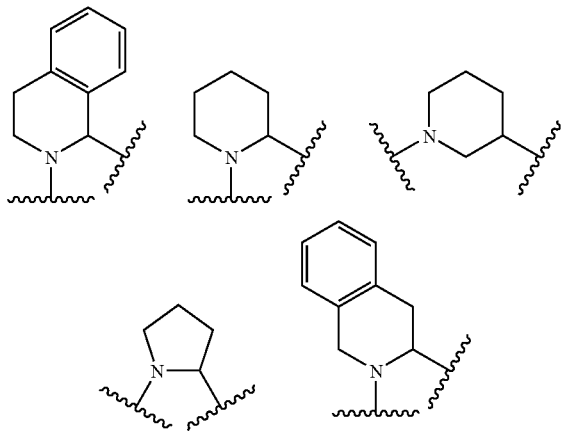

-continued

X group represents O-succinimidyl, wherein said compound is not one of the following compounds selected from the group consisting of:

n=2, GP=Boc, $R^1$=isobutyl, $R^2$=$R^3$=H, X=4-nitrophenol;

n=2, GP=Boc, $R^1$=benzyl, $R^2$=$R^3$=H, X=4-nitrophenol;

n=2, GP=Boc, $R^1$=$CH_2$-p-$C_6H_4$Ot-Bu, $R^2$=$R^3$=H, X=4-nitrophenol;

n=2, GP=Boc, $R^1$=H, $R^2$=$R^3$=H, X=4-nitrophenol.

11. The compound according to claim 10, wherein GP represents an oxycarbonyl group chosen from Boc, Fmoc, benzyloxycarbonyl or allyloxycarbonyl.

12. The compound according to claim 10, wherein X is a O-succinimidyl.

13. The compound according to claim 10, wherein the alkyl group corresponding to $R^1$ or $R^i$ is substituted with one or several substituents selected from the group consisting of —$COOR_h$, —$CONHR_h$, —COOH, —OH, —$OR_h$, —$NHR_h$, —$NH_2$, —NH(CO)$R_h$, an aryl group whose cyclic structure contains 5 to 20 carbon atoms, halogen, carbonyl, nitrile, and guanidino, $R_h$ representing an alkyl group, saturated or not, having 1 to 20 carbon atoms, an aralkyl group having 1 to 20 carbon atoms, or an aryl group whose cyclic structure contains 5 to 20 carbon atoms.

* * * * *